(12) United States Patent
Polo et al.

(10) Patent No.: US 7,771,979 B2
(45) Date of Patent: Aug. 10, 2010

(54) COMPOSITIONS AND METHODS FOR GENERATING AN IMMUNE RESPONSE UTILIZING ALPHAVIRUS-BASED VECTOR SYSTEMS

(75) Inventors: John Polo, Hayward, CA (US); Thomas W. Dubensky, Jr., Piedmont, CA (US); Ilya Frolov, St. Louis, MO (US); Jason P. Gardner, Pittsburg, CA (US); Gillis Otten, Foster City, CA (US); Susan Barnett, San Francisco, CA (US); David A. Driver, Solana Beach, CA (US)

(73) Assignee: Novartis Vaccines & Diagnostics, Inc., Emeryville, CA (US)

( * ) Notice: Subject to any disclaimer, the term of this patent is extended or adjusted under 35 U.S.C. 154(b) by 352 days.

(21) Appl. No.: 11/712,044

(22) Filed: Feb. 27, 2007

(65) Prior Publication Data

US 2008/0226598 A1    Sep. 18, 2008

Related U.S. Application Data

(63) Continuation of application No. 09/551,977, filed on Apr. 14, 2000, now abandoned.

(60) Provisional application No. 60/191,363, filed on Mar. 22, 2000, provisional application No. 60/148,086, filed on Aug. 9, 1999, provisional application No. 60/129,498, filed on Apr. 14, 1999.

(51) Int. Cl.
*C12N 7/08* (2006.01)
*A61K 35/76* (2006.01)

(52) U.S. Cl. ................. 435/235.1; 424/205.1; 424/93.1; 435/320.1

(58) Field of Classification Search ............... 435/320.1; 424/205.1
See application file for complete search history.

(56) References Cited

U.S. PATENT DOCUMENTS

| | | | |
|---|---|---|---|
| 5,026,686 A | 6/1991 | Schlesinger et al. | |
| 5,091,309 A | 2/1992 | Schlesinger et al. | |
| 5,185,440 A | 2/1993 | Davis et al. | |
| 5,217,879 A | 6/1993 | Huang et al. | |
| 5,466,788 A | 11/1995 | Ahlquist et al. | |
| 5,505,947 A | 4/1996 | Johnston et al. | |
| 5,532,154 A | 7/1996 | Brown | |
| 5,578,475 A | 11/1996 | Jessee | |
| 5,591,579 A | 1/1997 | Olivo et al. | |
| 5,643,576 A | 7/1997 | Johnston et al. | |
| 5,691,177 A | 11/1997 | Guber et al. | |
| 5,739,026 A | 4/1998 | Garoff et al. | |
| 5,766,602 A | 6/1998 | Xiong et al. | |
| 5,789,245 A | 8/1998 | Dubensky, Jr. et al. | |
| 5,792,462 A | 8/1998 | Johnston et al. | |
| 5,797,870 A | 8/1998 | March et al. | |
| 5,811,407 A | 9/1998 | Johnston et al. | |
| 5,814,482 A | 9/1998 | Dubensky, Jr. et al. | |
| 5,843,712 A | 12/1998 | Levine | |
| 5,843,723 A | 12/1998 | Dubensky, Jr. et al. | |
| 5,851,757 A | 12/1998 | Olivo et al. | |

OTHER PUBLICATIONS

Rolls et al., "Expression of Additional Genes in a Vector Derived from a Minimal RNA Virus," Virology, 218: 406-411, 1996.
Strauss et al., "The Alphaviruses: Gene expression, Replication, and Evolution," Microbiological Reviews 58(3): 491-562 1994.
Salio et al., "Inhibition of Dendritic Cell Maturation by Herpes Simplex Virus," Eur. J. Immunol. 29:3245-3253, 1999.
Schlessinger et al., "Alphavirus Vectors for Gene Expression and Vaccines," Curr. Opin. Biotechnol. 10: 434-439, 1999.
Timmerman et al., "Dendritic Cell Vaccines for Cancer Immunotherapy," Annu. Rev. Med. 50: 507-529, 1999.
van Wilsem et al., "Antigen-bearing Langerhans Cells in Skin Draining Lymph Nodes: Phenotype and Kinetics of Migration," J. Invest. Dermatol. 103: 217-220, 1994.
zur Megede et al., "Increased Expression and Immunogenicity of Sequence-Modified Human Immunodeficiency Virus Type 1 gag Gene," J. Virol. 74:2628-2635, 2000.
Steinman, "The Dendritic Cell System and its Role in Immunogenicity," Annu. Rev. Immunol. 9:271-296, 1991.
Baltz, "Vaccines in the Treatment of Cancer" American Journal of Health-System Pharmacy. 52(22): 2574-2585, 1995.
Wang et al., "DNA Innoculation Induce Protective in vivo Immune Responses Against Cellular Challenge with HIV-1 Antigen-Expressing Cells," AIDS Research and Human Retroviruses 10 (S2): 35-41, 1994.
Bueler et al., "Retrovirus-Transduced Antigen Presenting Cells for the Specific Immunotherapy of Cancer," Gene Ther. Meeting Cold Spring Harbor, Abstract, 1994.
Baier et al., "Immunogenic Targeting of Recombinant Peptide Vaccines to Human Antigen-Presenting Cells by Chimeric Anti-HLA-DR and anti-surface immunoglobulin D antibody Fab fragments in vivo," J. Virology 69(4): 2357-2365, 1995.
Henderson et al., "Using Human Dendritic Cells to Augment the Immune Response to Tumor-associated Mucin," J. Cell. Biochem. Suppl. 21A:19, 1995.
Zitvogel et al., "Cancer Vaccines Engineered with IL-2/IL-12 and B7-1: Towards Adaptive Immunotherapy using Genetically Modified Dendritic cells," Cancer Gene Therapy 2(3): A17, 1995.
Russell et al., "Sindbis virus mutations which coordinately affect glycoprotein processing, penetration, and virulence in mice," J Virol. Apr. 1989;63(4):1619-29.
Strauss et al., "Identification of antigenically important domains in the glycoproteins of Sindbis virus by analysis of antibody escape variants," J Virol. Sep. 1991;65(9):4654-64.
Strauss et al., "Complete nucleotide sequence of the genomic RNA of Sindbis virus," Virology. Feb. 1984;133 (1):92-110.
Schoepp et al., "Sindbis virus pathogenesis: phenotypic reversion of an attenuated strain to virulence by second-site intragenic suppressor mutations," J Gen Virol. Aug. 1993;74 (Pt 8):1691-5.
Tucker et al., "Amino acid changes in the Sindbis virus E2 glycoprotein that increase neurovirulence improve entry into neuroblastoma cells," J Virol. Aug. 1997;71(8):6106-12.

*Primary Examiner*—Patrick Nolan
*Assistant Examiner*—Bao Qun Li
(74) *Attorney, Agent, or Firm*—Helen Lee; Regina Bautista

(57) ABSTRACT

Methods are provided for generating immune responses utilizing alphavirus-based vector systems.

21 Claims, 18 Drawing Sheets

```
ATTGACGGCGTAGTACACACTATTGAATCAAACAGCCGACCAATTGCACTACCATCACAATGGAGAAGCCAGTAG
TAAACGTAGACGTAGACCCCCAGAGTCCGTTTGTCGTGCAACTGCAAAAAAGCTTCCCGCAATTTGAGGTAGTAG
CACAGCAGGTCACTCCAAATGACCATGCTAATGCCAGAGCATTTTCGCATCTGGCCAGTAAACTAATCGAGCTGG
AGGTTCCTACCACAGCGACGATCTTGGACATAGGCAGCGCACCGGCTCGTAGAATGTTTCCGAGCACCAGTATC
ATTGTGTCTGCCCCATGCGTAGTCCAGAAGACCCGGACCGCATGATGAAATATGCCAGTAAACTGGCGGAAAAAG
CGTGCAAGATTACAAACAAGAACTTGCATGAGAAGATTAAGGATCTCCGGACCGTACTTGATACGCCGGATGCTG
AAACACCATCGCTCTGCTTTCACAACGATGTTACCTGCAACATGCGTGCCGAATATTCCGTCATGCAGGACGTGT
ATATCAACGCTCCCGGAACTATCTATCATCAGGCTATGAAAGGCGTGCGGACCCTGTACTGGATTGGCTTCGACA
CCACCCAGTTCATGTTCTCGGCTATGGCAGGTTCGTACCCTGCGTACAACACCAACTGGGCCGACGAGAAAGTCC
TTGAAGCGCGTAACATCGGACTTTGCAGCACAAAGCTGAGTGAAGGTAGGACAGGAAAATTGTCGATAATGAGGA
AGAAGGAGTTGAAGCCCGGGTCGCGGGTTTATTTCTCCGTAGGATCGACACTTTATCCAGAACACAGAGCCAGCT
TGCAGAGCTGGCATCTTCCATCGGTGTTCCACTTGAATGGAAAGCAGTCGTACACTTGCCGCTGTGATACAGTGG
TGAGTTGCGAAGGCTACGTAGTGAAGAAAATCACCATCAGTCCCGGGATCACGGGAGAAACCGTGGGATACGCGG
TTACACACAATAGCGAGGGCTTCTTGCTATGCAAAGTTACTGACACAGTAAAAGGAGAACGGGTATCGTTCCCTG
TGTGCACGTACATCCCGGCCACCATATGCGATCAGATGACTGGTATAATGGCCACGGATATATCACCTGACGATG
CACAAAAACTTCTGGTTGGGCTCAACCAGCGAATTGTCATTAACGGTAGGACTAACAGGAACACCAACACCATGC
AAAAATTACCTTCTGCCGATCATAGCACAAGGGTTCAGCAAATGGGCTAAGGAGCGCAAGGATGATCTTGATAACG
AGAAAATGCTGGGTACTAGAGAACGCAAGCTTACGTACGGCTGCTTGTGGGCGTTTCGCACTAAGAAAGTACATT
CGTTTTATCGCCCACCTGGAACGCAGACCATCGTAAAAGTCCCAGCCTCTTTTAGCGCTTTTCCCATGTCGTCCG
TATGGACGACCTCTTTGCCCATGTCGCTGAGGCAGAAATTGAAACTGGCATTGCAACCAAAGAAGGAGGAAAAAC
TGCTGCAGGTCTCGGAGGAATTAGTCATGGAGGCCAAGGCTGCTTTTGAGGATGCTCAGGAGGAAGCCAGAGCGG
AGAAGCTCCGAGAAGCACTTCCACCATTAGTGGCAGACAAAGGCATCGAGGCAGCCGCAGAAGTTGTCTGCGAAG
TGGAGGGGCTCCAGGCGGACATCGGAGCAGCATTAGTTGAAACCCCGCGCGGTCACGTAAGGATAATACCTCAAG
CAAATGACCGTATGATCGGACAGTATATCGTTGTCTCGCCAAACTCTGTGCTGAAGAATGCCAAACTCGCACCAG
CGCACCCGCTAGCAGATCAGGTTAAGATCATAACACACTCCGGAAGATCAGGAAGGTACGCGGTCGAACCATACG
ACGCTAAAGTACTGATGCCAGCAGGAGGTGCCGTACCATGGCCAGAATTCCTAGCACTGAGTGAGAGCGCCACGT
TAGTGTACAACGAAAGAGAGTTTGTGAACCGCAAACTATACCACATTGCCATGCATGGCCCCGCCAAGAATACAG
AAGAGGAGCAGTACAAGGTTACAAAGGCAGAGCTTGCAGAAACAGAGTACGTGTTTGACGTGGACAAGAAGCGTT
GCGTTAAGAAGGAAGAAGCCTCAGGTCTGTTCCTCTCGGGAGAACTGACCAACCCTCCCTATCATGAGCTAGCTC
TGGAGGGACTGAAGACCCGACCTGCGGTCCCGTACAAGGTCGAAACAATAGGAGTGATAGGCACACCGGGTCGG
GCAAGTCAGCTATTATCAAGTCAACTGTCACGGCACGAGATCTTGTTACCAGCGGAAAGAAAGAAAATTGTCGCG
AAATTGAGGCCGACGTGCTAAGACTGAGGGGTATGCAGATTACGTCGAAGACAGTAGATTCGGTTATGCTCAACG
GATGCCACAAAGCCGTAGAAGTGCTGTACGTTGACGAAGCGTTCGCGTGCCACGCAGGAGCACTACTTGCCTTGA
TTGCTATCGTCAGGCCCCGCAAGAAGGTAGTACTATGCGGAGACCCCATGCAATGCGGATTCTTCAACATGATGC
AACTAAAGGTACATTTCAATCACCCTGAAAAAGACATATGCACCAAGACATTCTACAAGTATATCTCCCGGCGTT
GCACACAGCCAGTTACAGCTATTGTATCGACACTGCATTACGATGGAAAGATGAAAACCACGAACCCGTGCAAGA
AGAACATTGAAATCGATATTACAGGGGCCACAAAGCCGAAGCCAGGGGATATCATCCTGACATGTTTCCGCGGGT
GGGTTAAGCAATTGCAAATCGACTATCCCGGACATGAAGTAATGACAGCCGCGGCCTCACAAGGGCTAACCAGAA
AAGGAGTGTATGCCGTCCGGCAAAAAGTCAATGAAAACCCACTGTACGCGATCACATCAGAGCATGTGAACGTGT
TGCTCACCCGCACTGAGGACAGGCTAGTGTGGAAAACCTTGCAGGGCGACCCATGGATTAAGCAGCTCACTAACA
TACCTAAAGGAAACTTTCAGGCTACTATAGAGGACTGGGAAGCTGAACACAAGGGAATAATTGCTGCAATAAACA
GCCCCACTCCCCGTGCCAATCCGTTCAGCTGCAAGACCAACGTTTGCTGGGCGAAAGCATTGGAACCGATACTAG
CCACGGCCGGTATCGTACTTACCGGTTGCCAGTGGAGCGAACTGTTCCCACAGTTTGCGGATGACAAACCACATT
CGGCCATTTACGCCTTAGACGTAATTTGCATTAAGTTTTTCGGCATGGACTTGACAAGCGGACTGTTTTCTAAAC
AGAGCATCCCACTAACGTACCATCCCGCCGATTCAGCGAGGCCGGTAGCTCATTGGGACAACAGCCCAGGAACCC
GCAAGTATGGGTACGATCACGCCATTGCCGCCGAACTCTCCCGTAGATTTCCGGTGTTCCAGCTAGCTGGGAAGG
GCACACAACTTGATTTGCAGACGGGAGAACCAGAGTTATCTCTGCACAGCATAACCTGGTCCCGGTGAACCGCA
ATCTTCCTCACGCCTTAGTCCCCGAGTACAAGGAGAAGCAACCCGGCCCGGTCGAAAAATTCTTGAACCAGTTCA
AACACCACTCAGTACTTGTGGTATCAGAGGAAAAATTGAAGCTCCCCGTAAGAGAATCGAATGGATCGCCCCGA
TTGGCATAGCCGGTGCAGATAAGAACTACACCCACTTTCAGCAGTGCGAAGACCATGCGGCGACCTTAAAAACCC
TCATCAACATTGGAACTAAATACAGAAACCACCACTTTCAGCAGTGCGAAGACCATGCGGCGACCTTAAAAACCC
TTTCGCGTTCGGCCCTGAATTGCCTTAACCCAGGAGGCACCCTCGTGGTGAAGTCCTATGGCTACGCCGACCGCA
ACAGTGAGGACGTAGTCACCGCTCTTGCCAGAAAGTTTGTCAGGGTGTCTGCAGCGAGACCAGATTCTGTCTCAA
```

FIG. 2B-1

```
GCAATACAGAAATGTACCTGATTTTCCGACAACTAGACAACAGCCGTACACGGCAATTCACCCCGCACCATCTGA
ATTGCGTGATTTCGTCCGTGTATGAGGGTACAAGAGATGGAGTTGGAGCCGCGCCGTCATACCGCACCAAAAGGG
AGAATATTGCTGACTGTCAAGAGGAAGCAGTTGTCAACGCAGCCAATCCGCTGGGTAGACCAGGCGAAGGAGTCT
GCCGTGCCATCTATAAACGTTGGCCGACCAGTTTTACCGATTCAGCCACGGAGACAGGCACCGCAAGAATGACTG
TGTGCCTAGGAAAGAAAGTGATCCACGCGGTCGGCCCTGATTTCCGGAAGCACCCAGAAGCAGAAGCCTTGAAAT
TGCTACAAAACGCCTACCATGCAGTGGCAGACTTAGTAAATGAACATAACATCAAGTCTGTCGCCATTCCACTGC
TATCTACAGGCATTTACGCAGCCGGAAAAGACCGCCTTGAAGTATCACTTAACTGCTTGACAACCGCGCTAGACA
GAACTGACGCGGACGTAACCATCTATTGCCTGGATAAGAAGTGGAAGGAAAGAATCGACGCGGCACTCCAACTTA
AGGAGTCTGTAACAGAGCTGAAGGATGAAGATATGGAGATCGACGATGAGTTAGTATGGATCCATCCAGACAGTT
GCTTGAAGGGAAGAAAGGGATTCAGTACTACAAAAGGAAAATTGTATTCGTACTTCGAAGGCACCAAATTCCATC
AAGCAGCAAAAGACATGGCGGAGATAAAGGTCCTGTTCCCTAATGACCAGGAAAGTAATGAACAACTGTGTGCCT
ACATATTGGGTGAGACCATGGAAGCAATCCGCGAAAAGTGCCCGGTCGACCATAACCCGTCGTCTAGCCCGCCCA
AAACGTTGCCGTGCCTTTGCATGTATGCCATGACGCCAGAAAGGGTCCACAGACTTAGAAGCAATAACGTCAAAG
AAGTTACAGTATGCTCCTCCACCCCCCTTCCTAAGCACAAAATTAAGAATGTTCAGAAGGTTCAGTGCACGAAAG
TAGTCCTGTTTAATCCGCACACTCCCGCATTCGTTCCCGCCCGTAAGTACATAGAAGTGCCAGAACAGCCTACCG
CTCCTCCTGCACAGGCCGAGGAGGCCCCCGAAGTTGTAGCGACACCGTCACCATCTACAGCTGATAACACCTCGC
TTGATGTCACAGACATCTCACTGGATATGGATGACAGTAGCGAAGGCTCACTTTTTTCGAGCTTTAGCGGATCGG
ACAACTCTATTACTAGTATGGACAGTTGGTCGTCAGGACCTAGTTCACTAGAGATAGTAGACCGAAGGCAGGTGG
TGGTGGCTGACGTTCATGCCGTCCAAGAGCCTGCCCCTATTCCACCGCCAAGGCTAAAGAAGATGGCCCGCCTGG
CAGCGGCTAGAAAAGAGCCCACTCCACCGGCAAGCAATAGCTCTGAGTCCCTCCACCTCTCTTTTGGTGGGGTAT
CCATGTCCCTCGGATCAATTTTCGACGGAGAGACGGCCCGCGCGGTACAACCCCTGGCAACAGGCCCCA
CGGATGTGCCTATGTCTTTCGGATCGTTTTCGACGGAGAGATTGATGAGCTGAGCCGCAGAGTAACTGAGTCCG
AACCCGTCCTGTTTGGATCATTTGAACCGGGCGAAGTGAACTCAATTATATCGTCCCGATCAGCCGTATCTTTTC
CACTACGCAAGCAGAGACGTAGACGCAGGAGCAGGAGGACTGAATACTGACTAACCGGGGTAGGTGGGTACATAT
TTTCGACGGACACAGGCCCTGGGCACTTGCAAAAGAAGTCCGTTCTGCAGAACCAGCTTACAGAACCGACCTTGG
AGCGCAATGTCCTGGAAAGAATTCATGCCCCGGTGCTCGACACGTCGAAAGAGGAACAACTCAAACTCAGGTACC
AGATGATGCCCACCGAAGCCAACAAAAGTAGGTACCAGTCTCGTAAAGTAGAAAATCAGAAAGCCATAACCACTG
AGCGACTACTGTCAGGACTACGACTGTATAACTCTGCCACAGATCAGCCAGAATGCTATAAGATCACCTATCCGA
AACCATTGTACTCCAGTAGCGTACCGGCGAACTACTCCGATCCACAGTTCGCTGTAGCTGTCTGTAACAACTATC
TGCATGAGAACTATCCGACAGTAGCATCTTATCAGATTACTGACGAGTACGATGCTTACTTGGATATGGTAGACG
GGACAGTCGCCTGCCTGGATACTGCAACCTTCTGCCCCGCTAAGCTTAGAAGTTACCCGAAAAAACATGAGTATA
GAGCCCCGAATATCCGCAGTGCGGTTCCATCAGCGATGCAGAACACGCTACAAAATGTGCTCATTGCCGCAACTA
AAAGAAATTGCAACGTCACGCAGATGCGTGAACTGCCAACACTGGACTCAGCGACATTCAATGTCGAATGCTTTC
GAAAATATGCATGTAATGACGAGTATTGGGAGGAGTTCGCTCGGAAGCCAATTAGGATTACCACTGAGTTTGTCA
CCGCATATGTAGCTAGACTGAAAGGCCCTAAGGCCGCCGCACTATTTGCAAAGACGTATAATTTGGTCCCATTGC
AAGAAGTGCCTATGGATAGATTCGTCATGGACATGAAAAGGGACGTGAAAGTTACACCAGGCACGAAACACACAG
AAGAAAGACCGAAAGTACAAGTGATACAAGCCGCAGAACCCCTGGCGACTGCTTACTTATGCGGGATTCACCGGG
AATTAGTGCGTAGGCTTACGGCCGTCTTGCTTCCAAACATTCACACGCTTTTTGACATGTCGGCGGAGGATTTTG
ATGCAATCATAGCAGAACACTTCAAGCAAGGCGACCCCGGTACTGGAGACGGATATCGCATCATTCGACAAAAGCC
AAGACGACGCTATGGCGTTAACCGGTCTGATGATCTTGGAGGACCTGGGTGTGGATCAACCACTACTCGACTTGA
TCGAGTGCGCCTTTGGAGAAATATCATCCACCCATCTACCTACGGGTACTCGTTTTAAATTCGGGGCGATGATGA
AATCCGGAATGTTCCTCACACTTTTTGTCAACACAGTTTTGAATGTCGTTATCGCCAGCAGAGTACTAGAAGAGC
GGCTTAAAACGTCCAGATGTGCAGCGTTCATTGGCGACGACAACATCATACATGGAGTAGTATCTGACAAAGAAA
TGGCTGAGAGGTGCGCCACCTGGCTCAACATGGAGGTTAAGATCATCGACGCAGTCATCGGTGAGAGACCACCTT
ACTTCTGCGGCGGATTTATCTTGCAAGATTCGGTTACTTCCACAGCGTGCCGCGTGGCGGACCCctgaaaaggc
tgtttaagttgggtaaaccgctcccagccgacgacgagcaagacgaagacagaagacgcgctctgctagatgaaa
caaaggcgtggtttagagtaggtataacaggcactttagcagtggccgtgacgacccggtatgaggtagacaata
ttacacctgtcctactggcattgagaactttgcccagagcaaaagagcattccaagccatcagaggggaaataa
agcatctctacggtggtcctaaatagtcagcatagtacatttcatctgactaatactacaacaccaccaccatga
atagaggattctttaacatgctcggccgccgccccttcccggcccccactgccatgtggaggccgcggAGAAGGA
GGCAGGCGGCCCCGATGCCTGCCCGCAACGGGCTGGCTTCTCAAATCCAGCAACTGACCACAGCCGTCAGTGCCC
TAGTCATTGGACAGGCAACTAGACCTCAACCCCCACGTCCACGCCCGCCACCGCGCCAGAAGAAGCAGGCGCCCA
AGCAACCACCGAAGCCGAAGAAACCAAAAACGCAGGAGAAGAAGAAGCAACCTGCAAAACCCAAACCCGGAA
AGAGACAGCGCATGGCACTTAAGTTGGAGGCCGACAGATCGTTCGACGTCAAGAACGAGGACGGAGATGTCATCG
GCACGCACTGGCCATGGAAGGAAAGGTAATGAAACCTCTGACACGTGAAAGGAACCATCGACCACCCTGTGCTAT
CAAAGCTCAAATTTACCAAGTCGTCAGCATACGACATGGAGTTCGCACAGTTGCCAGTCAACATGAGAAGTGAGG
CATTCACCTACACCAGTGAACACCCCGAAGGATTCTATAACTGGCACCACGGAGCGGTGCAGTATAGTGGAGGTA
GATTTACCATCCCTCGCGGAGTAGGAGGCAGAGGAGACAGCGGTCGTCCGATCATGGATAACTCCGGTCgGGTTG
```

FIG. 2B-2

```
TCGCGATAGTCCTCGGTGGAGCTGATGAAGGAACACGAACTGCCCTTTCGGTCGTCACCTGGAATAGTAAAGGGA
AGACAATTAAGACGACCCCGGAAGGGACAGAAGAGTGGTCCGCAGCACCACTGGTCACGGCAATGTGTTTGCTCG
GAAATGTGAGCTTCCCATGCGACCGCCCGCCCACATGCTATACCCGCGAACCTTCCAGAGCCCTCGACATCCTTG
AAGAGAACGTGAACCATGAGGCCTACGATACCCTGCTCAATGCCATATTGCGGTGCGGATCGTCTGGCAGAAGCA
AAAGAAGCGTCACTGACGACTTTACCCTGACCAGCCCCTACTTGGGCACATGCTCGTACTGCCACCATACTGAAC
CGTGCTTCAGCCCTGTTAAGATCGAGCAGGTCTGGGACGAAGCGGACGATAACACCATACGCATACAGACTTCCG
CCCAGTTTGGATACGACCAAAGCGGAGCAGCAAGCGCAAACAAGTACCGCTACATGTCGCTTAAGCAGGATCACA
CCGTTAAAGAAGGCACCATGGATGACATCAAGATTAGCACCTCAGGACCGTGTAGAAGGCTTAGCTACAAAGGAT
ACTTTCTCCTCGCAAAATGCCCTCCAGGGGACAGCGTAACGGTTAGCATAGTGAGTAGCAACTCAGCAACGTCAT
GTACACTGGCCCGCAAGATAAAACCAAAATTCGTGGGACGGGAAAAATATGATCTACCTCCCGTTCACGGTAAAA
AAATTCCTTGCACAGTGTACGACCGTCTGAAAGGAACAACTGCAGGCTACATCACTATGCACAGGCCGGGACCGC
ACGCTTATACATCCTACCTGGAAGAATCATCAGGGAAAGTTTACGCAAAGCCGCCATCTGGGAAGAACATTACGT
ATGAGTGCAAGTGCGGCGACTACAAGACCAGAACCGTTTCGACCCGCACCGAAATCACTGGTTGCACCGCCATCA
AGCAGTGCGTCGCCTATAAGAGCGACCAAACGAAGTGGGTCTTCAACTCACCGGACTTGATCAGACATGACGACC
ACACGGCCCAAGGGAAATTGCATTTGCCTTTCAAGTTGATCCCGAGTACCTGCATGGTCCCTGTTGCCCACGCGC
CGAATGTAATACATGGCTTTAAACACATCAGCCTCCAATTAGATACAGACCACTTGACATTGCTCACCACCAGGA
GACTAGGGGCAAACCCGGAACCAACCACTGAATGGATCGTCGGAAAGACGGTCAGAAACTTCACCGTCGACCGAG
ATGGCCTGGAATACATATGGGGAAATCATGAGCCAGTGAGGGTCTATGCCCAAGAGTCAGCACCAGGAGACCCTC
ACGGATGGCCACACGAAATAGTACAGCATTACTACCATCGCCATCCTGTGTACACCATCTTAGCCGTCGCATCAG
CTACCGTGGCGATGATGATTGGCGTAACTGTTGCAGTGTTATGTGCCTGTAAAGCGCGCCGTGAGTGCCTGACGC
CATACGCCCTGGCCCCAAACGCCGTAATCCCAACTTCGCTGGCACTCTTGTGCTGCGTTAGGTCGGCCAATGCTG
AAACGTTCACCGAGACCATGAGTTACTTGTGGTCGAACAGTCAGCCGTTCTTCTGGGTCCAGTTGTGCATACCTT
TGGCCGCTTTCATCGTTCTAATGCGCTGCTGCTCCTGCTGCCTGCCTTTTTTAGTGGTTGCCGGCGCCTACCTGG
CGAAGGTAGACGCCTACGAACATGCGACCACTGTTCCAAATGTGCCACAGATACCGTATAAGGCACTTGTTGAAA
GGGCAGGGTATGCCCCGCTCAATTTGGAGATCACTGTCATGTCCTCGGAGGTTTTGCCTTCCACCAACCAAGAGT
ACATTACCTGCAAATTCACCACTGTGGTCCCTCCCCAAAAATCAAATGCTGCGGCTCCTTGGAATGTCAGCCGG
CCGTTCATGCAGACTATACCTGCAAGGTCTTCGGAGGGGTCTACCCCTTTATGTGGGGAGGAGCGCAATGTTTTT
GCGACAGTGAGAACAGCCAGATGAGTGAGGCGTACGTCGAACTGTCAGCAGATTGCGCGTCTGACCACGCGCAGG
CGATTAAGGTGCACACTGCCGCGATGAAAGTAGGACTGCGTATAGTGTACGGGAACACTACCAGTTTCCTAGATG
TGTACGTGAACGGAGTCACACCAGGAACGTCTAAAGACTTGAAAGTCATAGCTGGACCAATTTCAGCATCGTTTA
CGCCATTCGATCATAAGGTCGTTATCCATCGCGGCCTGGTGTACAACTATGACTTCCCGGAATATGGAGCGATGA
AACCAGGAGCGTTTGGAGACATTCAAGCTACCTCCTTGACTAGCAAGGATCTCATCGCCAGCACAGACATTAGGC
TACTCAAGCCTTCCGCCAAGAACGTGCATGTCCCGTACACGCAGGCCGCATCAGGATTTGAGATGTGGAAAAACA
ACTCAGGCCGCCCACTGCAGGAAACCGCACCTTTCGGGTGTAAGATTGCAGTAAATCCGCTCCGAGCGGTGGACT
GTTCATACGGGAACATTCCCATTTCTATTGACATCCCGAACGCTGCCTTTATCAGGACATCAGATGCACCACTGG
TCTCAACAGTCAAATGTGAAGTCAGTGAGTGCACTTATTCAGCAGACTTCGGCGGGATGGCCACCCTGCAGTATG
TATCCGACCGCGAAGGTCAATGCCCCGTACATTCGCATTCGAGCACAGCAACTCTCCAAGAGTCGACAGTACATG
TCCTGGAGAAAGGAGCGGTGACAGTACACTTTAGCACCGCGAGTCCACAGGCGAACTTTATCGTATCGCTGTGTG
GGAAGAAGACAACATGCAATGCAGAATGTAAACCACCAGCTGACCATATCGTGAGCACCCCGCACAAAAATGACC
AAGAATTTCAAGCCGCCATCTCAAAAACATCATGGAGTTGGCTGTTTGCCCTTTTCGGCGGCGCCTCGTCGCTAT
TAATTATAGGACTTATGATTTTTGCTTGCAGCATGATGCTGACTAGCACACGAAGATGACCGCTACGCCCAATG
ATCCGACCAGCAAAACTCGATGTACTTCCGAGGAACTGATGTGCATAATGCATcaggctggtacattagatcccc
gcttaccgcgggcaatatagcaacactaaaaactcgatgtacttccgaggaagcgcagtgcataatgctgcgcag
tgttgccacataaccactatattaaccatttatctagcggacgccaaaaactcaatgtatttctgaggaagcgtg
gtgcataatgccacgcagcgtctgcataactttttattatttcttttattaatcaacaaaatttgtttttaacat
ttc
```

FIG. 2B-3

```
ATTGACGGCGTAGTACACACTATTGAATCAAACAGCCGACCAATTGCACTACCATCACAATGGAGAAGCCAGTAG
TAAACGTAGACGTAGACCCCCAGAGTCCGTTTGTCGTGCAACTGCAAAAAAGCTTCCCGCAATTTGAGGTAGTAG
CACAGCAGGTCACTCCAAATGACCATGCTAATGCCAGAGCATTTTCGCATCTGGCCAGTAAACTAATCGAGCTGG
AGGTTCCTACCACAGCGACGATCTTGGACATAGGCAGCGCACCGGCTCGTAGAATGTTTTCCGAGCACCAGTATC
ATTGTGTCTGCCCCATGCGTAGTCCAGAAGACCCGGACCGCATGATGAAATATGCCAGTAAACTGGCGGAAAAAG
CGTGCAAGATTACAAACAAGAACTTGCATGAAGATTAAGGATCTCCGGACCGTACTTGATACGCCGGATGCTG
AAACACCATCGCTCTGCTTTCACAACGATGTTACCTGCAACATGCGTGCCGAATATTCCGTCATGCAGGACGTGT
ATATCAACGCTCCCGGAACTATCTATCATCAGGCTATGAAAGGCGTGCGGACCCTGTACTGGATTGGCTTCGACA
CCACCCAGTTCATGTTCTCGGCTATGGCAGGTTCGTACCCTGCGTACAACACCAACTGGGCCGACGAGAAAGTCC
TTGAAGCGCGTAACATCGGACTTTGCAGCACAAAGCTGAGTGAAGGTAGGACAGGAAAATTGTCGATAATGAGGA
AGAAGGAGTTGAAGCCCGGGTCGCGGGTTTATTTCTCCGTAGGATCGACACTTTATCCAGAACACAGAGCCAGCT
TGCAGAGCTGGCATCTTCCATCGGTGTTCCACTTGAATGGAAAGCAGTCGTACACTTGCCGCTGTGATACAGTGG
TGAGTTGCGAAGGCTACGTAGTGAAGAAAATCACCATCAGTCCCGGGATCACGGGAGAAACCGTGGGATACGCGG
TTACACACAATAGCGAGGGCTTCTTGCTATGCAAAGTTACTGACACAGTAAAAGGAGAACGGGTATCGTTCCCTG
TGTGCACGTACATCCCGGCCACCATATGCGATCAGATGACTGGTATAATGGCCACGGATATATCCCTGACGATG
CACAAAAACTTCTGGTTGGGCTCAACCAGCGAATTGTCATTAACGGTAGGACTAACAGGAACACCAACACCATGC
AAAATTACCTTCTGCCGATCATAGCACAAGGGTTCAGCAAATGGGCTAAGGAGCGCAAGGATGATCTTGATAACG
AGAAAATGCTGGGTACTAGAGAACGCAAGCTTACGTACGGCTGCTTGTGGGCGTTTCGCACTAAGAAAGTACATT
CGTTTTATCGCCCACCTGGAACGCAGACCATCGTAAAAGTCCCAGCCTCTTTTAGCGCTTTTCCCATGTCGTCCG
TATGGACGACCTCTTTGCCCATGTCGCTGAGGCAGAAATTGAAACTGGCATTGCAACCAAAGAAGGAGGAAAAAC
TGCTGCAGGTCTCGGAGGAATTAGTCATGGAGGCCAAGGCTGCTTTTGAGGATGCTCAGGAGGAAGCCAGAGCGG
AGAAGCTCCGAGAAGCACTTCCACCATTAGTGGCAGACAAAGGCATCGAGGCAGCCGCAGAAGTTGTCTGCGAAG
TGGAGGGGCTCCAGGCGGACATCGGAGCAGCATTAGTTGAAACCCCGCGCGGTCACGTAAGGATAATACCTCAAG
CAAATGACCGTATGATCGGACAGTATATCGTTGTCTCGCCAAACTCTGTGCTGAAGAATGCCAAACTCGCACCAG
CGCACCCGCTAGCAGATCAGGTTAAGATCATAACACACTCCGGAAGATCAGGAAGGTACGCGGTCGAACCATACG
ACGCTAAAGTACTGATGCCAGCAGGAGGTGCCGTACCATGGCCAGAATTCCTAGCACTGAGTGAGAGCGCCACGT
TAGTGTACAACGAAAGAGAGTTTGTGAACCGCAAACTATACCACATTGCCATGCATGGCCCCGCCAAGAATACAG
AAGAGGAGCAGTACAAGGTTACAAAGGCAGAGCTTGCAGAAACAGAGTACGTGTTTGACGTGGACAAGAAGCGTT
GCGTTAAGAAGGAAGAAGCCTCAGGTCTGTTCCTCTCGGGAGAACTGACCAACCCTCCCTATCATGAGCTAGCTC
TGGAGGGACTGAAGACCCGACCTGCGGTCCCGTACAAGGTCGAAACAATAGGAGTGATAGGCACACCGGGGTCGG
GCAAGTCAGCTATTATCAAGTCAACTGTCACGGCACGAGATCTTGTTACCAGCGGAAAGAAAGAAAATTGTCGCG
AAATTGAGGCCGACGTGCTAAGACTGAGGGGTATGCAGATTACGTCGAAGACAGTAGATTCGGTTATGCTCAACG
GATGCCACAAAGCCGTAGAAGTGCTGTACGTTGACGAAGCGTTCGCGTGCCACGCAGGAGCACTACTTGCCTTGA
TTGCTATCGTCAGGCCCCGCAAGAAGGTAGTACTATGCGGAGACCCCATGCAATGCGGATTCTTCAACATGATGC
AACTAAAGGTACATTTCAATCACCCTGAAAAAGACATATGCACCAAGACATTCTACAAGTATATCTCCCGGCGTT
GCACACAGCCAGTTACAGCTATTGTATCGACACTGCATTACGATGGAAAGATGAAAACCACGAACCCGTGCAAGA
AGAACATTGAAATCGATATTACAGGGGCCACAAAGCCGAAGCCAGGGGATATCATCCTGACATGTTTCCGCGGGT
GGGTTAAGCAATTGCAAATCGACTATCCCGGACATGAAGTAATGACAGCCGCGGCCTCACAAGGGCTAACCAGAA
AAGGAGTGTATGCCGTCCGGCAAAAAGTCAATGAAAACCCACTGTACGCGATCACATCAGAGCATGTGAACGTGT
TGCTCACCCGCACTGAGGACAGGCTAGTGTGGAAAACCTTGCAGGGCGACCCATGGATTAAGCAGCTCACTAACA
TACCTAAAGGAAACTTTCAGGCTACTATAGAGGACTGGGAAGCTGAACACAAGGGAATAATTGCTGCAATAAACA
GCCCCACTCCCCGTGCCAATCCGTTCAGCTGCAAGACCAACGTTTGCTGGGCGAAAGCATTGGAACCGATACTAG
CCACGGCCGGTATCGTACTTACCGGTTGCCAGTGGAGCGAACTGTTCCCACAGTTTGCGGATGACAAACCACATT
CGGCCATTTACGCCTTAGACGTAATTTGCATTAAGTTTTTCGGCATGGACTTGACAAGCGGACTGTTTTCTAAAC
AGAGCATCCCACTAACGTACCATCCCGCCGATTCAGCGAGGCCGGTAGCTCATTGGGACAACAGCCCAGGAACCC
GCAAGTATGGGTACGATCACGCCATTGCCGCCGAACTCTCCCGTAGATTTCCGGTGTTCCAGCTAGCTGGGAAGG
GCACACAACTTGATTTGCAGACGGGGAGAACCAGAGTTATCTCTGCACAGCATAACCTGGTCCCGGTGAACCGCA
ATCTTCCTCACGCCTTAGTCCCCGAGTACAAGGAGAAGCAACCCGGCCCGGTCGAAAAATTCTTGAACCAGTTCA
AACACCACTCAGTACTTGTGGTATCAGAGGAAAAAATTGAAGCTCCCCGTAAGAGAATCGAATGGATCGCCCCGA
TTGGCATAGCCGGTGCAGATAAGAACTACAACCTGGCTTTCGGGTTTCCGCCGCAGGCACGGTACGACCTGGTGT
TCATCAACATTGGAACTAAATACAGAAACCACCACTTTCAGCAGTGCGAAGACCATGCGGCGACCTTAAAAACCC
TTTCGCGTTCGGCCCTGAATTGCCTTAACCCAGGAGGCACCCTCGTGGTGAAGTCCTATGGCTACGCCGACCGCA
ACAGTGAGGACGTAGTCACCGCTCTTGCCAGAAAGTTTGTCAGGGTGTCTGCAGCGAGACCAGATTGTGTCTCAA
```

FIG. 2C-1

```
GCAATACAGAAATGTACCTGATTTTCCGACAACTAGACAACAGCCGTACACGGCAATTCACCCCGCACCATCTGA
ATTGCGTGATTTCGTCCGTGTATGAGGGTACAAGAGATGGAGTTGGAGCCGCGCCGTCATACCGCACCAAAAGGG
AGAATATTGCTGACTGTCAAGAGGAAGCAGTTGTCAACGCAGCCAATCCGCTGGGTAGACCAGGCGAAGGAGTCT
GCCGTGCCATCTATAAACGTTGGCCGACCAGTTTTACCGATTCAGCCACGGAGACAGGCACCGCAAGAATGACTG
TGTGCCTAGGAAAGAAAGTGATCCACGCGGTCGGCCCTGATTTCCGGAAGCACCCAGAAGCAGAAGCCTTGAAAT
TGCTACAAAACGCCTACCATGCAGTGGCAGACTTAGTAAATGAACATAACATCAAGTCTGTCGCCATTCCACTGC
TATCTACAGGCATTTACGCAGCCGGAAAAGACCGCCTTGAAGTATCCACTTAACTGCTTGACAACCGCGCTAGACA
GAACTGACGCGGACGTAACCATCTATTGCCTGGATAAGAAGTGGAAGGAAAGAATCGACGCGGCACTCCAACTTA
AGGAGTCTGTAACAGAGCTGAAGGATGAAGATATGGAGATCGACGATGAGTTAGTATGGATCCATCCAGACAGTT
GCTTGAAGGGAAGAAAGGGATTCAGTACTACAAAAGGAAAATTGTATTCGTACTTCGAAGGCACCAAATTCCATC
AAGCAGCAAAAGACATGGCGGAGATAAAGGTCCTGTTCCCTAATGACCAGGAAAGTAATGAACAACTGTGTGCCT
ACATATTGGGTGAGACCATGGAAGCAATCCGCGAAAAGTGCCCGGTCGACCATAACCCGTCGTCTAGCCCGCCCA
AAACGTTGCCGTGCCTTTGCATGTATGCCATGACGCCAGAAAGGGTCCACAGACTTAGAAGCAATAACGTCAAAG
AAGTTACAGTATGCTCCTCCACCCCCCTTCCTAAGCACAAAATTAAGAATGTTCAGAAGGTTCAGTGCACGAAAG
TAGTCCTGTTTAATCCGCACACTCCCGCATTCGTTCCCGCCCGTAAGTACATAGAAGTGCCAGAACAGCCTACCG
CTCCTCCTGCACAGGCCGAGGAGGCCCCCGAAGTTGTAGCGACACCGTCACCATCTACAGCTGATAACACCTCGC
TTGATGTCACAGACATCTCACTGGATATGGATGACAGTAGCGAAGGCTCACTTTTTTCGAGCTTTAGCGGATCGG
ACAACTCTATTACTAGTATGGACAGTTGGTCGTCAGGACCTAGTTCACTAGAGATAGTAGACCGAAGGCAGGTGG
TGGTGGCTGACGTTCATGCCGTCCAAGAGCCTGCCCCTATTCCACCGCCAAGGCTAAAGAAGATGGCCCGCCTGG
CAGCGGCTAGAAAAGAGCCCACTCCACCGGCAAGCAATAGCTCTGAGTCCCTCCACCTCTCTTTTGGTGGGGTAT
CCATGTCCCTCGGATCAATTTTCGACGGAGAGACGGCCCGCCAGGCAGCGGTACAACCCCTGGCAACAGGCCCCA
CGGATGTGCCTATGTCTTTCGGATCGTTTTCCGACGGAGAGATTGATGAGCTGAGCCGCAGAGTAACTGAGTCCG
AACCCGTCCTGTTTGGATCATTTGAACCGGGCGAAGTGAACTCAATTATATCGTCCCGATCAGCCGTATCTTTTC
CACTACGCAAGCAGAGACGTAGACGCAGGAGCAGGAGGACTGAATACTGACTAACCGGGGTAGGTGGGTACATAT
TTTCGACGGACACAGGCCCTGGGCACTTGCAAAAGAAGTCCGTTCTGCAGAACCAGCTTACAGAACCGACCTTGG
AGCGCAATGTCCTGGAAAGAATTCATGCCCCGGTGCTCGACACGTCGAAAGAGGAACAACTCAAACTCAGGTACC
AGATGATGCCCACCGAAGCCAACAAAAGTAGGTACCAGTCTCGTAAAGTAGAAAATCAGAAAGCCATAACCACTG
AGCGACTACTGTCAGGACTACGACTGTATAACTCTGCCACAGATCAGCCAGAATGCTATAAGATCACCTATCCGA
AACCATTGTACTCCAGTAGCGTACCGGCGAACTACTCCGATCCACAGTTCGCTGTAGCTGTCTGTAACAACTATC
TGCATGAGAACTATCCGACAGTAGCATCTTATCAGATTACTGACGAGTACGATGCTTACTTGGATATGGTAGACG
GGACAGTCGCCTGCCTGGATACTGCAACCTTCTGCCCCGCTAAGCTTAGAAGTTACCCGAAAAAACATGAGTATA
GAGCCCCGAATATCCGCAGTGCGGTTCCATCAGCGATGCAGAACACGCTACAAAATGTGCTCATTGCCGCAACTA
AAAGAAATTGCAACGTCACGCAGATGCGTGAACTGCCAACACTGGACTCAGCGACATTCAATGTCGAATGCTTTC
GAAAATATGCATGTAATGACGAGTATTGGGAGGAGTTCGCTCGGAAGCCAATTAGGATTACCACTGAGTTTGTCA
CCGCATATGTAGCTAGACTGAAAGGCCCTAAGGCCGCCGCACTATTTGCAAAGACGTATAATTTGGTCCCATTGC
AAGAAGTGCCTATGGATAGATTCGTCATGGACATGAAAAGGGACGTGAAAGTTACACCAGGCACGAAACACACAG
AAGAAAGACCGAAAGTACAAGTGATACAAGCCGCAGAACCCCTGGCGACTGCTTACTTATGCGGGATTCACCGGG
AATTAGTGCGTAGGCTTACGGCCGTCTTGCTTCCAAACATTCACACGCTTTTTGACATGTCGGCGGAGGATTTTG
ATGCAATCATAGCAGAACACTTCAAGCAAGGCGACCCGGTACTGGAGACGGATATCGCATCATTCGACAAAAGCC
AAGACGACGCTATGGCGTTAACCGGTCTGATGATCTTGGAGGACCTGGGTGTGGATCAACCACTACTCGACTTGA
TCGAGTGCGCCTTTGGAGAAATATCATCCACCCATCTACCTACGGGTACTCGTTTTAAATTCGGGGCGATGATGA
AATCCGGAATGTTCCTCACACTTTTTGTCAACACAGTTTTGAATGTCGTTATCGCCAGCAGAGTACTAGAAGAGC
GGCTTAAAACGTCCAGATGTGCAGCGTTCATTGGCGACGACAACATCATACATGGAGTAGTATCTGACAAAGAAA
TGGCTGAGAGGTGCGCCACCTGGCTCAACATGGAGGTTAAGATCATCGACGCAGTCATCGGTGAGAGACCACCTT
ACTTCTGCGGCGGATTTATCTTGCAAGATTCGGTTACTTCCACAGCGTGCCGCGTGGCGGACCCctgaaaaggc
tgtttaagttgggtaaaccgctcccagccgacgacgagcaagacgaagacagaagacgcgctctgctagatgaaa
caaaggcgtggtttagagtaggtataacaggcactttagcagtggccgtgacgacccggtatgaggtagacaata
ttacacctgtcctactggcattgagaacttttgcccagagcaaaagagcattccaagccatcagaggggaaataa
agcatctctacggtggtcctaaatagtcagcatagtacatttcatctgactaatactacaacaccaccaccatga
atagaggattctttaacatgctcggccgcgcccttccggcccccactgccatgtggaggccgcggAGAAGGA
GGCAGGCGGCCCCGATGCCTGCCCGCAACGGGCTGGCTTCTCAAATCCAGCAACTGACCACAGCCGTCAGTGCCC
TAGTCATTGGACAGGCAACTAGACCTCAACCCCACGTCCACGCCCGCCACCGCGCCAGAAGAAGCAGGCGCCCA
AGCAACCACCGAAGCCGAAGAAACCAAAAACGCAGGAGAAGAAGAAGAAGCAACCTGCAAAACCCAAACCCGGAA
AGAGACAGCGCATGGCACTTAAGTTGGAGGCCGACAGATCGTTCGACGTCAAGAACGAGGACGGAGATGTCATCG
GCACGCACTGGCCATGGAAGGAAAGGTAATGAAACCTCTGCACGTGAAAGGAACCATCGACCACCCTGTGCTAT
CAAAGCTCAAATTTACCAAGTCGTCAGCATACGACATGGAGTTCGCACAGTTGCCAGTCAACATGAGAAGTGAGG
CATTCACCTACACCAGTGAACACCCCGAAGGATTCTATAACTGGCACCACGGAGCGGTGCAGTATAGTGGAGGTA
GATTTACCATCCCTCGCGGAGTAGGAGGCAGAGGAGACAGCGGTCGTCCGATCATGGATAACTCCGGTCgGGTTG
```

FIG. 2C-2

```
TCGCGATAGTCCTCGGTGGAGCTGATGAAGGAACACGAACTGCCCTTTCGGTCGTCACCTGGAATAGTAAAGGGA
AGACAATTAAGACGACCCCGGAAGGGACAGAAGAGTGGTCCGCAGCACCACTGGTCACGGCAATGTGTTTGCTCG
GAAATGTGAGCTTCCCATGCGACCGCCCGCCCACATGCTATACCCGCGAACCTTCCAGAGCCCTCGACATCCTTG
AAGAGAACGTGAACCATGAGGCCTACGATACCCTGCTCAATGCCATATTGCGGTGCGGATCGTCTGGCAGAAGCA
AAAGAAGCGTCACTGACGACTTTACCCTGACCAGCCCCTACTTGGGCACATGCTCGTACTGCCACCATACTGAAC
CGTGCTTCAGCCCTGTTAAGATCGAGCAGGTCTGGGACGAAGCGGACGATAACACCATACGCATACAGACTTCCG
CCCAGTTTGGATACGACCAAAGCGGAGCAGCAAGCGCAAACAAGTACCGCTACATGTCGCTTAAGCAGGATCACA
CCGTTAAAGAAGGCACCATGGATGACATCAAGATTAGCACCTCAGGACCGTGTAGAAGGCTTAGCTACAAAGGAT
ACTTTCTCCTCGCAAAATGCCCTCCAGGGGACAGCGTAACGGTTAGCATAGTGAGTAGCAACTCAGCAACGTCAT
GTACACTGGCCCGCAAGATAAAACCAAAATTCGTGGGACGGGAAAAATATGATCTACCTCCCGTTCACGGTAAAA
AAATTCCTTGCACAGTGTACGACCGTCTGAAAGGAACAACTGCAGGCTACATCACTATGCACAGGCCGGGACCGC
ACGCTTATACATCCTACCTGGAAGAATCATCAGGGAAAGTTTACGCAAAGCCGCCATCTGGGAAGAACATTACGT
ATGAGTGCAAGTGCGGCGACTACAAGACCAGAACCGTTTCGACCCGCACCGAAATCACTGGTTGCACCGCCATCA
AGCAGTGCGTCGCCTATAAGAGCGACCAAACGAAGTGGGTCTTCAACTCACCGGACTTGATCAGACATGACGACC
ACACGGCCCAAGGGAAATTGCATTTGCCTTTCAAGTTGATCCCGAGTACCTGCATGGTCCCTGTTGCCCACGCGC
CGAATGTAATACATGGCTTTAAACACATCAGCCTCCAATTAGATACAGACCACTTGACATTGCTCACCACCAGGA
GACTAGGGGCAAACCCGGAACCAACCACTGAATGGATCGTCGGAAAGACGGTCAGAAACTTCACCGTCGACCGAG
ATGGCCTGGAATACATATGGGGAAATCATGAGCCAGTGAGGGTCTATGCCCAAGAGTCAGCACCAGGAGACCCTC
ACGGATGGCCACACGAAATAGTACAGCATTACTACCATCGCCATCCTGTGTACACCATCTTAGCCGTCGCATCAG
CTACCGTGGCGATGATGATTGGCGTAACTGTTGCAGTGTTATGTGCCTGTAAAGCGCGCCGTGAGTGCCTGACGC
CATACGCCCTGGCCCCAAACGCCGTAATCCCAACTTCGCTGGCACTCTTGTGCTGCGTTAGGTCGGCCAATGCTG
AAACGTTCACCGAGACCATGAGTTACTTGTGGTCGAACAGTCAGCCGTTCTTCTGGGTCCAGTTGTGCATACCTT
TGGCCGCTTTCATCGTTCTAATGCGCTGCTGCTCCTGCTGCCTGCCTTTTTTAGTGGTTGCCGGCGCCTACCTGG
CGAAGGTAGACGCCTACGAACATGCGACCACTGTTCCAAATGTGCCACAGATACCGTATAAGGCACTTGTTGAAA
GGGCAGGGTATGCCCCGCTCAATTTGGAGATCACTGTCATGTCCTCGGAGGTTTTGCCTTCCACCAACCAAGAGT
ACATTACCTGCAAATTCACCACTGTGGTCCCCTCCCCAAAAATCAAATGCTGCGGCTCCTTGGAATGTCAGCCGG
CCGTTCATGCAGACTATACCTGCAAGGTCTTCGGAGGGGTCTACCCCTTTATGTGGGGAGGAGCGCAATGTTTTT
GCGACAGTGAGAACAGCCAGATGAGTGAGGCGTACGTCGAACTGTCAGCAGATTGCGCGTCTGACCACGCGCAGG
CGATTAAGGTGCACACTGCCGCGATGAAAGTAGGACTGCGTATAGTGTACGGGAACACTACCAGTTTCCTAGATG
TGTACGTGAACGGAGTCACACCAGGAACGTCTAAAGACTTGAAAGTCATAGCTGGACCAATTTCAGCATCGTTTA
CGCCATTCGATCATAAGGTCGTTATCCATCGCGGCCTGGTGTACAACTATGACTTCCCGGAATATGGAGCGATGA
AACCAGGAGCGTTTGGAGACATTCAAGCTACCTCCTTGACTAGCAAGGATCTCATCGCCAGCACAGACATTAGGC
TACTCAAGCCTTCCGCCAAGAACGTGCATGTCCCGTACACGCAGGCCGCATCAGGATTTGAGATGTGGAAAAACA
ACTCAGGCCGCCCACTGCAGGAAACCGCACCTTTCGGGTGTAAGATTGCAGTAAATCCGCTCCGAGCGGTGGACT
GTTCATACGGGAACATTCCCATTTCTATTGACATCCCGAACGCTGCCTTTATCAGGACATCAGATGCACCACTGG
TCTCAACAGTCAAATGTGAAGTCAGTGAGTGCACTTATTCAGCAGACTTCGGCGGGATGGCCACCCTGCAGTATG
TATCGACCGCGAAGGTCAATGCCCCGTACATTCGCATTCGAGCACGACAACTCTCCAAGAGTCGACAGTACATG
TCCTGGAGAAAGGAGCGGTGACAGTACACTTTAGCACCGCGAGTCCACAGGCGAACTTTATCGTATCGCTGTGTG
GGAAGAAGACAACATGCAATGCAGAATGTAAACCACCAGCTGACCATATCGTGAGCACCCCGCACAAAAATGACC
AAGAATTTCAAGCCGCCATCTCAAAAACATCATGGAGTTGGCTGTTTGCCCTTTTCGGCGGCGCCTCGTCGCTAT
TAATTATAGGACTTATGATTTTTGCTTGCAGCATGATGCTGACTAGCACACGAAGATGACCGCTACGCCCAATG
ATCCGACCAGCAAAACTCGATGTACTTCCGAGGAACTGATGTGCATAATGCATcaggctggtacattagatcccc
gcttaccgcgggcaatatagcaacactaaaaactcgatgtacttccgaggaagcgcagtgcataatgctgcgcag
tgttgccacataaccactatattaaccatttatctagcggacgccaaaaactcaatgtatttctgaggaagcgtg
gtgcataatgccacgcagcgtctgcataactttattatttcttttattaatcaacaaaattttgttttttaacat
ttc
```

Trafficking of alphavirus vector transduced DC to the mandibular lymph node

GF  rhodamine  Dual x20

SIN-GFP vector injected intradermally, with rhodamine paint applied to skin

COMPOSITIONS AND METHODS FOR GENERATING AN IMMUNE RESPONSE UTILIZING ALPHAVIRUS-BASED VECTOR SYSTEMS

CROSS-REFERENCE TO RELATED APPLICATIONS

This application is a continuation of U.S. application Ser. No. 09/551,977, filed Apr. 14, 2000 now abandoned, which claims the benefit of U.S. Provisional Application Nos. 60/191,363, filed Mar. 22, 2000; 60/148,086, filed Aug. 9, 1999; and 60/129,498, filed Apr. 14, 1999, each of which is incorporated herein by reference in its entirety.

TECHNICAL FIELD

The present invention relates generally to gene-based vaccines and therapeutics; and more specifically, to compositions and methods that increase the efficiency of alphavirus-based vector systems used for such vaccines and therapeutics.

BACKGROUND OF THE INVENTION

Alphaviruses comprise a group of genetically, structurally, and serologically related arthropod-borne viruses of the Togaviridae family. These viruses are distributed worldwide, and persist in nature through a mosquito to vertebrate cycle. Birds, rodents, horses, primates, and humans are among the identified alphavirus vertebrate reservoir/hosts.

Twenty-six known viruses and virus subtypes have been classified within the alphavirus genus utilizing the hemagglutination inhibition (HI) assay. This assay segregates the 26 alpha viruses into three major complexes: the Venezuelan equine encephalitis (VEE) complex, the Semliki Forest (SF) complex, and the western equine encephalitis (WEE) complex. In addition, four other viruses, eastern equine encephalitis (EEE), Barmah Forest, Middelburg, and Ndumu, receive individual classification based on the HI serological assay.

Members of the alphavirus genus also are further classified into one of two groups, according to the clinical symptoms they exhibit as a result of infection in humans. The first group is alphaviruses associated primarily with encephalitis, and the second group is alphaviruses associated primarily with fever, rash, and polyarthritis. Included in the first group are the VEE and WEE complexes, and EEE. In general, infection with this group can result in permanent sequalae, including death. In the second group is the SF complex, comprised of the individual alphaviruses Semliki Forest, Sindbis, Ross River, Chikungunya, O'nyong-nyong, and Mayaro. Although serious epidemics have been reported, infection by viruses of this group is generally self-limiting, without permanent sequalae.

Sindbis virus is the prototype member of the *Alphavirus* genus of the Togaviridae family. Its replication strategy is well characterized and serves as a model for other alphaviruses (Strauss and Strauss, *Microbio. Rev.* 58:491-562, 1994). The genome of Sindbis virus (like other alphaviruses) is an approximately 12 kb single-stranded, positive-sense RNA molecule that is capped and polyadenylated. Genome RNA is contained within a virus-encoded capsid protein shell which is, in turn, surrounded by a host-derived lipid envelope from which two viral-specific glycoproteins, E1 and E2, protrude as spikes from the virion surface. Certain alphaviruses (e.g., SF) also maintain an additional protein, E3, which is a cleavage product from the E2 precursor protein, PE2.

After virus particle absorption to target cells, penetration, and uncoating of the nucleocapsid to release viral genomic RNA into the cytoplasm, the replication process is initiated by translation of four nonstructural replicase proteins (nsP1-nsP4) from the 5' two-thirds of the viral genome. The four nsPs are translated as one of two polyproteins (nsP123 or nsP1234), and processed post-translationally into mature monomeric proteins by an active protease in the C-terminal domain of nsP2. Both of the nonstructural polyproteins and their derived monomeric units may participate in the RNA replication process, which involves nsP binding to the conserved nucleotide sequence elements (CSEs) present at the 5' and 3' ends, and an internal subgenomic junction region promoter.

The positive strand genome RNA serves as template for the nsP-catalyzed synthesis of a full-length complementary negative strand RNA. Synthesis of the negative strand RNA is catalyzed by binding of a nsP complex to the 3' terminal CSE of the positive strand genome RNA. The negative strand, in turn, serves as template for the synthesis of additional positive strand genome RNA, as well as an abundant subgenomic RNA, initiated internally at the junction region promoter. Synthesis of additional positive strand genome RNA occurs after binding of a nsP complex to the 3' terminal CSE of the complementary negative strand genome-length RNA template. Synthesis of the subgenomic mRNA from the negative-strand RNA template is initiated from the junction region promoter. Thus, the 5' end and junction region CSEs of the positive strand genome RNA are functional only after being transcribed into the negative strand RNA complement (i.e., the 5' end CSE is functional when it is the 3' end of the genomic negative stranded complement).

Alphavirus structural proteins (sPs) are translated from the subgenomic RNA, which represents the 3' one-third of the genome, and like the nsPs, are processed post-translationally into the individual proteins (see FIG. 1). Translation of this subgenomic mRNA produces a single polyprotein consisting of the structural proteins capsid (C) glycoprotein E2 and glycoprotein E1, plus the corresponding leader/signal sequences (E3, 6k) for glycoprotein insertion into the endoplasmic reticulum. The structural gene polyprotein is processed into the mature protein species by a combination of viral (capsid autoprotease) and cellular proteases (e.g., signal peptidase). Alphavirus structural proteins are produced at very high levels due to the abundance of subgenomic mRNA transcribed, as well as the presence of a translational enhancer element (Frolov and Schlesinger, *J. Virol.* 68:8111-8117, 1994; Sjoberg et al., *Bio/Technol.* 12:1127-1131, 1994) within the mRNA, located in the capsid gene coding sequence. Because all structural proteins are synthesized at equimolar ratios, as part of the polyprotein, the translation enhancer element exerts its effect equally on each of the genes.

Several members of the Alphavirus genus are being developed as expression vectors, including, for example, Sindbis virus (Xiong et al., *Science* 243:1188-1191, 1989; Hahn et al., *Proc. Natl. Acad. Sci. USA* 89:2679-2683, 1992; Dubensky et al., *J. Virol.* 70:508-519, 1996), Semliki Forest virus (Liljestrom, *Bio/Technology* 9:1356-1361, 1991), and Venezuelan equine encephalitis virus (Pushko et al., *Virology* 239:389-401, 1997). The general strategy for construction of alphavirus-based expression vectors has been to substitute the viral structural protein genes with a heterologous gene, maintaining transcriptional control via the highly active subgenomic RNA promoter. RNA vectors having this configuration are self-amplifying, and are termed RNA "replicons" and may be synthesized in vitro from cDNA using a bacteriophage promoter (Xiong et al., ibid; Liljestrom et al., ibid; Pushko et al., ibid), or generated in vivo directly from DNA when linked to a eukaryotic promoter (Dubensky et al., ibid; U.S. Pat. No. 5,814,482). Because the vector replicons do not express the alphavirus structural proteins necessary for packaging into recombinant alphavirus particles, these proteins must be provided in trans. One alphavirus, Venezuelan equine encephalitis virus, and its derived recombinant vector particles have been shown to be lymphotropic and infect murine dendritic cells (Caley et al., *J. Virol.* 71:3031-3038, 1997; MacDonald et al., *J. Virol.* 74:914-22, 2000). However, no alphavirus or alphavirus variant was demonstrated to infect human dendritic cells, macrophages or antigen presenting cells.

The present invention discloses novel compositions and methods for generating an enhanced immune response utilizing alphavirus-based vector systems, and further, provides other related advantages.

SUMMARY OF THE INVENTION

Briefly stated, the present invention provides compositions and methods for generating an enhanced immune response utilizing alphavirus-based vector systems. Within one aspect of the present invention, isolated alphaviruses and recombinant alphavirus particles are provided which infect human dendritic cells, (with the proviso that the alphavirus is not ATCC # VR-2526 or said alphavirus particle is not generated in total from ATCC # VR-2526). Within another aspect, isolated alphaviruses and recombinant alphavirus particles are provided which infect non-human dendritic cells (with the proviso that the alphavirus is not a Venezuelan equine encephalitis virus or ATCC # VR-2526, or, that the recombinant alphavirus particle is not derived in total from Venezuelan equine encephalitis virus or ATCC # VR-2526). Within yet another aspect, isolated alphaviruses and recombinant alphavirus particles are provided which infect human macrophages. Within related aspects, isolated alphaviruses and recombinant alphavirus particles are provided which infect human antigen presenting cells, (with the proviso that the alphavirus is not ATCC # VR-2526 or said alphavirus particle is not generated in total from ATCC # VR-2526).

Within certain embodiments of the above, the alphavirus or recombinant alphavirus particle has an amino acid substitution in the E2 glycoprotein as compared to wild-type, for example, at residue 158, 159, 160, 161, or, 162. Within preferred embodiments, the amino acid substitution is at E2 residue 160. Within other embodiments, the alphavirus has an amino acid deletion or insertion in the E2 glycoprotein. Within further embodiments, the alphavirus is a Semliki Forest virus, a Ross River virus, a Venezuelan equine encephalitis virus, a Sindbis virus, or ATCC No. VR-2643. Also provided are nucleic acid molecules which encode the above described alphaviruses (such as, for example, as provided in FIGS. 2B and 2C).

Within other aspects of the present invention alphavirus structural protein expression cassettes are provided, comprising a promoter operably linked to a nucleic acid sequence encoding one or more alphavirus structural proteins from an alphavirus as described above. Within a related aspect, alphavirus structural protein expression cassettes are also provided comprising a promoter operably linked to a nucleic acid sequence encoding alphavirus structural proteins, wherein said nucleic acid sequence comprises a sequence encoding glycoprotein E2, and wherein said sequence encodes a mutation (e.g., a substitution, deletion, or insertion, as compared to wild-type) in the E2 glycoprotein. Within various embodiments, the mutation is a substitution at E2 residue 158, 159, 160, 161, or 162. Within preferred embodiments, the mutation confers to an alphavirus or recombinant alphavirus particle packaged with said E2 glycoprotein the ability to infect human dendritic cells. Within related aspects alphavirus packaging cell lines are provided comprising a host cell and an alphavirus structural protein expression cassette as described above, as well as an alphavirus producer cell line comprising such packaging cells and a vector selected from the group consisting of an alphavirus RNA vector replicon, alphavirus vector construct, and a eukaryotic layered vector initiation system. Further, recombinant alphavirus particles also are provided which can be produced from the above packaging or producer cell lines.

Within yet other aspects of the present invention, methods are provided for introducing a selected sequence into a cell, comprising the step of infecting or otherwise introducing into a cell a recombinant alphavirus particle as described above, such that the selected sequence is introduced into the cell. A wide variety of selected sequences may be introduced into a cell or cells, including for example, heterologous sequences such as proteins (e.g., peptides, antigens, antibodies), and non-protein sequences such as ribozymes. In addition, the recombinant alphavirus particles may be designed to express one or more sequences (e.g., an immune enhancer, cytokine, chemokine, for example, IL-2, IL-10, IL-12, gamma interferon, GM-CSF, MIP3, MIP3, molecules with related function). Further, the recombinant alphavirus particles may be administered utilizing ex vivo or in vivo techniques. Further, within certain embodiments the recombinant alphavirus particles may be utilized with a wide variety of cells, cell populations, or tissues, including for example, a population of cells containing dendritic cells. Within yet further embodiments, the recombinant alphavirus particles may be introduced as a composition, e.g., with enhancers such as cytokines or chemokines (e.g., IL-2, IL-10, IL-12, gamma interferon, GM-CSF), other vectors, or adjuvants.

Within yet further aspects of the invention, alphavirus vector constructs are provided comprising (a) a 5' promoter which initiates synthesis of viral RNA in vitro from cDNA, (b) a 5' sequence which initiates transcription of alphavirus RNA, (c) a nucleic acid molecule which operably encodes all four alphaviral nonstructural proteins, (d) an alphavirus RNA polymerase recognition sequence; and (e) a 3'polyadenylate tract, wherein the nucleic acid sequence which operably encodes all four alphaviral nonstructural proteins contains a mutation in at least one nonstructural protein selected from the group consisting of a mutation in nsP1 residues 346, 441, 473, nsP2 residues 438, 622, 634, 715, nsP3 residues, 417, 456, 505, and nsP4 residue 266.

Within yet another aspects of the present invention, eukaryotic layered vector initiation systems are provided, comprising a 5' promoter capable of initiating in vivo the 5' synthesis of alphavirus RNA from cDNA, a sequence which initiates transcription of alphavirus RNA following the 5' promoter, a nucleic acid molecule which operably encodes all four alphaviral nonstructural proteins, an alphavirus RNA polymerase recognition sequence, and a 3' polyadenylate tract, wherein the nucleic acid sequence which operably encodes all four alphaviral nonstructural proteins contains a mutation in at least one nonstructural protein selected from the group consisting of a mutation in nsP1 residues 346, 441, 473, nsP2 residues 438, 622, 634, 715, nsP3 residues, 417, 456, 505, and nsP4 residue 266, as compared to wild-type.

Within further embodiments alphavirus RNA vector replicons capable of translation in a eukaryotic system are provided, comprising a 5' sequence which initiates transcription of alphavirus RNA, a nucleic acid molecule which operably encodes all four alphaviral nonstructural proteins, an alphavirus RNA polymerase recognition sequence and a 3' polyadenylate tract, wherein the nucleic acid sequence which operably encodes all four alphaviral nonstructural proteins contains a mutation in at least one nonstructural protein selected from the group consisting of a mutation in nsP1 residues 346, 441, 473, nsP2 residues 438, 622, 634, 715, nsP3 residues, 417, 456, 505, and nsP4 residue 266, as compared to wild-type.

Within another aspect of the invention, methods are provided for generating an immune response in a warm-blood animal, comprising the step of administering to a warm-blooded animal any of the recombinant alphavirus particles described above that further comprise a heterologous sequence encoding an antigen from a virus, bacteria, fungus, parasite or cancerous cell.

Within a further aspect of the invention, methods are providing for generating an immune response within a warm-blooded animal, comprising the step of administering to a warm blooded animal one or more selected antigens by a first method (e.g., alphavirus vector particles, eukaryotic layered vector initiation system, DNA, protein), followed by administering to the same animal the same or similar antigen by a second method (e.g., alphavirus vector particles, eukaryotic layered vector initiation system, DNA, protein), wherein the first and second methods are different, with the proviso that either the first method or the second method or both methods is selected from the group consisting of alphavirus vector particles, RNA vector replicons or eukaryotic layered vector initiation systems. Within various embodiments of the invention, the immune response may be generated to treat a disease, and/or, to prevent a disease (e.g. as a vaccine).

Within another aspect of the invention, non-lymphotropic alphaviruses are provided, wherein the alphaviruses are capable of infecting dendritic cells (DC tropic). In one embodiment the dendritic cells are immature dendritic cells (e.g., CD1a+, CD86dim, CD83$^-$). In another embodiment, the alphaviruses are selected from the group consisting of Sindbis virus, Semliki Forest virus, and Ross River virus. In yet another embodiment, the alphavirus is a Sindbis virus that has an amino acid encoded at residue 160 of glycoprotein E2 that is not glutamic acid. Within a further embodiment, the alphavirus is not a Venezuelan equine encephalitis virus or Sindbis virus CMCC #4639 (deposited with the ATCC on Apr. 2, 1996: VR-2526). Within a further embodiment the alphavirus has the nucleic acid sequence set forth in FIG. 2B, or, a nucleic acid sequence which but for the redundancy of the genetic code encodes the same amino acid sequence. Within other aspects of the invention, non-lymphotropic alphaviruses are also provided, for example, as disclosed in FIG. 2C, or, a nucleic acid sequence which but for the redundancy of the genetic code encodes the same amino acid sequence. Also provided are alphavirus structural protein expression cassettes, RNA vector replicons, alphavirus vector particles, and eukaryotic layered vector initiation systems which are obtained or derived from, at least in part, one or more of the above-noted alphaviruses.

Within another aspect of the invention, alphavirus vector particles are provided, wherein the alphavirus vector particles are capable of infecting human dendritic cells with an efficiency of infection (percentage infected) greater than their efficiency for infecting murine dendritic cells. In one embodiment, the alphavirus vector particles can infect human dendritic cells at a 50%, 100%, 200%, or greater efficiency than their efficiency for infecting murine dendritic cells. In another embodiment the dendritic cells are immature human dendritic cells (e.g., CD1a+, CD86dim, CD83$^-$). In yet another embodiment, the alphavirus vector particles are derived from an alphaviruses selected from the group consisting of Sindbis virus, Semliki Forest virus, Ross River virus, and Venezuelan equine encephalitis virus. In yet another embodiment, the alphavirus vector particles are from Sindbis virus that has an amino acid encoded at residue 160 of glycoprotein E2 that is not glutamic acid. Within a further embodiment, the alphavirus vector particles are not derived from Sindbis virus CMCC #4639 (deposited with the ATCC on Apr. 2, 1996: VR-2526). Within a further embodiment, the alphavirus vector particles are derived from the nucleic acid sequence set forth in FIG. 2B, or, a nucleic acid sequence which but for the redundancy of the genetic code encodes the same amino acid sequence. Also provided are alphavirus structural protein expression cassettes, RNA vector replicons, and Eukaryotic Layered Vector Initiation Systems which are obtained or derived, at least in part, from one or more of the above-noted alphaviruses.

Within other aspects of the present invention, expression cassettes are provided comprising a promoter (e.g., a bacteriophage promoter for in vitro use, or an RNA pol II promoter for in vivo use) operably linked to a full-length cDNA clone of a DC tropic alphavirus from above, such that transcription of the full-length cDNA clone yields an RNA that initiates a productive viral infection when introduced into the cytoplasm of a susceptible cell. Also provided are alphavirus vector constructs, RNA replicons, cDNA vector construct, ELVIS, and the like which are derived from the above DC tropic alphaviruses. Within certain embodiments, vectors are provided comprising a 5'-promoter (bacteriophage or RNApolII) operably linked to the alphavirus vector cDNA sequence, subgenomic junction region promoter, heterologous gene to be expressed, and a polyadenylate tract.

A wide variety of antigens may be expressed from the alphavirus-based vector systems, including for example, antigens or peptides from a pathogenic agent (e.g., a cancerous cell, virus, bacteria, fungi, or parasite).

Within other aspects of the invention, a method of introducing and expressing a heterologous sequence in human dendritic cells in vivo or in vitro (e.g., for use in biological assays) is provided, comprising: infecting a population of human cells containing dendritic cells and/or dendritic cell precursors with a recombinant alphavirus vector particle according to the present invention for a time and under conditions necessary for intracellular expression of the replicon encoded heterologous gene within the dendritic cell, said alphavirus vector particle containing the heterologous sequence, with the proviso that said alphavirus vector particle is not derived entirely from Sindbis virus CMCC #4639 (deposited with the ATCC on Apr. 2, 1996: VR-2526). However, such particle may contain a portion of CMCC #4639. Within certain embodiments, the alphavirus vector particle is from at least a portion of a Sindbis virus, Semliki Forest virus, Venezuelan equine encephalitis virus or Ross River virus.

Within another aspect of the invention, a method of introducing and expressing a heterologous sequence in human dendritic cells and also inducing activation and/or maturation of said dendritic cells is provided, comprising: infecting a population of human cells containing dendritic cells and/or dendritic cell precursors with a recombinant alphavirus vector particle according to the present invention for a time and under conditions necessary for intracellular expression of the replicon encoded heterologous gene and activation and/or maturation of the dendritic cells, said alphavirus vector particle containing the heterologous sequence. Also provided are alphavirus vector particles comprising a vector replicon (as described in more detail below) and structural proteins necessary for particle formation, with the proviso that at least one structural protein of the vector particle is from a DC tropic alphavirus and said alphavirus vector particle is not derived entirely from Sindbis virus CMCC #4639 (deposited with the ATCC on Apr. 2, 1996: VR-2526; however, such particles may contain a portion of CMCC #4639). Within certain preferred embodiments, the vector replicon further comprises a gene encoding an antigen from a pathogenic agent.

Within other aspects of the invention, a method of introducing and expressing a heterologous sequence in dendritic cells is provided, comprising the step of infecting a population of cells containing dendritic cells and/or dendritic cell precursors with a recombinant alphavirus vector particle, the alphavirus vector particle containing the heterologous sequence and with the proviso that the alphavirus vector particle is not derived entirely from Venezuelan equine encephalitis virus or Sindbis virus CMCC #4639 (deposited with the ATCC on Apr. 2, 1996: VR-2526 (however, such particle may contain a portion of VEE or CMCC #4639)). Within certain embodiments, the alphavirus vector particle is from at least a portion of a Sindbis virus, Semliki Forest virus, or Ross River virus.

In further embodiments of the invention, the dendritic cells are immature dendritic cells. In another embodiment of the invention, said method of introducing and expressing a heterologous sequence in dendritic cells is carried out in vitro. Such dendritic cells may be removed from peripheral blood by apheresis or other means, and/or separated or enriched from bone marrow, or from cultured and/or expanded or differentiated hematopoetic cells (see, e.g., U.S. Pat. Nos. 4,927,750, 5,643,786, 5,646,004, 5,648,219, 5,648,248, 5,663,051, 5,788,963, 5,811,297, 5,851,756, 5,866,115 and 5,871,728; see also the Examples). In yet another embodiment of the invention, the method of introducing and expressing a heterologous sequence in dendritic cells is carried out in vivo, in a warm-blooded animal (e.g., by subcutaneous, intradermal, intramuscular, intranasal, intravenous injection).

Within other aspects of the invention, a method of introducing and expressing a heterologous sequence in human macrophages or antigen presenting cells in vivo or in vitro (e.g., for use in biological assays) is provided, comprising: infecting a population of cells containing human macrophages or antigen presenting cells with a recombinant alphavirus vector particle according to the present invention for a time and under conditions necessary for intracellular expression of the replicon encoded heterologous gene within the dendritic cell, said alphavirus vector particle containing the heterologous sequence, with the proviso that said alphavirus vector particle is not derived entirely from Sindbis virus CMCC #4639 (deposited with the ATCC on Apr. 2, 1996: VR-2526 (however, such particle may contain a portion of CMCC #4639)). Within certain embodiments, the alphavirus vector particle is from at least a portion of a Sindbis virus, Semliki Forest virus, Venezuelan equine encephalitis virus or Ross River virus.

Within other aspects, methods are provided for stimulating an immune response within a warm-blooded animal, comprising the general step of administering to a warm-blooded animal alphavirus vector particles described herein that infect dendritic cells and express an antigen or a portion thereof from a pathogenic agent. Within one embodiment, the alphavirus vector particles are not derived entirely from Venezuelan equine encephalitis virus or Sindbis virus CMCC #4639 (deposited with the ATCC Apr. 2, 1996: VR-2526 (however, such particles may contain a portion of VEE or CMCC #4639)). Within certain embodiments, the alphavirus vector particle is from at least a portion of a Sindbis virus, Semliki Forest virus, or Ross River virus.

Within other aspects, methods are provided for stimulating an antigen-specific T cell response, comprising the steps of infecting dendritic cells with alphavirus vector particles described herein that express an antigen from a pathogenic agent, and allowing presentation of said antigen by dendritic cells to T cells, such that said T cells are stimulated in an antigen-specific manner.

Within a further aspect of the present invention, isolated nucleic acid molecules encoding a Sindbis virus E2 glycoprotein gene are provided, wherein said nucleic acid molecule has an amino acid substitution or deletion for the wild-type glutamic acid at codon 160, and with the proviso that said glycoprotein gene is not obtained from VEE or CMCC #4639. Within one embodiment, a glycine residue is substituted at codon 160. Also provided are structural protein expression cassettes comprising such nucleic acid molecules, and alphavirus vector particles containing the above noted E2 structural protein.

These and other aspects of the present invention will become evident upon reference to the following detailed description and attached drawings. In addition, various references are set forth herein which describe in more detail certain procedures or compositions (e.g., plasmids, etc.), and are therefore incorporated by reference in their entirety.

BRIEF DESCRIPTION OF THE DRAWINGS

FIG. 2B is the nucleotide sequence of SinDCChiron virus (SEQ ID NO:2).

FIG. 2C is the nucleotide sequence of SinChironLP virus (SEQ ID NO:1).

Figure 6:
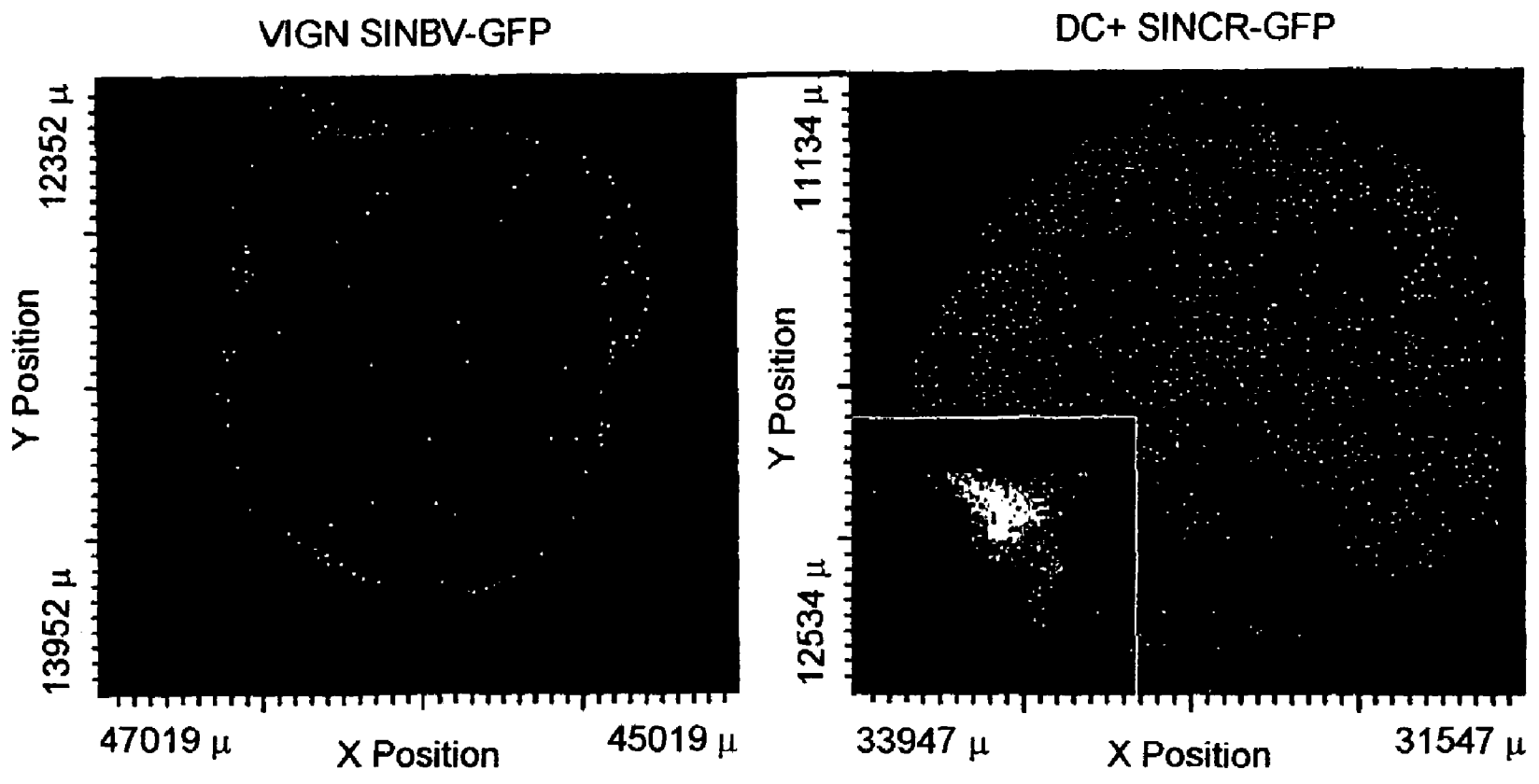

FIG. 6 shows laser cytometric analysis of DC variant SIN-GFP vector infected cells trafficking to the lymph node after administration to mice

DETAILED DESCRIPTION OF THE INVENTION

Definitions

Figure 1:
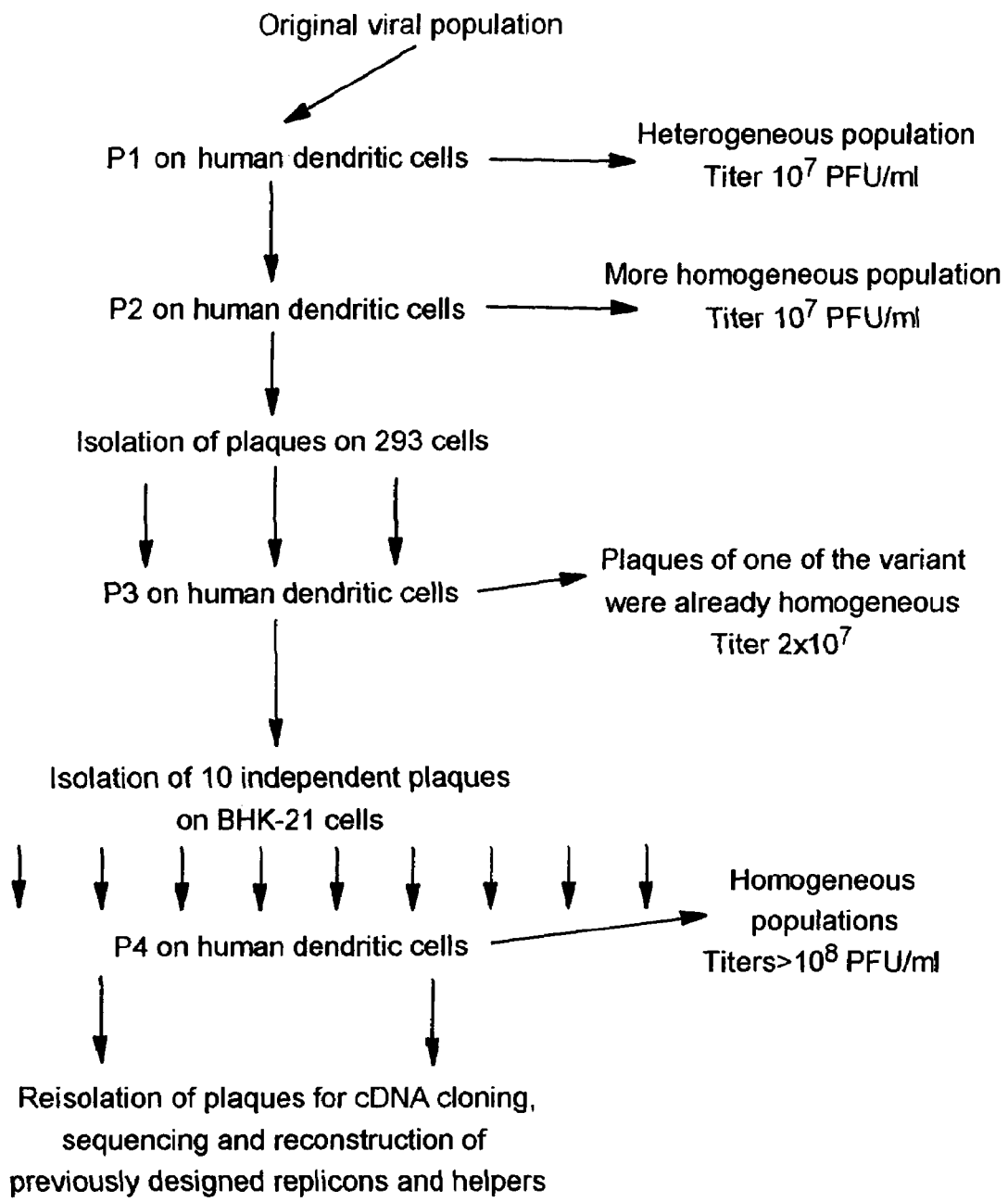
FIG. 1 is a schematic illustration of one representative flow chart of a human dendritic cell adaptation strategy for alphaviruses.

Prior to setting forth the invention, it may be helpful to an understanding thereof to first set forth definitions of certain terms that will be used hereinafter.

An "isolated nucleic acid molecule" is a nucleic acid molecule that is not integrated in the genomic DNA of an organism, or, in the case of the virus, not contained within the genome of a wild-type virus. One example of an isolated nucleic acid molecule is a chemically-synthesized nucleic acid molecule, or, a nucleic acid molecule that is produced by recombinant (e.g., PCR) techniques.

"Genomic RNA" refers to an RNA that contains all of the genetic information required to direct its own amplification or self-replication in vivo, within a target cell. An alphavirus-derived genomic RNA molecule should contain the following ordered elements: 5' viral or defective-interfering RNA sequence(s) required in cis for replication, sequences which, when expressed, code for biologically active alphavirus nonstructural proteins (e.g., nsP1, nsP2, nsP3, nsP4), 3' viral sequences required in cis for replication, and a polyadenylate tract. The alphavirus-derived genomic RNA vector replicon also may contain a viral subgenomic "junction region" promoter and sequences which, when expressed, code for biologically active alphavirus structural proteins (e.g., C, E3, E2, 6K, E1). Generally, the term genomic RNA refers to a molecule of positive polarity, or "message" sense, and the genomic RNA may be of length different from that of any known, naturally-occurring alphavirus.

"Alphavirus vector construct" refers to an assembly which is capable of directing the expression of a sequence or gene of interest. Such vector constructs are comprised of a 5' sequence which is capable of initiating transcription of an alphavirus RNA (also referred to as 5' CSE, in background), as well as sequences which, when expressed, code for biologically active alphavirus nonstructural proteins (e.g., nsP1, nsP2, nsP3, nsP4), an alphavirus RNA polymerase recognition sequence (also referred to as 3' CSE, in background), and a polyadenylate tract. In addition, the vector construct may include a viral subgenomic "junction region" promoter, sequences from one or more structural protein genes or portions thereof, extraneous nucleic acid molecule(s) which are of a size sufficient to allow production of viable virus, a 5' promoter which is capable of initiating the synthesis of viral RNA from cDNA in vitro or in vivo, a heterologous sequence to be expressed, and one or more restriction sites for insertion of heterologous sequences.

"Alphavirus RNA vector replicon", "RNA vector replicon" and "replicon" refers to an RNA molecule which is capable of directing its own amplification or self-replication in vivo, within a target cell. An alphavirus-derived RNA vector replicon should contain the following ordered elements: 5' viral sequences required in cis for replication (also referred to as 5' CSE, in background), sequences which, when expressed, code for biologically active alphavirus nonstructural proteins (e.g., nsP1, nsP2, nsP3, nsP4), 3' viral sequences required in cis for replication (also referred to as 3' CSE, in background), and a polyadenylate tract. The alphavirus-derived RNA vector replicon also may contain a viral subgenomic "junction region" promoter, sequences from one or more structural protein is genes or portions thereof, extraneous nucleic acid molecule(s) which are of a size sufficient to allow production of viable virus, as well as heterologous sequence(s) to be expressed.

"Recombinant Alphavirus Particle, Alphavirus Vector Particle" refers to a virion-like structural unit containing an alphavirus RNA vector replicon. Generally, a recombinant alphavirus particle comprises one or more alphavirus structural proteins, a lipid envelope and an RNA vector replicon. Preferably, the recombinant alphavirus particle contains a nucleocapsid structure that is contained within a host cell-derived lipid bilayer, as a plasma membrane, in which alphaviral-encoded envelope glycoproteins are embedded. Use of the term "recombinant" when referring to alphavirus particles means that the alphavirus particles that have been generated or modified by molecular genetic manipulation, and is does not refer to wild-type alphaviruses as found in nature. Recombinant alphavirus particles however may be derived from alphaviruses found in nature, when all or a portion of such an alphavirus is used to construct or otherwise generate a recombinant alphavirus particle.

"Alphavirus packaging cell line" refers to a cell which contains an alphavirus structural protein expression cassette and which produces recombinant alphavirus particles after introduction of an alphavirus vector construct, RNA vector replicon, eukaryotic layered vector initiation system, or recombinant alphavirus particle. The parental cell may be of mammalian or non-mammalian origin. Within preferred embodiments, the packaging cell line is stably transformed with the structural protein expression cassette.

"Eukaryotic Layered Vector Initiation System" or "ELVIS" refers to an assembly which is capable of directing the expression of a sequence(s) or gene(s) of interest. The eukaryotic layered vector initiation system should contain a 5' promoter which is capable of initiating in vivo (i.e., within a cell) the synthesis of RNA from cDNA, and a viral vector sequence which is capable of directing its own replication in a eukaryotic cell and also expressing a heterologous sequence. In preferred embodiments, the nucleic acid vector sequence is an alphavirus-derived sequence and is comprised of a 5' sequence which is capable of initiating transcription of an alphavirus RNA (also referred to as 5' CSE, in background), as well as sequences which, when expressed, code for biologically active alphavirus nonstructural proteins (e.g., nsP1, nsP2, nsP3, nsP4), and an alphavirus RNA polymerase recognition sequence (also referred to as 3' CSE, in background). In addition, the vector sequence may include a viral subgenomic "junction region" promoter, sequences from one or more structural protein genes or portions thereof, extraneous nucleic acid molecule(s) which are of a size sufficient to allow optimal amplification, a heterologous sequence to be expressed, one or more restriction sites for insertion of heterologous sequences, as well as a polyadenylation sequence. The eukaryotic layered vector initiation system may also contain splice recognition sequences, a catalytic ribozyme processing sequence, a nuclear export signal, and a transcription termination sequence.

"Antigen" refers to a molecule containing one or more epitopes (either linear, conformational or both) that will stimulate a host's immune system to make a humoral and/or cellular antigen-specific response. The term is used interchangeably with the term "immunogen." Normally, a B-cell epitope will include at least about 5 amino acids but can be as small as 3-4 amino acids. A T-cell epitope, such as a CTL epitope, will include at least about 7-9 amino acids and a helper T-cell epitope at least about 12-20 amino acids. Normally, an epitope will include between about 7 and 15 amino acids, such as, 9, 10, 12 or 15 amino acids. The term "antigen"

denotes both subunit antigens, (i.e., antigens which are separate and discrete from a whole organism with which the antigen is associated in nature), as well as, killed, attenuated or inactivated bacteria, viruses, fungi, parasites or other microbes. Antibodies such as anti-idiotype antibodies, or fragments thereof, and synthetic peptide mimotopes, which can mimic an antigen or antigenic determinant, are also captured under the definition of antigen as used herein. Similarly, an oligonucleotide or polynucleotide which expresses an antigen or antigenic determinant in vivo, such as in gene therapy and DNA immunization applications, is also included in the definition of antigen herein.

For purposes of the present invention, antigens can be derived from any of several known viruses, bacteria, parasites and fungi, as described more fully below. The term also intends any of the various tumor antigens. Furthermore, for purposes of the present invention, an "antigen" refers to a protein or peptide which includes modifications, such as deletions, additions and substitutions (generally conservative in nature), to the native sequence, so long as the protein maintains the ability to elicit an immunological response, as defined herein. These modifications may be deliberate, as through site-directed mutagenesis, or may be accidental, such as through mutations of hosts which produce the antigens.

An "immune response" to an antigen or composition is the development in a subject of a humoral and/or a cellular immune response to an antigen present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

A composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host.

The ability of a particular antigen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. See, e.g., Erickson et al., J. Immunol. 151:4189-4199, 1993; Doe et al., Eur. J. Immunol. 24:2369-2376, 1994. Recent methods of measuring cell-mediated immune response include measurement of intracellular cytokines or cytokine secretion by T-cell populations, or by measurement of epitope specific T-cells (e.g., by the tetramer technique) (reviewed by McMichael, A. J. and O'Callaghan, C. A., J. Exp. Med. 187(9):1367-1371, 1998; Mcheyzer-Williams, M. G. et al., Immunol. Rev. 150: 5-21, 1996; Lalvani, A. et al., J. Exp. Med. 186:859-865, 1997).

Thus, an immunological response as used herein may be one which stimulates the production of CTLs, and/or the production or activation of helper T-cells. The antigen of interest may also elicit an antibody-mediated immune response. Hence, an immunological response may include one or more of the following effects: the production of antibodies by B-cells; and/or the activation of suppressor T-cells and/or T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays known in the art.

"Immature Dendritic Cells" refers to a population of cells with particular characteristics as outlined below. The criteria for identifying immature dendritic cells, both in cytokine-driven culture and from primary tissues, include their dendritic morphology, motility, phagocytic activity. Immature dendritic cells express surface CD1a, moderate expression of surface MHC and costimulatory molecules (e.g. CD40, CD80, CD86) and are negative for CD3, CD19, CD20 and CD83 (Banchereau and Steinman, Nature 392, 245-252, 1998). These cells have the capacity to differentiate into mature immunostimulatory antigen presenting cells, both dendritic cells and macrophages, the latter being generated via a CD14+ cell intermediate (Cella et al. Curr Opin in Immunol. 9:10-16, 1997). Mature dendritic cells (CD86+, MHC+ and CD83+, CD14−) and macrophages (CD14+, MHC+ c-fins+, CD83−) can present processed antigens to immune cells and are thus referred to as professional antigen-presenting cells (Hart, Blood 90: 3245-3287, 1997).

"Infects human dendritic cells" refers to recombinant alphavirus particles or alphaviruses that efficiently infect or transduce human dendritic cells. In this context, transduction or infection efficiency refers to the ability of a recombinant alphavirus particle or alphavirus to bind to, penetrate and deliver an RNA vector replicon or alphavirus genome to the cytoplasm of a host cell, thereby allowing replicon mediated expression of a heterologous sequence (e.g., a reporter or antigen), or genome-mediated expression of structural proteins in a host cell. Generally, recombinant alphavirus particles or alphaviruses will efficiently transduce or infect host cells in vitro at 10, 20, 25, or 50 fold over a wild-type alphavirus of the same species at an MOI of 100 or less. Alternatively, transduction or infection efficiency is at least 20, 30, 40, or 50% of cells when performed in vitro at an MOI of 100 or less. Wild-type alphaviruses for comparison, as well as cDNA clones for use in the construction of corresponding replicons and structural protein expression cassettes, can be obtained by using full-length virus clones referenced in the following publications: Sindbis virus—Rice et al., 1987, J. Virol. 61:3809-3819; Semliki Forest virus—Liljestrom et al., 1991, J. Virol. 65:4107-4113; Ross River virus—Kuhn et al., 1991, Virology 182:430-441; Venezuelan equine encephalitis virus—Davis et al., 1989, Virology 171:189-204.

"Isolated alphaviruses" refers to alphaviruses that are separated from the cells in which they are propagated. Alphaviruses may be further purified by a number of techniques, including for example, plaque purification.

As noted above, the present invention provides compositions and methods suitable for generating an immune response in a warm-blooded animal (e.g., a human, horse, cow, sheep, pig, dog, cat, rat or mouse), comprising the general step of administering to an animal a gene delivery vector (e.g., alphavirus vector particles, ELVIS, DNA), or, protein followed by the step of administering to the same animal the same or similar antigen by a second gene delivery vector (e.g. alphavirus vector particles, ELVIS, or, DNA), or, protein, wherein the first and second methods are different. By administering two separate gene delivery vectors (or a vector and protein), one can boost the immune response of the warm-blooded animal to the desired antigen.

In order to further an understanding of the present invention, described in more detail below are (A) methods for generating alphavirus-based gene delivery vectors and DNA-based gene delivery vectors; and (B) methods of utilizing one or both in a variety of methods.

A. Alphavirus-Based Gene Delivery Vectors, and DNA-Based Gene Delivery Vectors

A wide variety of alphavirus-based gene delivery vectors may be readily generated using the disclosure provided herein. Representative examples of such vectors include RNA vector replicons, alphavirus vector constructs, and recombinant alphavirus particles. Briefly, sequences encoding wild-type alphaviruses suitable for use in preparing the above-described vectors can be readily obtained from naturally-occurring sources, or from depositories (e.g., the American Type Culture Collection, Rockville, Md.). In addition, wild-type alphaviruses may be utilized for comparing their ability to infect dendritic cells, macrophages or antigen presenting cells with the alphaviruses and derived vectors of the present invention.

Representative examples of suitable alphaviruses include Aura virus (ATCC VR-368), Bebaru virus (ATCC VR-600, ATCC VR-1240), Cabassou virus (ATCC VR-922), Chikungunya virus (ATCC VR-64, ATCC VR-1241), Eastern equine encephalomyelitis virus (ATCC VR-65, ATCC VR-1242), Fort Morgan virus (ATCC VR-924), Getah virus (ATCC VR-369, ATCC VR-1243), Kyzylagach virus (ATCC VR-927), Mayaro virus (ATCC VR-66, ATCC VR-1277), Middleburg virus (ATCC VR-370), Mucambo virus (ATCC VR-580, ATCC VR-1244), Ndumu virus (ATCC VR-371), Pixuna virus (ATCC VR-372, ATCC VR-1245), Ross River virus (ATCC VR-373, ATCC VR-1246), Semliki Forest virus (ATCC VR-67, ATCC VR-1247), Sindbis virus (ATCC VR-68, ATCC VR-1248; see also CMCC #4640, described below), Tonate virus (ATCC VR-925), Triniti virus (ATCC VR-469), Una virus (ATCC VR-374), Venezuelan equine encephalomyelitis virus (ATCC VR-69, ATCC VR-923, ATCC VR-1250 ATCC VR-1249, ATCC VR-532), Western equine encephalomyelitis virus (ATCC VR-70, ATCC VR-1251, ATCC VR-622, ATCC VR-1252), Whataroa virus (ATCC VR-926), and Y-62-33 virus (ATCC VR-375).

Representative examples of suitable methods for constructing alphavirus-based vector systems are described in more detail in PCT Publication No. WO 97/38087 entitled "Recombinant Alphavirus-Based Vectors With Reduced Inhibition Of Cellular Macromolecular Synthesis" and U.S. Pat. Nos. 5,091,309 and 5,217,879, 5,843,723, and 5,789,245.

Within one aspect of the invention, a variety of expression cassettes are provided, which contain the sequences coding for and operably express one or more alphavirus structural polypeptides provided herein. Generally, the expression cassettes fall within one of three categories: 1) a DNA promoter of RNA transcription (e.g., RNA polymerase II promoter) directly and operably linked to the structural protein open reading frame (ORF), and a transcription termination/polyadenylation sequence; 2) an alphavirus defective helper RNA transcribed in vitro or in vivo, comprising the ordered elements 5' viral or defective-interfering RNA sequence required in cis for alphaviral replication (also referred to as 5' CSE, in background), viral subgenomic junction region promoter, alphavirus structural protein sequence of the present invention, 3' alphaviral sequence required in cis for replication (also referred to as 3' CSE, in background), and polyadenylate tract; and 3) DNA cassettes comprising the ordered elements of a DNA promoter of RNA transcription that functions within a eukaryotic cell (e.g., RNA polymerase II promoter) and is operably linked to a 5' viral or defective-interfering RNA sequence required in cis for alphaviral replication, viral subgenomic junction region promoter, alphavirus structural protein sequence of the present invention, 3' alphaviral sequence required in cis for replication, polyadenylate tract, and transcription termination/polyadenylation sequence. In preferred embodiments, the structural proteins of the present invention are synthesized at high levels by the cassettes only after induction by the RNA vector replicon itself or some other provided stimulus. In further embodiments, the structural protein expression cassettes do not express all alphavirus nonstructural proteins.

Within further aspects of the invention, alphavirus packaging cell lines are provided. In particular, within one aspect of the present invention, alphavirus packaging cell lines are provided wherein the viral structural proteins are supplied in trans from one or more stably transformed expression cassettes, and are able to encapsidate transfected, transduced, or intracellularly produced alphavirus vector RNA transcripts in the cytoplasm and release functional packaged vector particles through the plasma membrane. In preferred embodiments, the structural proteins necessary for packaging are synthesized at high levels only after induction by the RNA vector replicon itself or some other provided stimulus, and the transcripts encoding these structural proteins are capable of cytoplasmic amplification in a manner that will allow expression levels sufficient to mimic that of a natural viral infection (WO 97/38087 and U.S. Pat. No. 5,789,245). In other embodiments, the structural proteins may be specifically modified prior to use in alphavirus packaging cell lines (e.g., sequence coding for the nuclear localization signal of VEE capsid protein may be altered by site-directed mutagenesis to prevent this function). Furthermore, in other embodiments, expression of a selectable marker is operably linked to the structural protein expression cassette. Such a linked selectable marker allows efficient generation of stable packaging cell lines.

As provided by the invention, methods for generation (packaging) of recombinant alphavirus vector particles are provided and may be readily accomplished for example, by co-transfection of complementing vector and defective helper (DH) molecules as in vitro transcribed RNA or plasmid DNA, or by co-infection with virus (see Xiong et al., *Science* 243: 1188-1191, 1989, Bredenbeek et al., *J. Virol.* 67:6439-6446, 1993, Dubensky et al., *J. Virol* 70:508-519, 1996 and U.S. Pat. Nos. 5,814,482, 5,739,026, 5,766,602, 5,789,245 and 5,792,462. Alternatively, vector particles may be generated by introduction of vector RNA into stable alphavirus packaging cell lines or "PCL" (Polo et al., PNAS 96:4598-4603; U.S. Pat. No. 5,789,245). Briefly, such PCL and their stably transformed structural protein expression cassettes can be derived using methods described within U.S. Pat. No. 5,789,245, or using novel methods described within this invention. For example, the production of recombinant alphavirus vector particles by PCL may be accomplished following introduction of alphavirus-based vector molecules into the PCL, the vectors being derived from in vitro transcribed RNA, plasmid DNA, or previously obtained recombinant alphavirus particles, incubating the PCL for a under conditions and for a time necessary for vector particle packaging, and harvesting of the packaged vector particles. Packaging cell lines may be used for the serial propagation of alphavirus vector particles following high or low multiplicity of infection.

In addition to the above viral-based vectors, numerous non-viral gene delivery vehicles may likewise be utilized within the context of the present invention. Representative examples of such gene delivery vehicles include direct delivery of nucleic acid expression vectors or naked. DNA alone (see e.g., U.S. Pat. Nos. 5,814,482 and 5,580,859), B. Use of Gene Therapy Vectors As noted above, within one aspect of the present invention methods are provided for generating or enhancing an immune response utilizing one or more gene delivery vectors (e.g., alphavirus vectors) and/or recombinant protein in order to prime and boost an immune response. Representative examples of such disease targets include viral infections such as HIV, HBV, HCV, HTLV I, HTLV II, CMV, EBV, HSV, respiratory syncytial virus, HPV, as well as cancer antigens (e.g., melanoma). More specifically, within one aspect of the present invention, compositions and methods are provided for stimulating an immune response (either humoral or cell-mediated) to a pathogenic agent, such that the pathogenic agent is either killed or inhibited. Representative examples of pathogenic agents include bacteria, fungi, parasites, viruses and cancer cells.

This approach presents a distinct advantage over others since the antigenic epitopes expressed can be altered by selective cloning of sub-fragments of the gene for the antigen into the alphavirus vector, leading to responses against immunogenic epitopes which may otherwise be overshadowed by immunodominant epitopes. Such an approach may be extended to the expression of a peptide having multiple epitopes, one or more of the epitopes being derived from different proteins. Further, this aspect of the invention allows efficient stimulation of cytotoxic T lymphocytes (CTL) directed against antigenic epitopes, and peptide fragments of antigens encoded by sub-fragments of genes, through intracellular synthesis and association of these peptide fragments with MHC Class I molecules. This approach may be utilized to map major immunodominant epitopes for CTL induction.

An immune response may also be achieved by transferring to an appropriate immune cell (such as a T lymphocyte) the gene for the specific T cell receptor which recognizes the antigen of interest (in the context of an appropriate MHC molecule if necessary), for an immunoglobulin which recognizes the antigen of interest, or for a hybrid of the two which provides a CTL response in the absence of the MHC context. Thus, the gene delivery vehicle cells may be used as an immunostimulant, immunomodulator, or vaccine.

Figure 8:
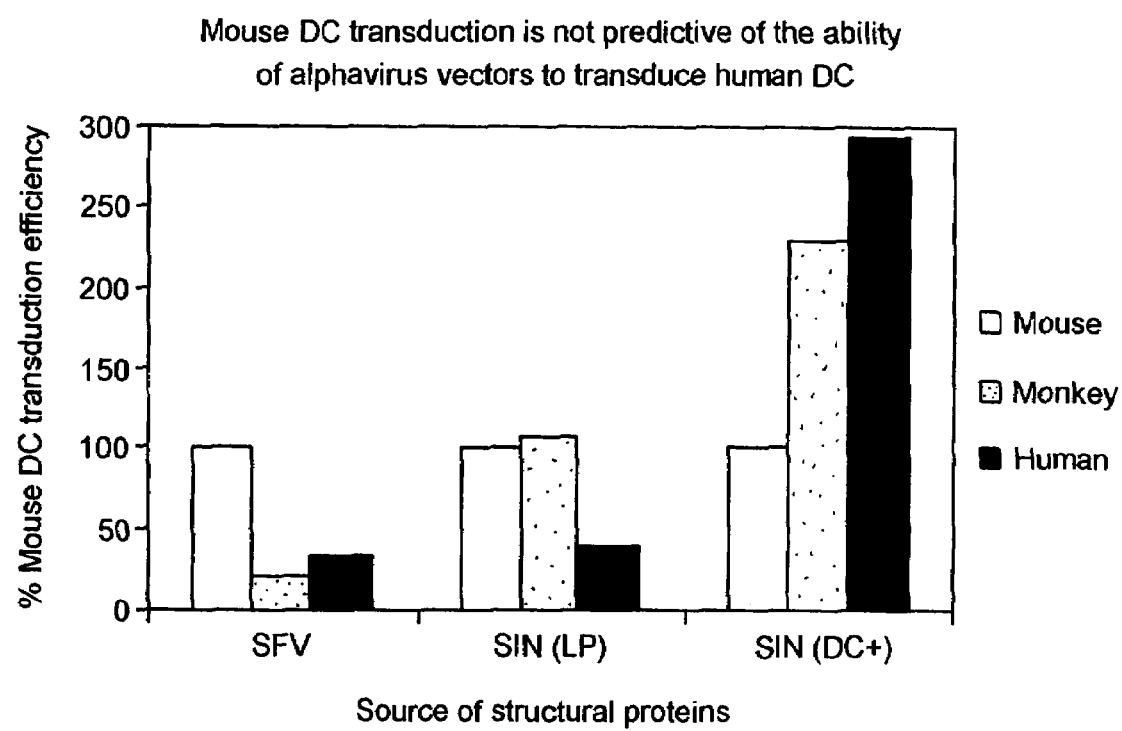
FIG. 8 is a graph showing that alphaviruses (e.g., SFV or SIN-LP) are capable of infecting murine DC, but not human DC unless they are first modified or adapted for the efficient infection of such human DC (see for example SIN DC+).
Figure 9:
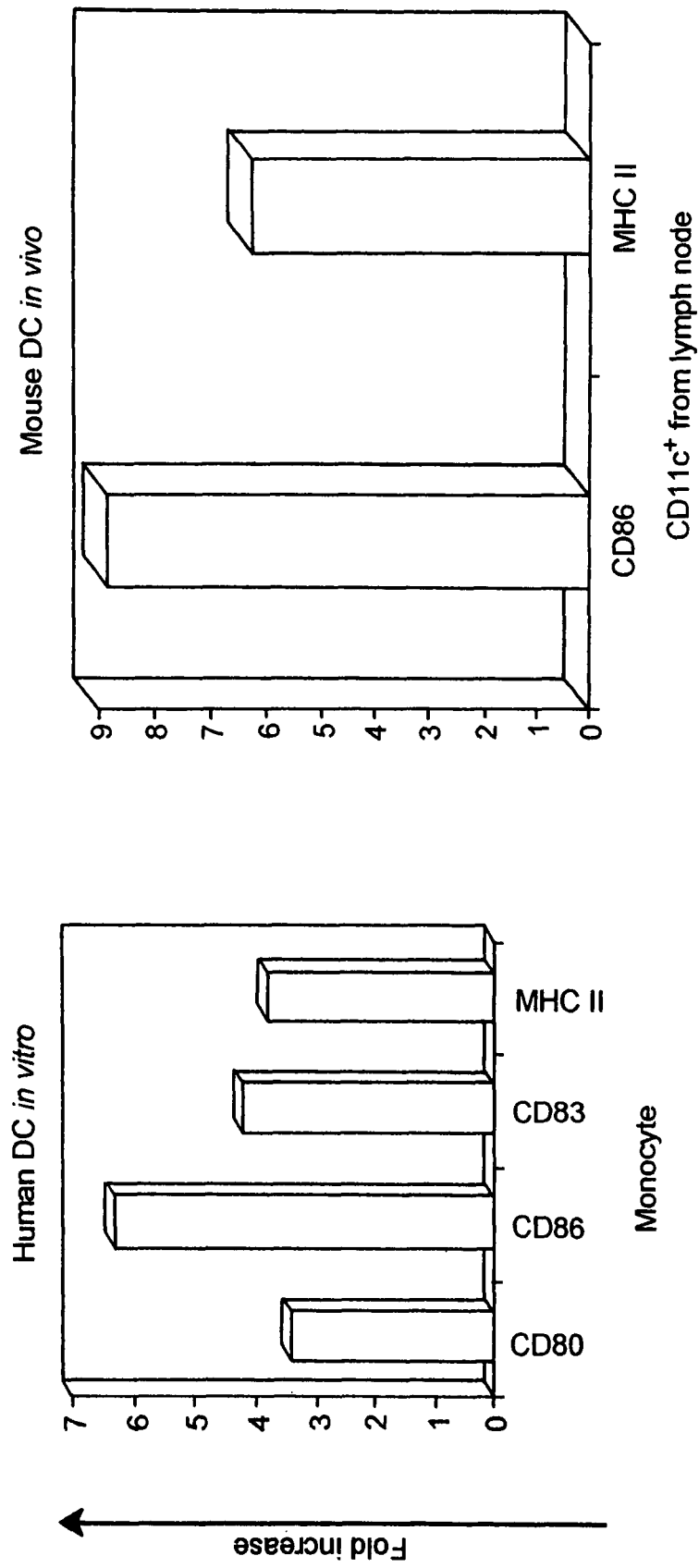
FIG. 9 is a graph showing alphavirus (e.g., SIN) vector induced maturation and activation of human DC following transduction in vitro and murine DC following transduction in vivo.

One particularly appealing use for alphavirus vectors is human vaccine and therapeutic application. As described in the detailed description and examples below, the present invention provides compositions and methods to increase the potency of such alphavirus-based systems, particularly in the area of vaccines. One approach exemplified by the present invention is the targeting of alphavirus vectors directly to antigen presenting cells (e.g., dendritic cells, macrophages). It is known that among the many members of the alphavirus genus, Venezuelan equine encephalitis (VEE) virus is naturally lymphotropic, while the other members are not (Caley et al., *J. Virol.* 71:3031-3038, 1997). Yet it has also been observed that one member of the alphavirus group, VEE (MacDonald et al., J. Virol. 74:914-922), and now SFV and SIN (FIG. 8) are capable of infecting murine dendritic cells at relatively high efficiency. Unfortunately, the ability of an alphavirus to efficiently infect murine dendritic cells is not predictive of its ability to efficiently infect human dendritic cells (FIG. 8), which would be a goal of vaccine optimization for human use with these vectors. It should also be noted that VEE virus is a significant human pathogen responsible for sporadic epidemic outbreaks of encephalitis, resulting in multiple deaths or permanent central nervous system sequalae in virus infected individuals. Thus, VEE is classified for use under BL-3 level containment, suggesting that its development as a vaccine vector is somewhat dubious.

As illustrated below, alphaviruses, including those considered to be non-lymphotropic alphaviruses (see Caley et al., ibid) may be modified or adapted for efficient infection of human dendritic cells, their genomes then cloned, sequenced, and genetic modifications responsible then used in the construction of vectors and packaging cassettes useful for gene delivery to human dendritic cells. It should also be noted that this method of modification or adaptation to specifically target desired human cell types or populations is not limited to dendritic cells. Rather, the method can be extended to other relevant target cell types (e.g., cancer cells) by using the same process of cycling virus or vector through primary cultured cells, followed by cloning and construction of vectors and packaging cassettes. The invention also provides additional strategies to enhance the vaccine efficacy of alphavirus-based vectors, by utilizing prime-boost regimes that comprise administering or expressing a desired antigen using two separate and different methods, selected for example from alphavirus vector particles, nucleic acid (e.g., DNA) or recombinant protein, and combined in any variety of order, provided that either the prime or the boost or both is an alphavirus derived vector.

Administration of the vectors and/or recombinant proteins of the present invention to a vaccine, for example in the prime/boost strategy, may be accomplished by a variety of routes. For example, within one embodiment a warm-blooded animal may be primed by a first method (e.g., alphavirus vector particles, ELVIS, DNA, or recombinant protein) that stimulates an immune response against the desired antigen(s). A wide variety of inoculation routes may be utilized in this regard, including for example, intraocularly, intranasally, sublingually, orally, topically, intravesically, intrathecally, intravaginally, intrarectally topically, intravenously, intraperitoneally, intracranially, intramuscularly, intradermally, or, subcutaneously. Priming by the first method may include multiple administrations of the selected method. Following priming, the same or substantially the same antigen is administered to the same animal via a second method (e.g., alphavirus vector particles, ELVIS, DNA, or recombinant protein) that stimulates an immune response against the desired antigen(s). Similar to the priming step, wide variety of inoculation routes may be utilized in this regard (see above list). Within certain embodiments, the boosting step may be performed several times, as is best suited to generate a protective or therapeutic immune response.

Within yet other aspects of the present invention, the above-described alpha virus-based vector system (e.g. alphavirus vector particles, RNA vector replicons, eukaryotic layered vector initiation systems and the like) may be used for non-vaccine therapeutics, such as the treatment of coronary artery disease (CAD) and/or peripheral vascular disease (PVD). For example, within one embodiment an alphavirus-based vector such as ELVIS or recombinant alphavirus particle can be administered to a patient to treat or prevent CAD or PVD. In cardiovascular indications, including CAD and PVD, alphavirus vectors, both DNA- and particle-based can be used to deliver particular palliatives which stimulate angiogenesis and/or neovascularization. Included among these palliatives are, for example, fibroblast growth factor (e.g., FGF 1, 2, 4, 5, 18), vascular endothelial growth factor (e.g., VEGF-2, D), endothelial nitric oxide synthetase (e.g., NOS). Delivery of these vectors for therapeutic effect can be accomplished by several alternative routes, including for example intramuscular for PVD, and intracoronary, intramyocardial, or perivascular, for CAD.

Adjuvants may also be used to enhance the effectiveness of the vaccinating compositions used for priming or boosting. Such adjuvants include, but are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides (see below) or bacterial cell wall components), such as for example (a) MF59 (International Publication No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ (Cambridge Bioscience, Worcester, Mass.) may be used or particle generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor, (M-CSF), tumor necrosis factor (TNF), etc.; (6) oligonucleotides or polymeric molecules encoding immunostimulatory CpG motifs (Davis, H. L., et al., *J. Immunology* 160:870-876, 1998; Sato, Y. et al., *Science* 273:352-354, 1996) or complexes of antigens/oligonucleotides. Polymeric molecules include double and single stranded RNA and DNA, and backbone modifications thereof, for example, methylphosphonate linkages. Further, such polymeric molecules include alternative polymer backbone structures such as, but not limited to, polyvinyl backbones (Pitha, *Biochem Biophys Acta* 204:39, 1970a; Pitha, *Biopolymers* 9:965, 1970b), and morpholino backbones (Summerton, J., et al., U.S. Pat. No. 5,142,047, issued Aug. 25, 1992; Summerton, J., et al., U.S. Pat. No. 5,185,444 issued Feb. 9, 1993). A variety of other charged and uncharged polynucleotide analogs have been reported. Numerous backbone modifications are known in the art, including, but not limited to, uncharged linkages (e.g., methyl phosphonates, phosphotriesters, phosphoamidates, and carbamates) and charged linkages (e.g., phosphorothioates and phosphorodithioates)}; and (7) other substances that act as immunostimulating agents to enhance the effectiveness of the VLP immune-stimulating (or vaccine) composition. Alum, CpG oligonucleotides, and MF59 are preferred.

A variety of genes encoding polypeptide antigens can be used in the practice of the present invention. Antigens can be derived from a wide variety of viruses, bacteria, fungi, protozoans and other parasites. For example, the present invention will find use for stimulating an immune response against a wide variety of proteins or peptides from the herpes virus family, including proteins derived from herpes simplex virus (HSV) types 1 and 2, such as HSV-1 and HSV-2 gB, gD, gH, VP16 and VP22; antigens derived from varicella zoster virus (VZV), Epstein-Barr virus (EBV) and cytomegalovirus (CMV) including CMV gB and gH; and antigens derived from other human herpesviruses such as HHV6 and HHV7. (See, e.g. Chee et al., *Cytomegaloviruses* (J. K. McDougall, ed., Springer-Verlag 1990) pp. 125-169, for a review of the protein coding content of cytomegalovirus; McGeoch et al. *J. Gen. Virol.* 69:1531-1574, 1988, for a discussion of the various HSV-1 encoded proteins; U.S. Pat. No. 5,171,568 for a discussion of HSV-1 and HSV-2 gB and gD proteins and the genes encoding therefor; Baer et al., *Nature* 310:207-211, 1984, for the identification of protein coding sequences in an EBV genome; and Davison and Scott, *J. Gen. Virol* 67:1759-1816, 1986, for a review of VZV.)

Additionally, immune responses to antigens from viruses associated with hepatitis, including hepatitis A virus (HAV), hepatitis B virus (HBV), hepatitis C virus (HCV), the delta hepatitis virus (HDV), hepatitis E virus (HEV), and hepatitis G virus, can also be stimulated using the constructs of the present invention. By way of example, the HCV genome encodes several viral proteins, including the structural core, E1 (also known as E) and E2 (also known as E2/NSI) proteins, as well as nonstructural proteins (e.g., NS3, NS4, NS5), which will find use with the present invention (see, Houghton et al. *Hepatology* 14:381-388, 1991, for a discussion of HCV proteins, including E1 and E2). The delta-antigen from HDV can also be used (see, e.g., U.S. Pat. No. 5,389,528, for a description of the delta-antigen).

Similarly, influenza virus is another example of a virus for which the present invention will be particularly useful. Specifically, the envelope glycoproteins HA and NA of influenza A are of particular interest for generating an immune response. Numerous HA subtypes of influenza A have been identified (Kawaoka et al., *Virology* 179:759-767, 1990; Webster et al. "Antigenic variation among type A influenza viruses," p. 127-168. In: P. Palese and D. W. Kingsbury (ed.), *Genetics of influenza viruses*. Springer-Verlag, New York).

Other antigens of particular interest to be used in the practice of the present invention include antigens and polypeptides derived therefrom from human papillomavirus (HPV), such as one or more of the various early proteins including E6 and E7; tick-borne encephalitis viruses; and HIV-1 (also known as HTLV-III, LAV, ARV, etc.), including, but not limited to, antigens such as gp120, gp41, gp160, Gag and pol from a variety of isolates including, but not limited to, $HIV_{IIIb}$, $HIV_{SF2}$, HIV-$1_{SF162}$, HIV-$1_{SF170}$, $HIV_{LAV}$, $HIV_{LAI}$, $HIV_{MN}$, HIV-$1_{CM235}$, HIV-$1_{US4}$ other HIV-1 strains from diverse subtypes (e.g., subtypes, A through G, and O), HIV-2 strains and diverse subtypes (e. HIV-$2_{UC1}$ and HIV-$2_{UC2}$). See, e.g., Myers, et al., Los Alamos Database, Los Alamos National Laboratory, Los Alamos, N. Mex.; Myers, et al., *Human Retroviruses and Aids,* 1990, Los Alamos, N. Mex.: Los Alamos National Laboratory.

Proteins derived from other viruses will also find use in the methods described herein, such as for example, proteins from members of the families Picornaviridae (e.g., polioviruses, etc.); Caliciviridae; Togaviridae (e.g., rubella virus, dengue virus, etc.); Flaviviridae; Coronaviridae; Reoviridae; Birnaviridae; Rhabdoviridae (e.g., rabies virus, etc.); Filoviridae; Paramyxoviridae (e.g., mumps virus, measles virus, respiratory syncytial virus, etc.); Orthomyxoviridae (e.g., influenza virus types A, B and C, etc.); Bunyaviridae; Arenaviridae; Retroviradae, e.g., HTLV-I; HTLV-II; HIV-1; HIV-2; simian immunodeficiency virus (SIV) among others.

See, e.g., Virology, 3rd Edition (W. K. Joklik ed. 1988); *Fundamental Virology*, 2nd Edition (B. N. Fields and D. M. Knipe, eds. 1991; *Virology*, 3rd Edition (Fields, B N, D M Knipe, P M Howley, Editors, 1996, Lippincott-Raven, Philadelphia, Pa.) for a description of these and other viruses.

Particularly preferred bacterial antigens are derived from organisms that cause diphtheria, tetanus, pertussis, meningitis, and other pathogenic states, including, without limitation, antigens derived from *Corynebacterium diphtheriae, Clostridium tetani, Bordetella pertusis, Neisseria meningitidis*, including serotypes *Meningococcus* A, B, C, Y and W135 (MenA, B, C, Y and W135), *Haemophilus influenza* type B (Hib), and *Helicobacter pylori*. Examples of parasitic antigens include those derived from organisms causing malaria and Lyme disease.

Furthermore, the methods described herein provide means for treating a variety of malignant cancers. For example, the system of the present invention can be used to enhance both humoral and cell-mediated immune responses to particular proteins specific to a cancer in question, such as an activated oncogene, a fetal antigen, or an activation marker. Tumor antigens include any of the various MAGEs (melanoma associated antigen E), including MAGE 1, 2, 3, 4, etc. (Boon, T. *Scientific American* (March 1993):82-89); any of the various tyrosinases; MART 1 (melanoma antigen recognized by T cells), mutant: ras; mutant p53; p97 melanoma antigen; CEA (carcinoembryonic antigen), among others.

C. Deposit Information

The following materials have been deposited with the American Type Culture Collection:

| Deposit | Designation | Deposit Date | Accession No. |
| --- | --- | --- | --- |
| Wild type Sindbis virus | CMCC #4639 | Apr. 2, 1996 | VR-2526 |
| SinDCchiron virus | NA | Apr. 13, 1999 | VR-2643 |

The above materials were deposited by Chiron Corporation with the American Type Culture Collection (ATCC), under the terms of the Budapest Treaty on the International Recognition of the Deposit of Microorganisms for purposes of Patent Procedure. The accession number is available from the ATCC at telephone number (301) 881-2600.

These deposits are provided as convenience to those of skill in the art, and are not an admission that a deposit is required under 35 U.S.C. §112. The nucleic acid sequence of these deposits, as well as the amino acid sequence of the polypeptides encoded thereby, are incorporated herein by reference and should be referred to in the event of an error in the sequence described therein. A license may be required to make, use, or sell the deposited materials, and no such license is granted hereby.

The following examples are included to more fully illustrate the present invention. Additionally, these examples provide preferred embodiments of the invention and are not meant to limit the scope thereof. Standard methods for many of the procedures described in the following examples, or suitable alternative procedures, are provided in widely reorganized manuals of molecular biology, such as, for example, "Molecular Cloning," Second Edition (Sambrook et al., Cold Spring Harbor Laboratory Press, 1987) and "Current Protocols in Molecular Biology" (Ausubel et al., eds. Greene Associates/Wiley Interscience, NY, 1990), as well as in U.S. Pat. Nos. 6,015,686, 5,814,482, 6,015694, 5,842,723, and 5,789,245, and as such, each of these is referenced in its entirety.

EXAMPLES

Example 1

Selection and Cloning of Alphavirus Variants that Infect Primary Human Dendritic Cells In order to demonstrate that viruses of the Alphavirus genus, including those previously characterized as non-lymphotropic or previously shown to infect murine dendritic cells, could be modified or adapted to efficiently infect and propagate in human dendritic cells, Sindbis virus was chosen as a representative example. Other similar alphaviruses, such as Semliki Forest virus, Venezuelan equine encephalitis virus and Ross River virus, also may be readily substituted by one of skill in the art, using the disclosure provided herein. Using a naturally occurring heterogeneous virus sample that was propagated only a very limited number of cycles in common laboratory cell lines, adaptation was performed as outlined in FIG. 1. Briefly, the virus was passaged 4 times in primary human dendritic cells obtained from different donors, with intermediate plaque purification in 293 and BHK-21 cells.

The primary human dendritic cells used for virus passage were derived from peripheral blood monocytes as previously described (Bender et al., *J Immunol. Meth.* 196:121, 1996). The buffy coat population of cells was obtained from healthy donors at the Blood Center of the Pacific (San Francisco, Calif.) or Stanford Medical School Blood Center (Palo Alto, Calif.). $CD14^+$ monocytes were isolated by negative depletion using Monocyte Isolation Kits and mini-MACS columns (Miltenyi Biotec GmbH), according to the manufacturer's instructions. Dendritic cells Were generated from the CD14+ cells by culturing at $0.6 \times 10^6$ per ml in RPMI 1640 medium, supplemented with 10% FCS, 2 mM glutamine, penicillin/streptomycin, 1,000 U/ml rhGM-CSF (Peprotech), and 1,000 U/ml rhIL-4 (Peprotech). Culture medium containing cytokines was replenished every two days. Monocyte-conditioned medium (MCM) was prepared as previously described (Bender et al., ibid) and was added to immature DC cultures at 30% (vol/vol) to induce maturation, either 5 or 6 days following culture initiation, for 3 additional days. Expression of cell surface markers upon MCM-treatment was analyzed by flow cytometry.

Following dendritic cell adaptation, a panel of plaque-purified clonal virus variants was able to grow efficiently in primary human dendritic cells, producing virus titers of greater than $10^8$ PFU/ml, or 1000 infectious virus particles/cell. Each clonal variant formed small plaques on BHK-21 and Vero cells, as compared to the parental virus and other common laboratory Sindbis virus strains. One of the DC-selected plaque-purified viruses was chosen for cDNA cloning, and an agarose plug from the last plaque purification step was incubated in 1 ml of media (MEM with 10% FBS) for 4 hours at 4° C. A 100 ul aliquot of virus eluate then was used to infect $10^6$ BHK-21 cells. After development of CPE the media (5 ml) was harvested. This virus stock produced homogeneous small plaques on both BHK-21 and Vero cells, and the titer was $2 \times 10^8$ PFU/ml. Virus from this seed stock, designated SinDCchiron, was deposited with American Type Culture Collection according to the requirements of the Budapest Treaty.

In addition, a small number of spontaneous large plaque variants were observed sporadically in BHK-21 and Vero cells. The plaque size of these variants was significantly larger than the parental virus and other common laboratory strains of Sindbis virus. Similar to other alphaviruses, this large plaque virus variant was inefficient at infecting primary human dendritic cells and produced very low titers of progeny virus (<$10^5$ PFU/ml). One of the large plaque variants was chosen for cDNA cloning, and an agarose plug from the last plaque purification step was incubated in 1 ml of media (MEM with 10% FBS) for 4 hours at 4° C. A 100 ul aliquot of virus eluate then was used to infect $10^6$ BHK-21 cells. After development of CPE the media (5 ml) was harvested. This virus stock produced homogeneous large plaques on both BHK-21 and Vero cells. Virus from this seed stock was designated SinChironLP.

Figure 2A:
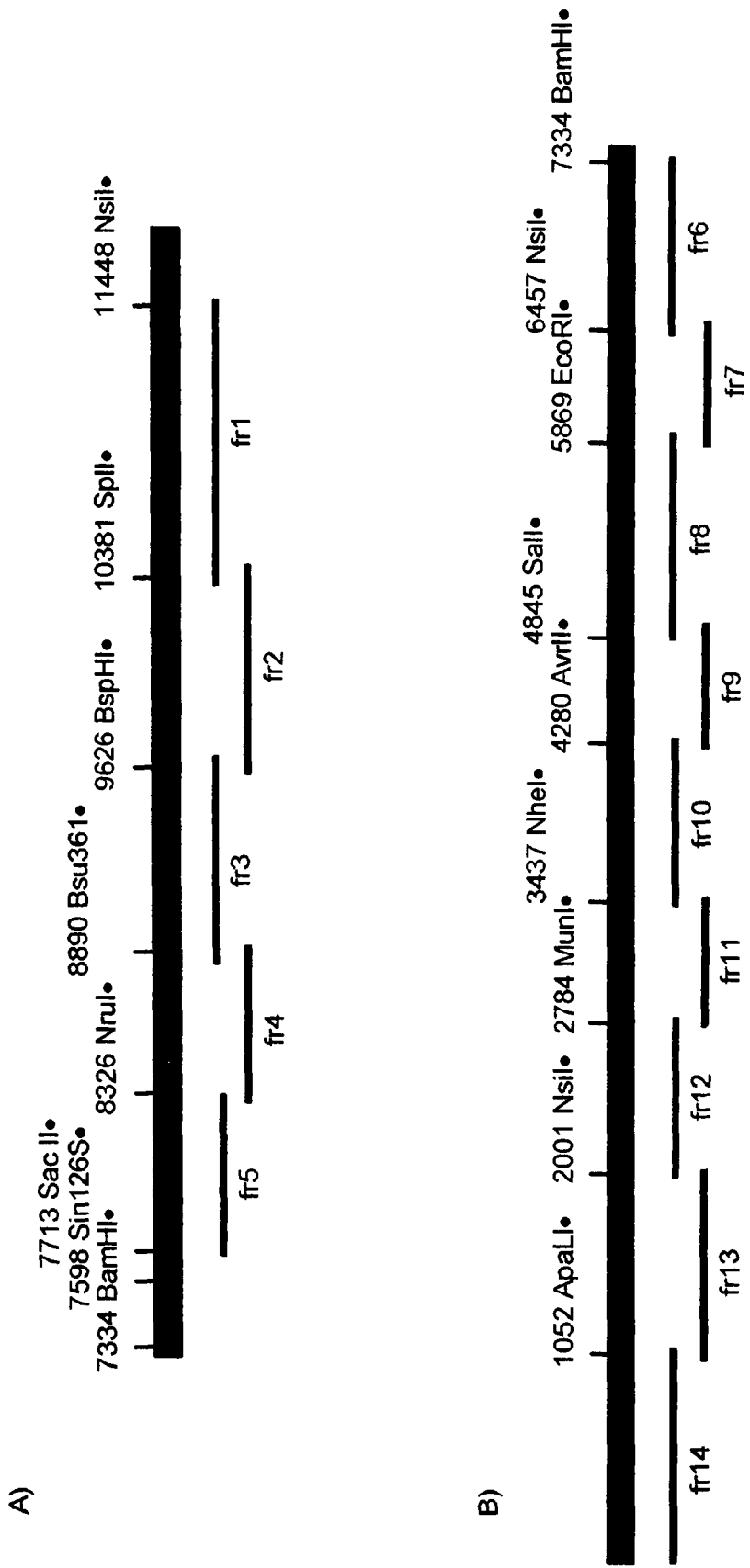
FIG. 2A describes a general cloning strategy for the genome of a human dendritic cell adapted alphavirus (e.g., Sindbis virus) variant.
Figure 3:
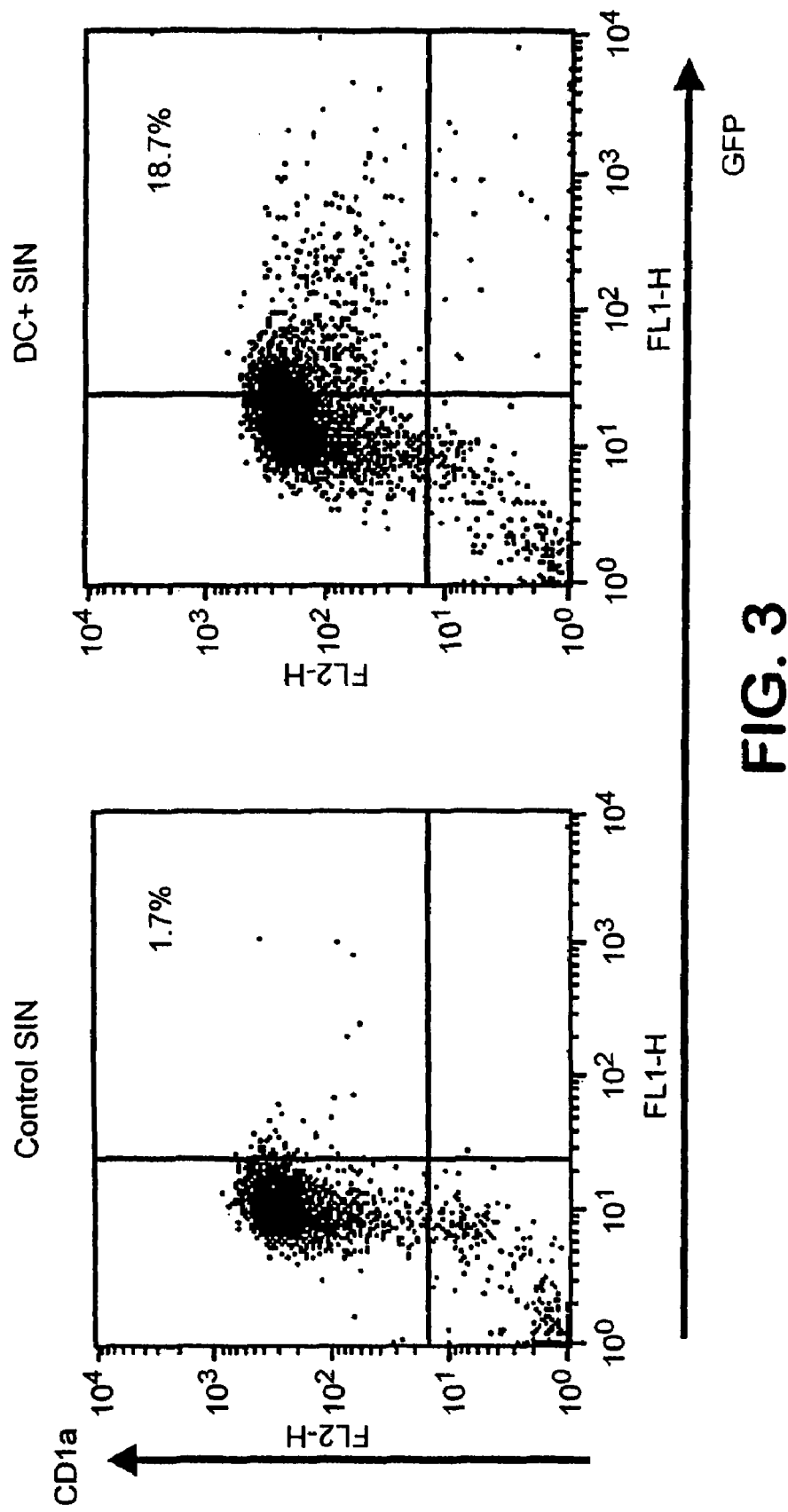
FIG. 3 shows Sindbis-GFP vector infection of human dendritic cells.
Figure 4:
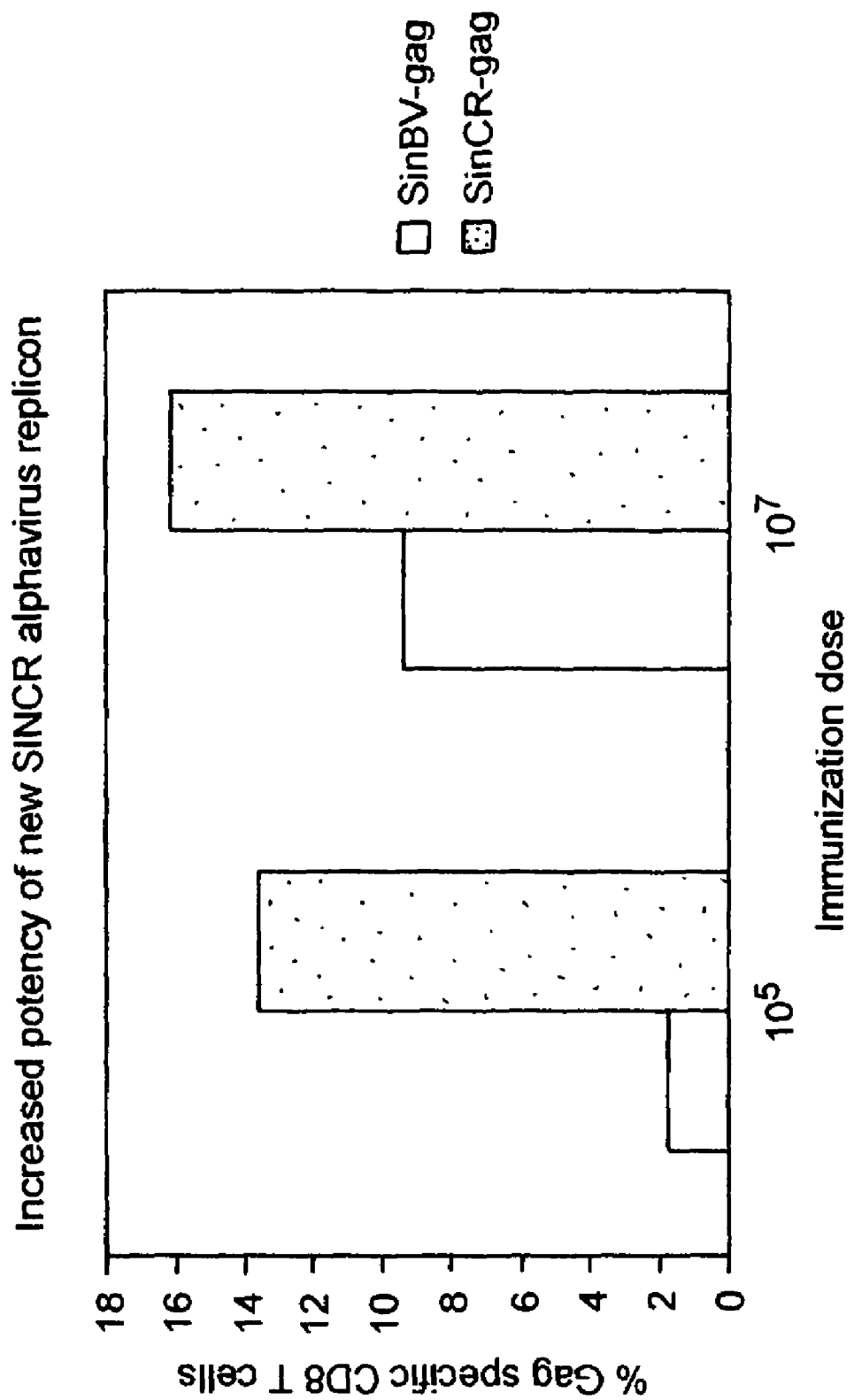
FIG. 4 shows increased efficiency of human DC infection by a SIN-GFP vector with SinDCChiron-derived envelope glycoproteins, as compared to glycoproteins from another DC variant of Sindbis virus.
Figure 5:
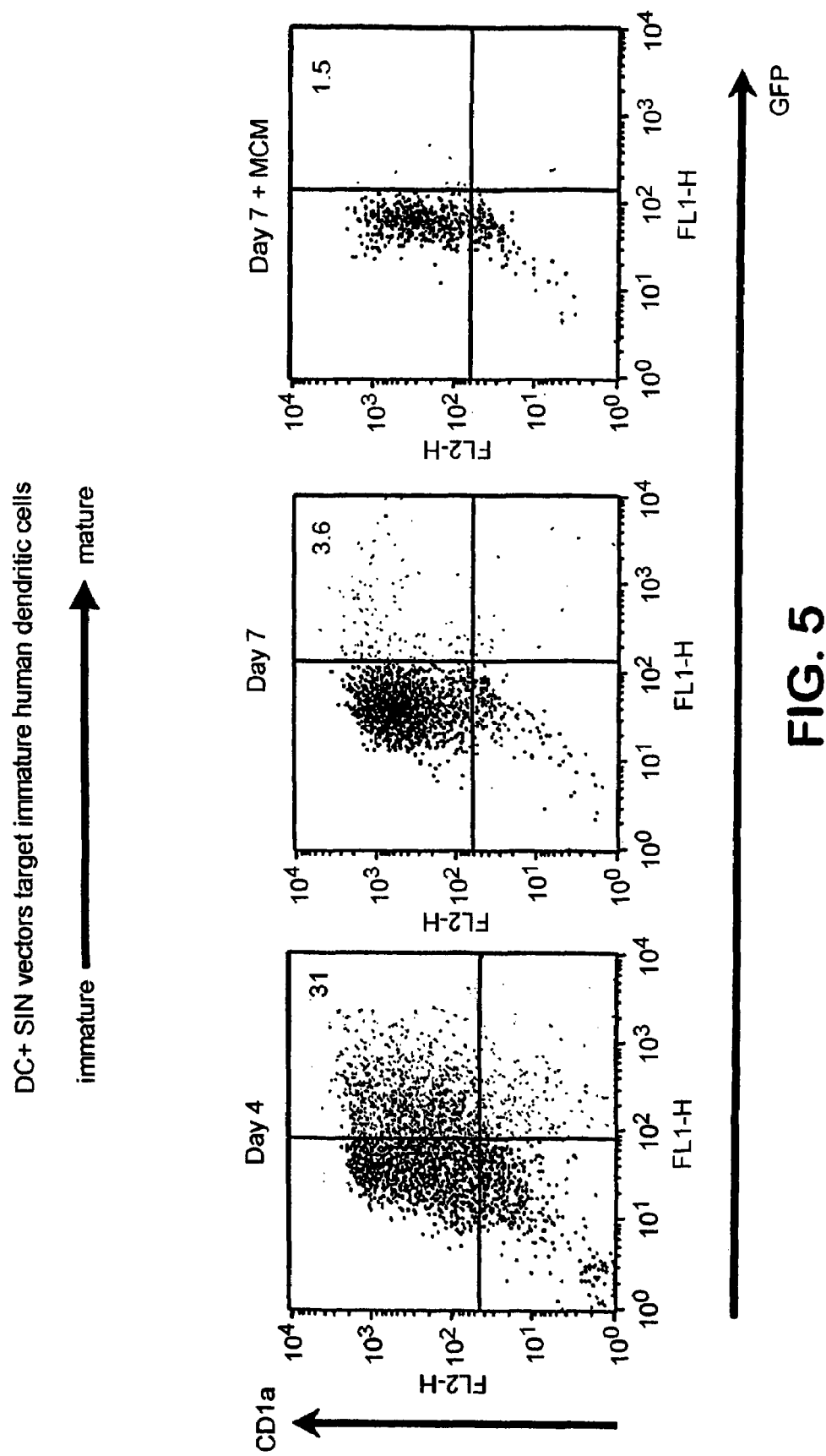
FIG. 5 shows that SIN-GFP vectors with DC adapted glycoproteins specifically target immature human dendritic cells as compared to mature DCs.

Approximately $10^7$ BHK-21 cells were infected with either the dendritic cell adapted virus seed stock or the large plaque virus seed stock at a MOI of 1 PFU/cell. At 24 hours post-infection, after development of CPE, total RNA was isolated from the cells using the TRIzol Reagent (GibcoBRL) according to the manufacturer's instructions. After purification, viral RNA was dissolved in nuclease-free water, aliquoted, and stored at −80° C. for later use in cDNA cloning (FIG. 2A).

Synthesis of cDNA was accomplished by PCR amplification, using the primer sets shown below. (Sindbis nucleotide numbering indicated for each primer):

Primer pairs 1-5 were used for cloning of the virus structural genes, while pairs 6-14 were for the virus nonstructural genes. Oligonucleotides in pairs 1-5 contained additional sequences representing restriction enzyme sites for EcoRI and HindIII, which are not present in subgenomic RNA of Sindbis virus. Oligonucleotides 6-14 contained sites for SacI and XhoI, which are not present in the whole genome of previously sequenced strains of Sindbis virus (these sites are underlined).

Each reverse transcription (RT) reaction was performed in a 50 ul volume using the SuperscriptII enzyme (GibcoBRL), according to the manufacturer's instructions. Reaction mixtures contained the amount of RNA equivalent to $10^6$ cells and 50 pmoles of each primer shown below.

Mixture1: primers 1, 3 and 5
Mixture2: primers 2 and 4
Mixture3: primers 6, 9 and 12
Mixture4: primers 8, 11 and 14

| # | Sequence | Position | SEQ ID NO |
|---|----------|----------|-----------|
| 1 | CCAC*AAGCTT*GATCTAATGTACCAGCCTGATGC | 11472-11450 | (SEQ ID NO: 3) |
| 1.1 | CCAC*GAATTC*AGCCAGATGAGTGAGGC | 10364-10381 | (SEQ ID NO: 4) |
| 2 | CCAC*AAGCTT*CAATTCGACGTACGCCTCAC | 10394-10375 | (SEQ ID NO: 5) |
| 2.1 | *CCACGAATTC*ATATGGGAAATCATGAGCC | 9614-9634 | (SEQ ID NO: 6) |
| 3 | *CCACAAGCTT*CATAGACCCTCACTGGCTC | 9648-9630 | (SEQ ID NO: 7) |
| 3.1 | CCAC*GAATTC*AAGATTAGCACCTCAGGACC | 8878-8899 | (SEQ ID NO: 8) |
| 4 | CCAC*AAGCTT*CTACACGGTCCTGAGGTGC | 8908-8887 | (SEQ ID NO: 9) |
| 4.1 | CCAC*GAATTC*GTCCGATCATGGATAACTCC | 8294-8315 | (SEQ ID NO: 10) |
| 5 | CCAC*AAGCTT*GCGCCACCGAGGAC | 8347-8334 | (SEQ ID NO: 11) |
| 5.1 | CCAC*GAATTC*ACTGCCATGTGGAGGCC | 7797-7814 | (SEQ ID NO: 12) |
| 6 | CCAC*CTCGAG*TTTACCCAACTTAAACAGCC | 7368-7348 | (SEQ ID NO: 13) |
| 6.1 | CCAC*GAGCTC*GCGACATTCAATGTCGAATGC | 6426-6446 | (SEQ ID NO: 14) |
| 7 | CCAC*CTCGAG*GAACTCCTCCCAATACTCGTC | 6488-6468 | (SEQ ID NO: 15) |
| 7.1 | CCAC*GAGCTC*GACCTTGGAGCGCAATGTCC | 5843-5862 | (SEQ ID NO: 16) |
| 8 | CCAC*CTCGAG*TTTCGACGTGTCGAGCACC | 5900-5882 | (SEQ ID NO: 17) |
| 8.1 | CCAC*GAGCTC*GACCATGGAAGCAATCCGC | 4814-4832 | (SEQ ID NO: 18) |
| 9 | *CCACCTCGAG*ACGACGGGTTATGGTCGAC | 4864-4845 | (SEQ ID NO: 19) |
| 9.1 | CCAC*GAGCTC*CACGGAGACAGGCACCGC | 4246-4264 | (SEQ ID NO: 20) |
| 10 | CCAC*CTCGAG*GATCACTTTCTTTCCTAGGCAC | 4299-4277 | (SEQ ID NO: 21) |
| 10.1 | CCAC*GAGCTC*GAACTCTCCCGTAGATTTCC | 3407-3427 | (SEQ ID NO: 22) |
| 11 | CCAC*CTCGAG*ATCAAGTTGTGTGCCCTTCC | 3464-3445 | (SEQ ID NO: 23) |
| 11.1 | CCAC*GAGCTC*CCAGGGGATATCATCCTGAC | 2742-2761 | (SEQ ID NO: 24) |
| 12 | CCAC*CTCGAG*GCTGTCATTACTTCATGTCCG | 2825-2804 | (SEQ ID NO: 25) |
| 12.1 | CCAC*GAGCTC*GAACCGCAAACTATACCACATTGC | 1976-1999 | (SEQ ID NO: 26) |
| 13 | CCAC*CTCGAG*CTTGTACTGCTCCTCTTCTG | 2042-2023 | (SEQ ID NO: 27) |
| 13.1 | CCAC*GAGCTC*GGAGAACGGGTATCGTTCC | 1029-1047 | (SEQ ID NO: 28) |
| 14 | CCAC*CTCGAG*CCGGGATGTACGTGCAC | 1069-1052 | (SEQ ID NO: 29) |
| 14.1 | CCAC*GAGCTC*ATTGACGGCGTAGTACACAC | 1-20 | (SEQ ID NO: 30) |

RT reactions were frozen and then used directly for PCR amplification. PCR reactions were performed using Vent DNA polymerase (NEB) as recommended by the manufacturer. Each 50 ul PCR reaction contained 3 ul of RT mixtures described above and 50 pmoles of primers. A total of 14 reactions were performed (Table 1).

TABLE 1

| N of fragment | Primers | N of RT reaction. | Length of the fragment (bp.) |
| --- | --- | --- | --- |
| 1 | 1 and 1.1 | 1 | 1128 |
| 2 | 2 and 2.1 | 2 | 800 |
| 3 | 3 and 3.1 | 1 | 789 |
| 4 | 4 and 4.1 | 2 | 644 |
| 5 | 5 and 5.1 | 1 | 670 |
| 6 | 6 and 6.1 | 3 | 962 |
| 7 | 7 and 7.1 | 3 | 666 |
| 8 | 8 and 8.1 | 4 | 1107 |
| 9 | 9 and 9.1 | 3 | 638 |
| 10 | 10 and 10.1 | 3 | 912 |
| 11 | 11 and 11.1 | 4 | 743 |
| 12 | 12 and 12.1 | 3 | 870 |
| 13 | 13 and 13.1 | 3 | 1034 |
| 14 | 14 and 14.1 | 4 | 1088 |

PCR reactions for fragments 1-5 were performed using the following conditions: 12 cycles of 95° C. for 30 seconds, 56° C. for 30 seconds and 74° C. for 90 seconds. For fragments 6-14, the number of cycles was changed from 12 to 15. A small aliquot of each reaction mixture was analyzed by agarose gel electrophoresis to confirm the presence of the fragments of the expected size. The rest was extracted with phenol-chloroform and DNA fragments were precipitated using ethanol.

For cloning, fragments 1-5 were digested with HindIII and EcoRI, and then ligated with plasmid pRS2 (pUC19 with additional restriction sites in polylinker) treated with the same enzymes. Fragments 6-14 were digested with SacI and XhoI and ligated with the same pRS2 plasmid treated with SacI and XhoI. All recombinant plasmids were transformed into the E coli XL-1 Blue strain (Stratagene, La Jolla, Calif.).

In addition, cDNA clones representing the subgenomic promoter region and 3'-end nontranslated regions also were generated using the following primer pairs:

```
YSIN1F
5'-GATTCGGTTACTTCCACAGC         (SEQ ID NO: 31)

YSIN1R
5'-ACTGACGGCTGTGGTCAGTT         (SEQ ID NO: 32)

YSIN2F
5'-GATGTACTTCCGAGGAACTG         (SEQ ID NO: 33)

(SEQ ID NO: 34)
YSIN2R
5'-CCACAAGCTTGAAATGTTAAAAACAAAATTTTGT
```

Three positive colonies for each transformation were grown in 40 ml of 2×YT media supplemented with ampicillin (200 μg/ml), plasmids were purified using a QIAGEN kit according to the manufacturer's instructions, and the insertions were sequenced. By comparison of sequences from three independent clones, the genome sequence of each virus was determined (FIGS. 2B and 2C) and compared to published sequences for other Sindbis virus strains. Correct cDNA fragments for each virus (based on consensus of the three independent clones) were designated p1-p14 correspondingly.

Sequence data demonstrated that the SinDCChiron (also known as DC+) and SinChironLP (also known as LP) strains differed at only a single amino acid residue, throughout their entire genomes. This determinant for efficient infection of human dendritic cells, and in particular immature human DC, was located at E2 glyco protein residue 160, with the strains containing the amino acids Gly or Glu, respectively. Therefore, substitution of Gly for Glu at E2 160 alone is responsible for conferring the human DC-adapted phenotype. Additional amino acid substitutions, deletions or insertions at, or in close proximity to, this site can be readily generated by standard site-directed mutagenesis protocols, and when inserted into a full-length cDNA clone described below, also may produce the same human DC adapted growth characteristics.

Example 2

Construction of a Full-Length cDNA Clone, Vectors and Packaging Cassettes from Human Dendritic Cell Adapted Alphaviruses The construction of a full-length cDNA clone, replicon vectors, and structural protein expression (packaging) cassettes from a human dendritic cell adapted alphavirus, such as SinDCchiron virus, is readily accomplished by one of skill in the art using the teachings provided below, as well as those previous teachings provided by U.S. Pat. Nos. 5,814,482, 5,789,245 and 5,843,723. Vector replicon construction from clones of the SinDCchiron virus was accomplished using clones p1-p14 (Example 1) as follows. An ApaI-MscI fragment, containing the promoter for SP6 RNA polymerase and start of the Sindbis virus genomic RNA, was ligated with the MscI-XhoI fragment of cloned fragment 14 in ApqI-XhoI digested plasmid pRS2. The resulting plasmid was named p15. Next, the SacI-EcoRI fragment of p8, the EcoRI-NsiI fragment of p7 and the NsiI-XhoI fragment of p6 were ligated into SacI-XhoI digested pRS2. The resulting plasmid was named p16. Next, the SacI-MunI fragment of p12, the MunI-NheI fragment of p11 and the NheI-XhoI fragment of p11 were ligated into SacI-XhoI digested pRS2 plasmid. The resulting plasmid was named p17. The ApaI-ApaLI fragment of p15 and the ApaLI-XhoI fragment of p13 then were ligated into ApaI-XhoI treated pRS2, resulting in the plasmid named p18. Next, the ApaI-NsiI fragment of p18 and the NsiI-XhoI fragment of p17 were ligated together in ApaI-XhoI treated pRS2. The resulting plasmid was named p19. Finally, the ApaI-AvrII fragment of p19, the AvrII-SalGI fragment of p9 and the SalGI-BamHI fragment of p16 were ligated together into an ApaI-BamHI treated Sindbis replicon vector expressing the GFP reporter (see Dubensky et al., J. Virol. 70:508-519, 1996, and U.S. Pat. No. 5,843,723). The resulting newly constructed replicon vector expressing GFP reporter was designated SINCR-GFP (also known as DCSP6SINgfp).

Construction of a defective helper-based packaging cassette from clones of the SinDCchiron virus may be accomplished as follows. A BamHI-SacII fragment containing the Sindbis virus subgenomic promoter and 5' subgenomic NTR, from the previously described DH-BB helper plasmid (Bredenbeek et al., J. Virol. 67:6439-6446, 1993), a SacII-NruI fragment from clone p5 and a NruI-HindIII fragment from p4 are cloned together into BamHI-HindIII digested pRS2. The resulting plasmid is named p20. Next, the EcoRI-BspHI fragment of clone p3, the BspHI-SpII fragment of clone p2 and the SpII-NsiI fragment of clone p1 are cloned into EcoRI-HindIII digested pRS2. The resulting plasmid is named p21. Finally, the BamHI-Bsu36I fragment of p20 and the Bsu36I-NsiI fragment of p21 are cloned into BamHI-NsiI digested DH-BB helper plasmid, resulting in the final packaging construct named DCSP6SINdh.

Other variations of defective helper based structural protein expression cassettes (packaging constructs) can be readily constructed. These include cassettes that express the alphavirus structural protein genes in a "split" configuration, as well as RNA polymerase II based constructs for use in the derivation of stable packaging cell lines (see U.S. Pat. Nos. 5,789,245, 6,015,686, 6,015,694, 5,842,723, and 5,814,482). For example, SP6-based defective helpers were constructed to contain only the Sindbis virus envelope glycoprotein genes with a Ross River virus translation enhancer element. Construction of such plasmids was performed stepwise as follows.

The EcoRI-Bsu36 fragment from 4.4.2 and the Bsu36-HindIII fragment from 1.3.2 were cloned into EcoRI-HindIII digested pRS2 (designated cl201). The EcoRI-Bsu36 fragment from 4.4.2 and the Bsu36-HindIII fragment from 4.3.2 were cloned into EcoRI-HindIII digested pRS2 (designated cl202). The EcoRI-SplI fragment from 4.2.2 and the SplI-HindIII fragment from 1.1.2 were cloned into EcoR1-HindIII digested pRS2 (designated cl203). The EcoRI-BspHI fragment from cl 201 and the BspHI-HindIII fragment from cl203 were cloned into EcoRI-HindIII digested pRS2 (designated cl221). The EcoRI-BspHI fragment from cl 202 and the BspHI-HindIII fragment from cl203 were cloned into EcoRI-HindIII digested pRS2 (cl222). The StuI-NsiI fragment of cl221 and the BspHI-StuI fragment of tRNABB/Cdel3rrv (Frolov et al, 1997, J. Virol. 71:2819-2829) were cloned into BspHI-NsiI digested tRNABB/Cdel3rrv (designated cl231). The StuI-NsiI fragment of cl222 and the BspHI-StuI fragment of tRNABB/Cdel3rrv were cloned into BspHI-NsiI digested tRNABB/Cdel3rrv (designated cl232).

Figure 7:
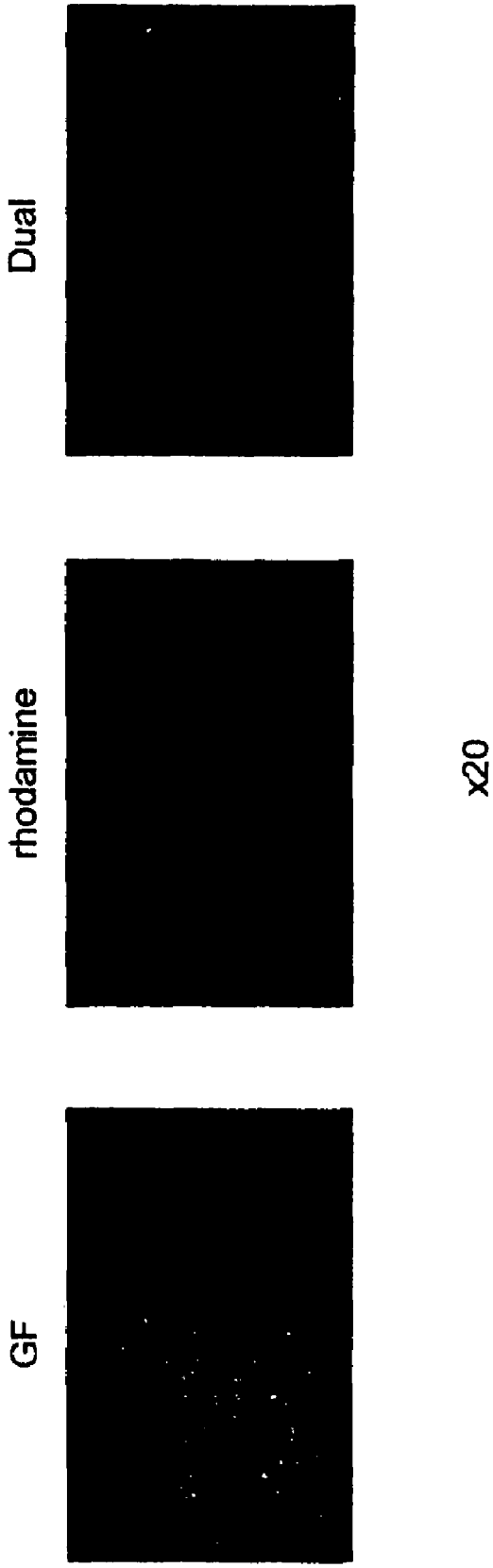
FIG. 7 shows microscopy of DC variant SIN-GFP vector infected cells that have trafficked to the lymph node after administration to mice

When used to package alphavirus vector replicons, the glycoprotein defective helper clone 232 (tRNABB/Cdel3rrvDC) will produce vector particles that efficiently infect human dendritic cells, particularly the immature population of DC, while the glycoprotein defective helper clone 231 (tRNABB/Cdel3rrvNDC) will produce vectors that do not efficiently infect human dendritic cells.

Alphavirus vector particles for use in testing human dendritic cell tropism, as well as for use in vivo (e.g., vaccine administration), may be generated using a variety of previously described methodologies. These methods include for example, co-transfection of in vitro transcribed replicon vector and defective helper packaging RNAs, co-transfection of plasmid DNA-based vector and packaging cassettes, and introduction of vector replicons into stable packaging cell lines (see for example, Dubensky et al., *J. Virol.* 70:508-519, 1996; Bredenbeek et al., *J. Virol.* 67:6439-6446, 1993; and U.S. Pat. Nos. 5,843,723 and 5,789,245).

As shown if FIGS. 3, 4, 5 and 8 Sindbis-GFP replicon vector that was packaged in the structural proteins from SinDCchiron virus acquired the ability to efficiently infect primary human dendritic cells, particularly immature dendritic cells. In these experiments, FACS analysis was performed as follows. Developing dendritic cells were harvested from culture, washed in PBS/1% FCS and enumerated by trypan blue exclusion staining. Non-specific binding was blocked by incubation with human Ig, and cells were incubated with propidium iodide to enable subsequent analysis of viable cells. Cells (1-10×$10^6$) were stained at 4° C. for 30 minutes with fluorochrome-conjugated antibodies to dissect the cell population susceptible to infection. The following antibodies (and their cellular specificities) were used: CD1a-PE (pan-dendritic cell), CD86-PE (antigen presenting cells: dendritic cells, macrophages, B cells), CD83-PE (mature dendritic cells), HLA-ABC-PE (many cell types), HLA-DR-PE (antigen presenting cells: dendritic cells, macrophages, B cells), CD3 (T cells), CD5 (T cells and B cells), CD16 (NK cells), CD11c-PE (dendritic cells and macrophages) and CD14-PE (monocytes). All antibodies were obtained from Becton Dickinson. Isotype matched controls were used to establish quadrant positions. Analysis was performed on a FACScan (Becton Dickinson), and the data acquired to a Macintosh 7100 computer. CellQuest 3.1 software was used to analyze and display data.

We found that immature human dendritic cells differentiated from monocytes for 3-5 days with IL4 and GMCSF were highly susceptible to infection with the DC-tropic Sindbis vector particles expressing GFP. The phenotype of the susceptible cell population, based on cell surface markers was $CD1a^+CD83^-CD14^-CD3^-CD86^+HLA\text{-}DR^+HLA\text{-}ABC^+CD11c^+$. Adherent macrophages were differentiated from monocytes with MCSF (50 U/ml; R&D Systems, Minneapolis, Minn.) for 6 days in 12-well Costar plates at 1.5×$10^6$ cells/ml. Adherent macrophages (HLA-$DR^+$) derived from these cultures were infected with particular Sindbis variant particles. Macrophages developed in this system are known in the field to be closely related to dendritic cells, and can function as dendritic cell precursors. Purified $CD3^+$ T cells were not infected at equivalent MOIs, and a subset of dendritic cell precursors ($HLA\text{-}DR^+CD14^{dim}CD3^-CD16^-CD1a^-CD5^-$ were infected when heterogeneous PBMC cultures were exposed to SIN replicon particles. Taken together, dendritic cells, and the macrophage and PBMC precursor populations were susceptible to infection with Sindbis particles, and T cells, B cells and NK cells were refractory to infection.

When similar studies were performed with mouse derived dendritic cells, it was demonstrated that the structural proteins from wild-type alphaviruses (for example, Sindbis virus, Semliki Forest virus) allow for efficient vector particle infection of mouse DC, but not human DC (see FIG. 8, SFV or SIN LP). Only by using modified or adapted structural proteins can these vector particles efficiently infect human dendritic cells (see SIN DC+).

Infection of human dendritic cells was receptor mediated and could be inhibited by an anti-virion rabbit polyclonal antibody. For example, GFP-expressing replicon particles packaged with the SinDCchiron structural proteins (2×$10^7$) were pre-incubated for 30 minutes with either anti-virion antibody or control rabbit polyclonal antibody recognizing mouse Ig (from Sigma, Cat #M-6024) at 1:100 dilution in PBS. Immature human dendritic cells (2×$10^5$; Day 3) were infected for 1 hour and analyzed 24 hours later for GFP expression. Anti-virion antibody blocked infection of dendritic cells by SinDCchiron particles, whereas non-specific antibody had no effect.

We next wished to determine whether alphavirus vector particles selected for human DC-tropism could be used as a method to induce maturation and activation in dendritic cells that have been transduced with the vector, either in vitro or in vivo. As shown in FIG. 9, human DC transduced in vitro with SIN-GFP vector particles, show significant up-regulation of the cell surface markers CD80, CD86, CD83, and MHC class II, which are known markers for maturation and activation. In addition, similar results were observed in vivo, for a mouse model. Following peripheral inoculation with SIN-GFP vector particles, the CD11c dendritic cells positive for GFP expression, were isolated from the draining lymph nodes and shown to have significant up-regulation of maturation and activation markers (e.g., MHC II).

To further demonstrate the ability of DC-tropic Sindbis-GFP particles to infect dendritic cells in vivo, we inoculated groups of 4 female Balb/C mice aged 8-10 weeks intradermally in the ear. The left ear was painted with 25 ul rhodamine B isothiocyanate (2% dissolved in acetone/dibutylpthalate) prior to injection with 25 ul SIN-GFP particles ($1.75 \times 10^7$ total particles in formulation buffer). The right ear was not painted with rhodmaine and was injected with SIN-GFP particles ($1.75 \times 10^7$) alone. Control groups received formulation buffer alone, and the left ear of each animal was painted with rhodamine. Two animals from each group were anesthetized and exsanguinated at 24 hours and 48 hours post injection, and the ears and draining mandibular node were harvested immediately into 1% paraformaldehyde. The tissues were fixed for 72 hours at 4° C. in the dark, before embedding in paraffin. Tissue sections (5 um) were prepared with a cryostat onto glass microscope slides and analyzed quantitatively with a laser scanning cytometer (Compucyte, Cambridge, Mass.), or photo-documented with a fluorescent microscope (Zeiss) linked to a CCD camera (FIGS. 6 and 7). The presence of cells with GFP and rhodamine in the draining lymph nodes provides strong evidence that migratory dendritic cells are infected with sindbis particles in the skin, and traffic to the node. The cells exhibit dendritic morphology and have numerous processes that contact neighboring cells in the node. No GFP expressing cells were detected in the control groups.

Figure 10:
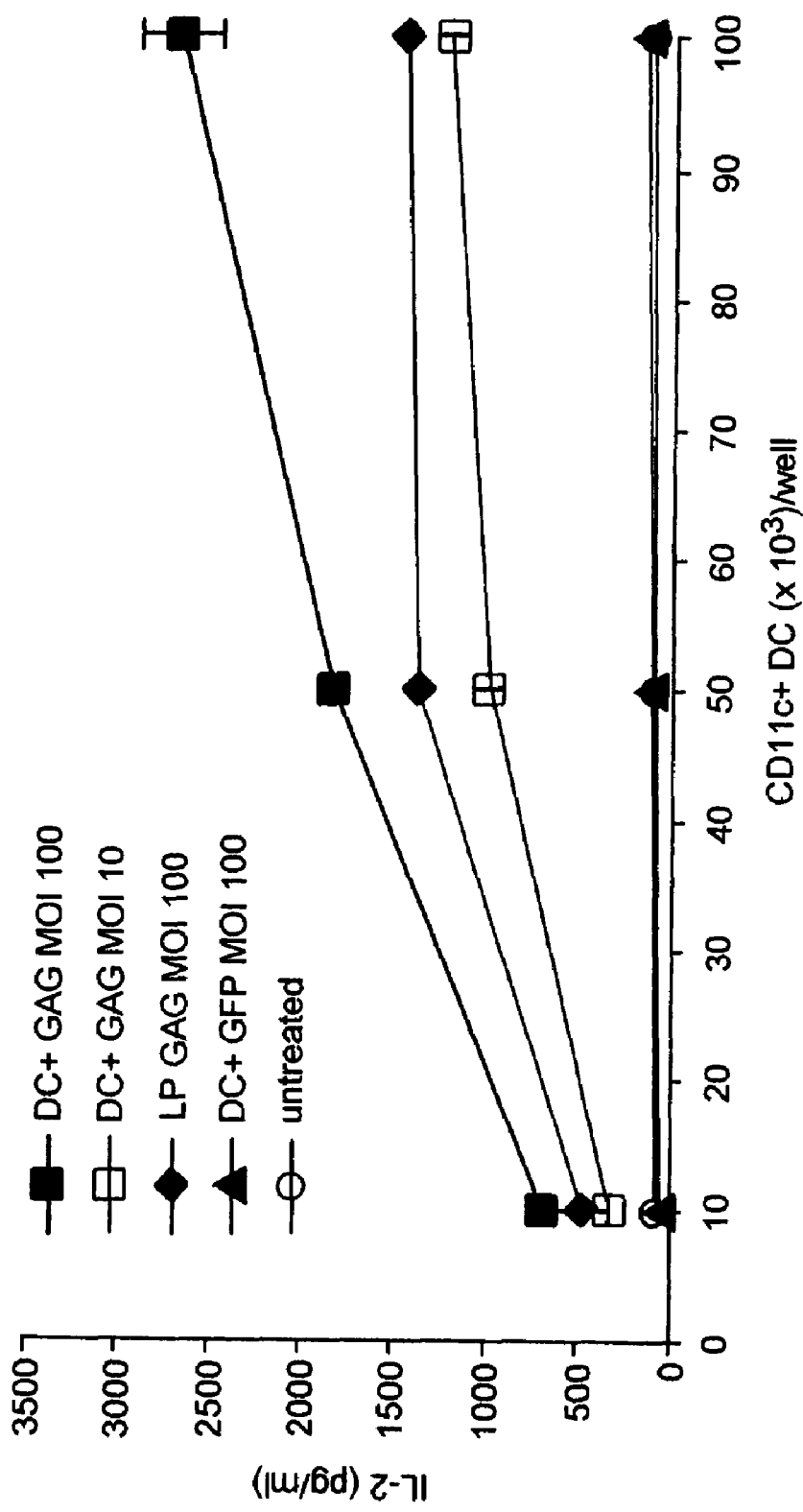
FIG. 10 shows the utility of human DC-adapted alphavirus vectors for in vitro assays that measure antigen presentation by transduced DC and stimulation of immune cells (e.g., T cells).

To demonstrate the utility of human DC-adapted alphavirus vectors as a "tool" in the development of in vitro assays for antigen presentation and stimulation of immune cells (e.g., class I restricted T cell responses), we utilized as a representative example, a murine T cell hybridoma assay (FIG. 10). The murine T cell hybridoma 12.2 was generated by fusion of splenocytes from HIV-gag-immunized CB6F1 mice with the BWZ 36 fusion partner, followed by cloning and selection based on IL-2 production in response to APCs loaded with HIV-derived peptides. The 12.2 T cell hybridoma specifically recognizes the peptide sequence AMQMLKETI (p7g) of the HIV-1 SF2 p24gag protein in the context of H-2Kd. The 12.2 T hybridoma produces IL-2 in a dose-responsive manner upon co-culture with p7g peptide-loaded H-2Kd DC and is unresponsive to DC loaded with another gag-derived peptide SQVTNPANI (gagb). The p7g gag-specific T cell hybridoma 12.2 was plated at $10^6$ cells/ml, $10^5$ cells/well in 96-well, U-bottom microtiter plates. Varying numbers of DC were added to wells for a total volume of 200 µl. As a positive control for DC function, DC from each condition were assayed in the presence of 1 ng/ml p7g peptide, as well as in media alone. Negative control wells containing DC or the T cell hybridoma alone were also included in each experiment and reliably yielded <20 pg/ml IL2. Each experimental condition was assayed in duplicate. After 24 hr co-culture, supernatants were removed and assayed for IL-2 production by ELISA according to manufacturer's instructions (Endogen, Woburn, Mass.). As a permanent source of homogeneous dendritic cell adapted virus, full-length cDNA clones, from which infectious SinDCchiron virus genomic RNA may be transcribed in vitro, may be constructed by using the DCSP6SINgfp vector as starting material. Specifically, the ApaI-SalGI and SalGI-BamHI fragments from DCSP6SINgfp vector, plus the BamHI-XhoI from the DCSP6SINdh packaging construct are cloned into pRS2 that has been digested with ApaI and XhoI. The resulting construct is designated DCSP6SINgen. Infectious virus seed stocks may be generated from this plasmid by linearization of the plasmid, transcription in vitro, and transfection of BHK-21 cells as extensively documented in previous publications (see for example Rice et al., *J. Virol.* 61:3809-3819, 1987; Dubensky et al., *J. Virol.* 70:508-519, 1996; Bredenbeek et al., *J. Virol.* 67:6439-6446, 1993; and U.S. Pat. No. 5,843,723).

Example 3

Prime-Boost Vaccine Strategies for Alphavirus Vectors

In order to be optimally efficacious, a vaccine for a given pathogenic agent (e.g., infectious disease agents such as viruses, bacteria, fungi, parasites) must stimulate a robust and broad-based antigen-specific immune response. The vaccinated individual will be resistant to development of sequalae characteristic of the infectious organism upon subsequent challenge, as a result of stimulation of residing memory cells and maturation into antigen-specific effector cells, which facilitate clearing of the offending infectious agent. Similarly, a therapeutic vaccine for a given infectious disease must also stimulate a robust and broad-based antigen-specific immune response, to clear or to diminish the extent of infectious disease.

Generally, vaccines are given in greater than one, and often in many, doses. The rationale of such an immunization strategy is to "boost" the "prime" response, resulting in a more durable immune response that is characterized by an increased capacity of an individual to resist challenge of an infectious organism. This increased resistance to challenge is due to a larger number of residing immune memory cells, often with specificity for a broader range of antigenic epitopes, corresponding to the infectious organism.

A broad-based antigen-specific immune response results when vaccination elicits both T-helper cell 1 (Th1) and T-helper cell 2 (Th2) responses. Proliferation of Th1 and Th2 cells are distinguished by their pattern of cytokine secretion, the Th1 subset corresponding to interleukin 2 (IL-2), and IFN-γ, and the Th2 subset corresponding to IL-4, IL-5, IL-6, and IL-10. Antigens expressed as a result of vaccination are presented to the immune system via dendritic cells (DCs), so-called "professional antigen presenting cells." DCs initiate and modulate the immune response. In particular, DCs are potent stimulators of B and T lymphocytes (for review, see Banchereau and Steinman, *Nature* 392:245-252, 1998). Stimulation of the T and B lymphocyte antigen-specific effectors occurs by presentation by the dendritic antigen presentation cells, in which processed antigen is displayed in conjunction with major histocompatibility complex (MHC) molecules of two alternative types (MHC class 1, or MHC class II), to T lymphocytes, via the T-cell antigen receptor. Antigen presentation via MHC class I results in a cellular CD8+ cell (cytotoxic T cell, CTL) response, whereas antigen presentation via MHC class II results in stimulation of CD4+ cells, and subsequently B lymphocytes, resulting in a humoral (antibody, Ab) response. Thus, the rationale of a "prime"-"boost" vaccination strategy is to elicit a broad and durable Th1 and Th2 antigen-specific immune response.

Traditional vaccination prime-boost strategies have used only a single modality for both the prime and boost steps, and may not, for particular infectious diseases, elicit a broad Th1/Th2 antigen-specific immune response. Thus, within the scope of the prevention invention, several "mixed" modalities of prime-boost regimes are disclosed wherein a variety of vaccinating compositions may be administered either as a "prime" or "boost", in conjunction with an alphavirus replicon vector (e.g., as recombinant particles, DNA or RNA) encoding a designated antigen. Such a prime-boost immunization strategy incorporating alphavirus vector replicons will elicit a much more durable and broad-based Th1/Th2 antigen-specific immune response in the vaccinated individual. The combined prime-boost immunization modalities may include, for example, plasmid DNA (formulated or non-formulated), ELVIS vector, recombinant alphavirus particles, other non-alphaviral vectors and recombinant protein. Any of these vaccine modalities, including the alphavirus vector replicons encoding a designated antigen, may be given with an adjuvant. Representative examples of adjuvants that can be utilized are MF59, poly-D-galactoside, alum, CpG oligonucleotides, or mono-phosphoro lipid.

To demonstrate the utility of prime-boost regimes according to the present invention, HIV gag was chosen as an example antigen. HIV gag was expressed by plasmid DNA vectors, ELVIS vector and alphavirus vector particles, and also produced as a recombinant protein. Other antigens from HIV, as well as antigens from other pathogenic agents (for example HCV), similarly may be used by one of skill in the art based on the teachings of the present invention.

A. Construction of HIV gag and Envelope Expression Vectors

The HIV gag coding sequence was selected from the HIV-1SF2 strain (Sanchez-Pescador, R., et al., *Science* 227(4686): 484-492, 1985; Luciw, P. A., et al., U.S. Pat. No. 5,156,949, issued Oct. 20, 1992, herein incorporated by reference; Luciw, P. A., et al., U.S. Pat. No. 5,688,688, Nov. 18, 1997). These sequences have been used directly or first manipulated to maximize expression of their gene products. For maximization of expression, the HIV-1 codon usage pattern was modified so that the resulting nucleic acid coding sequence was comparable to codon usage found in highly expressed human genes. The HIV codon usage reflects a high content of the nucleotides A or T as third base of the codon-triplet. The effect of the HIV-1 codon usage is a high AT content in the DNA sequence that could result in a decreased translation ability and instability of the mRNA. In comparison, highly expressed human codons prefer the nucleotides G or C as the third base. The gag coding sequence therefore was modified to be comparable to codon usage found in highly expressed human genes.

The DNA fragment for gag was cloned into the eukaryotic expression vector pCMVKm2, derived from pCMV6a (Chapman et al., *Nuc. Acids Res.* 19:3979-3986, 1991) and comprising a kanamycin selectable marker, a ColE1 origin of replication, a CMV promoter enhancer and Intron A, followed by cloning sites for insertion of sequences, followed by a polyadenylation signal derived from bovine growth hormone. The gag sequence-containing vector was designated pCMVKm2.GagMod.SF2. This plasmid was deposited Jan. 18, 1999, with the Chiron Corporation Master Culture Collection, Emeryville, Calif., 94662-8097, and with the American Type Culture Collection, 10801 University Boulevard, Manassas, Va. 20110-2209.

The DNA fragment encoding HIV gag was then cloned into an alphavirus plasmid DNA vector (ELVIS), and replicon vectors (SINBV and SINCR) to be used for the generation of recombinant alphavirus particles. Specifically, a construct for in vitro transcription of Sindbis virus RNA vector replicons (pRSIN-luc; Dubensky et al., *J Virol.* 10:508-519, 1996) was modified to contain a PmeI site for plasmid linearization and a polylinker for insertion of heterologous genes. First, a polylinker was generated using two oligonucleotides that contain the sites XhoI, PmlI, ApaI, NarI, XbaI, and NotI.

(SEQ ID NO: 35)
XPANXNF:
5'GCA CGT GGG CCC GGC GCC TCT AGA GC (SEQ ID NO: 36)
XPANXNR:
5'GCT CTA GAG GCG CCG GGC CCA CGT GC

The plasmid pRSIN-luc (Dubensky et al., supra) then was digested with XhoI and NotI to remove the luciferase gene insert, blunt-ended using Klenow and dNTPs, and ligated with the oligonucleotides that were annealed to each other. The resulting construct was digested with NotI and SacI to remove the minimal Sindbis 3'-end sequence and $A_{40}$ tract, and ligated with an approximately 0.4 kbp fragment from pKSSIN1-BV (WO 97/38087), obtained by digestion with NotI and SacI. The fragment contained the complete Sindbis virus 3'-end, an $A_{40}$ tract and a PmeI site for linearization. This replicon vector construct was designated SINBVE. The other replicon vector, SINCR, was described previously in example 2.

The HIV gag coding sequence was obtained from the parental pCMVKm2.GagMod.SF2 plasmid by digestion with EcoRI, blunt-ending with Klenow and dNTPs, purification with GeneCleanII, and digestion with SalI. The HIV gag-coding fragment then was ligated into the SINBVE vector that had been digested with XhoI and PmlI. The resulting vector was designated SINBV-gag. In parallel, the same HIV gag fragment was inserted into the new replicon of the present invention, by ligating with SINCR-GFP vector that had been digested with NotI and blunt-ended, followed by digestion with XhoI, to remove the GFP reporter gene insert. This vector was designated SINCR-gag. Vector RNA replicons were packaged into recombinant alphavirus particles by using previously described methods (see for example Dubensky, et al., *J. Virol.* 70:508-519, 1996; Polo et al., *PNAS* 96:4598-4603; and U.S. Pat. Nos. 5,789,245, 5,842,723, and 6,015,694, which are incorporated by reference in their entirety).

Figure 11:
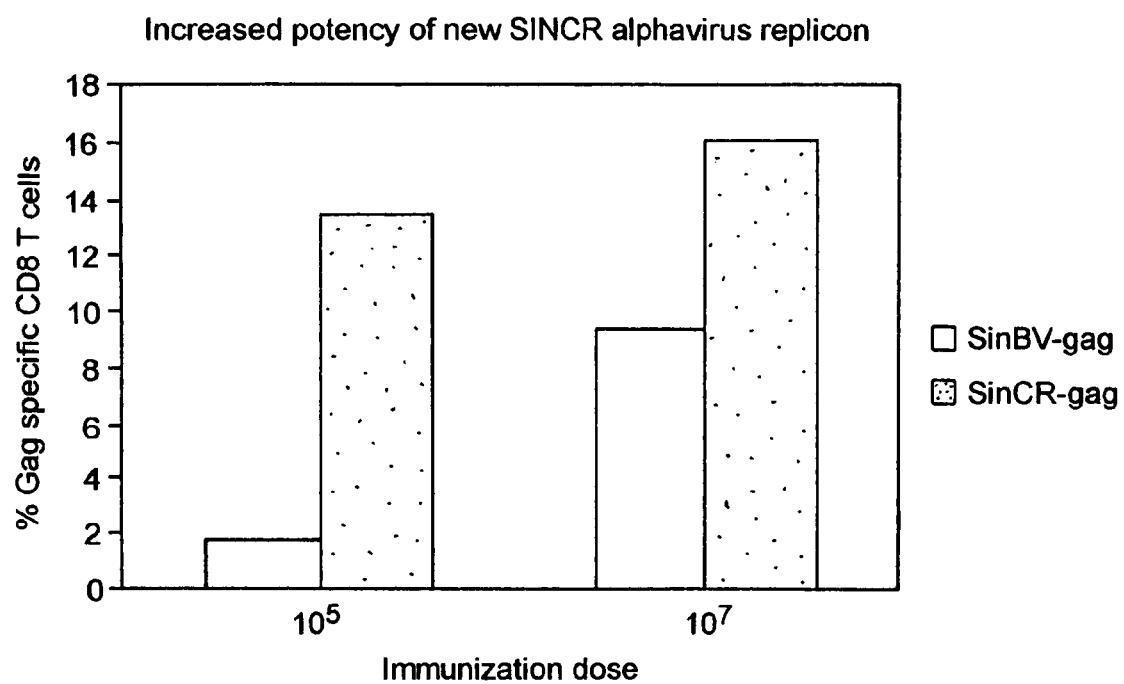
FIG. 11 is a graph comparing immune induction using recombinant alphavirus particles containing either the new SINCR replicon or a wild-type SINBV replicon.

The construction of a new SIN vector replicon utilizing the nonstructural gene sequences obtained from SinDCchiron virus (ATCC# VR-2643) or SinChironLP virus, described in FIGS. 2B and 2C, resulted in a replicon that had superior properties as compared to a replicon derived from wild-type SIN virus (e.g., ATCC# VR-2526). These properties include, but are not limited to, enhanced expression in human dendritic cells, increased packaging into recombinant alphavirus particles at levels as much as 10-fold over wild-type replicons, and the ability to induce a more robust immune response following immunization of animals. For example, FIG. 11 compares the induction of HIV gag specific CD8 T cells in mice following immunization with DC-tropic vector particles containing either the new SIN replicon (SINCR) or a previously described wild-type SIN replicon (SINBV). At doses of either $10^5$ or $10^7$ IU, the SINCR replicon that contains nonstructural gene sequences from SinDCchiron virus and SinChironLP virus is clearly more potent at immune induction.

For construction of an alphavirus DNA-based vector (ELVIS) expressing HIV gag, plasmid pDCMVSIN-β-gal (Dubensky et al., *J Virol.* 70:508-519, 1996) was digested with SalI and XbaI, to remove the beta-galactosidase gene insert, and the HIV gag gene was inserted after digestion and purification of the fragment from SINBV-gag. The resulting construct was designated pDSIN-Gag. Similarly, constructs expressing HIV envelope (env) protein were made using the same replicon and ELVIS vector backbones. A variety of envelope sequences have been used for these constructions and the parental plasmids used for isolation of the env genes (e.g., pCMVgp160.modUS4, pCMVgp140.mut7.modSF162, pCMVgp140.mut8.modSF162) have been deposited with CMCC and ATCC.

Recombinant gag protein was obtained using a baculovirus expression system. A baculovirus shuttle vector containing the synthetic HIV gag sequence was constructed as follows. The synthetic HIV p55 gag expression cassette (described above) was digested with restriction enzyme SalI followed by incubation with T4-DNA polymerase. The resulting fragment was isolated and then digested with BamHI. The shuttle vector pAcCl3 (Munemitsu S., et al., *Mol Cell Biol.* 10(11):5977-5982, 1990) was linearized by digestion with EcoRV, followed by incubation with T4-DNA polymerase. The linearized vector was digested with BamHI, treated with alkaline phosphatase, and the fragment isolated from an agarose gel. The isolated 1.5 kb fragment was ligated with the prepared pAcCl3 vector, resulting in the clone designated pAcCl3-Modif.p55gag.

Generation of the recombinant baculovirus was achieved by co-transfecting 2 g of the HIV p55 gag shuttle vector with 0.5 g of linearized *Autographa californica* baculovirus (Ac-NPV) wild-type viral DNA into Spodoptera frugiperda (Sf9) cells (Kitts, P. A., Ayres M. D., and Possee R. D., *Nucleic Acids Res.* 18:5667-5672, 1990). The isolation of recombinant virus expressing HIV p55 Gag was performed according to standard techniques (O'Reilly, D. R., L. K. Miller, and V. A. Luckow, *Baculovirus Expression Vector: A Laboratory Manual*, W.H. Freeman and Company, New York, 1992).

Expression of the HIV p55 Gag was achieved using a 500 ml suspension culture of Sf9 cells grown in serum-free medium (Maiorella, et al, *Bio/Technology* 6:1506-1510, 1988) that had been infected with the HIV p55 Gag recombinant baculovirus at a multiplicity of infection (MOI) of 10. Forty-eight hours post-infection, the supernatant was separated by centrifugation and filtered through a 0.2 m filter. Aliquots of the supernatant were then transferred to Polyclear™ (Beckman Instruments, Palo Alto, Calif.) ultracentrifuge tubes, underlaid with 20% (wt/wt) sucrose, and subjected to 2 hours centrifugation at 24.00 rpm using a Beckman SW28 rotor.

The resulting pellet was suspended in Tris buffer (20 mM Tris HCl, pH 7.5, 250 mM NaCl, and 2.5 mM EDTA), layered onto a 20-60% (wt/wt) sucrose gradient, and subjected to 2 hours centrifugation at 40,000 rpm using a Beckman SW41ti rotor. The gradient was then fractionated starting at the top (20% sucrose) of the gradient into approximately twelve 0.75 ml aliquots. A sample of each fraction was electrophoresed on 8-16% SDS polyacrylamide gels and the resulting bands were visualized after commassie staining. Additional aliquots were subjected to refractive index analysis.

The results indicated that the p55 gag VLP banded at a sucrose density of range of 1.15-1.19 g/ml with the peak at approximately 1.17 g/ml. The peak fractions were pooled and concentrated by a second 20% sucrose pelleting. The resulting pellet was suspended in 1 ml of Tris buffer (described above). The total protein yield as estimated by Bicimchrominic Acid (BCA) (Pierce Chemical, Rockford, Ill.).

Recombinant HIV envelope proteins were expressed from stable mammalian cell lines, rather than from baculovirus systems. Chinese hamster ovary (CHO) cells were transfected with plasmid DNA encoding the synthetic HIV-1 env proteins using Mirus TransIT-LT1 polyamine transfection reagent (Pan Vera) according to the manufacturers instructions and incubated for 96 hours. After 96 hours, media was changed to selective media (F12 special with 250 g/ml G418) and cells were split 1:5 and incubated for an additional 48 hours. Media was changed every 5-7 days until colonies started forming at which time the colonies were picked, plated into 96 well plates and screened by gp120 Capture ELISA. Positive clones were expanded in 24 well plates and screened several times for Env protein production by Capture ELISA, as described above. After reaching confluency in 24 well plates, positive clones were expanded to T25 flasks (Corning, Corning, N.Y.). These were screened several times after confluency and positive clones were expanded to T75 flasks.

Positive T75 clones were frozen in LN2 and the highest expressing clones amplified with 0-5 M methotrexate (MTX) at several concentrations and plated in 100 mm culture dishes. Plates were screened for colony formation and all positive closed were again expanded as described above. Clones were expanded an amplified and screened at each step by gp120 capture ELISA. Positive clones were frozen at each methotrexate level. Highest producing clones were grown in perfusion bioreactors (3 L, 100 L) for expansion and adaptation to low serum suspension culture conditions for scale-up to larger bioreactors.

The following table shows capture ELISA data from CHO cells stably transfected with plasmid vectors carrying a cassette encoding synthetic HIV-SF162 Env polypeptides (e.g., mutated cleavage sites, modified codon usage and/or deleted hypervariable regions). Thus, stably transfected CHO cell lines which express Env polypeptides (e.g., gp120, gp140-monomeric, and gp140-oligomeric) have been produced.

TABLE 2

CHO Cell Lines Expression Level of SF162 Envelope Constructs

| Constructs | CHO Clone # | MTX Level | Expression Level* (ng/ml) |
|---|---|---|---|
| gp120.modSF162 | 1 | 0 | 755-2705 |
|  | 2 | 0 | 928-1538 |
|  | 3 | 0 | 538-1609 |
| gp140.modSF162 | 1 | 20 nM | 180-350 |
| gp140.mut. | 1 | 20 nM | 164-451 |
| modSF162 | 2 | 20 nM | 188-487 |
|  | 3 | 20 nM | 233-804 |
| gp120.modSF162.delV2 | 1 | 800 nM | 528-1560 |
|  | 2 | 800 nM | 487-1878 |
|  | 3 | 800 nM | 589-1212 |
| gp140.modSF162.delV2 | 1 | 800 nM | 300-600 |
|  | 2 | 800 nM | 200-400 |
|  | 3 | 800 nM | 200-500 |
| gp140.mut. | 1 | 800 nM | 300-700 |
| modSF162.delV2 | 2 | 400 nM | 1161 |
|  | 3 | 800 nM | 400-600 |
|  | 4 | 400 nM | 1600-2176 |

*All samples measured at T-75 flask stage unless otherwise indicated

The results presented above demonstrate the ability of the constructs of the present invention to provide expression of Env polypeptides in CHO cells. Production of polypeptides using CHO cells provides (i) correct glycosylation patterns and protein conformation (as determined by binding to panel of MAbs); (ii) correct binding to CD4 receptor molecules; (iii) absence of non-mammalian cell contaminants (e.g., insect viruses and/or cells); and (iv) ease of purification.

B. Demonstration of Enhancement by Prime-Boost Vaccination Regimes

To demonstrate the ability to improve the immunogenicity of vaccines using a prime-boost regime that takes advantage of alphavirus vectors, a variety of different combinations may be used. For example, alphavirus vector particles may be administered as a prime followed by a recombinant protein or DNA vector boost. Alternatively, a plasmid DNA vector or ELVIS vector may be administered as a prime followed by an alphavirus vector particle boost. Also, an ELVIS vector prime may be administered with a recombinant protein or non-alphavirus (e.g., poxvirus) vector boost. It should be evident from the disclosure provided herein that a large number of different combinations of the above prime-boost elements may be interchanged, and that vectors encoding a variety of antigens may be similarly administered, using a variety of immunization routes.

Figure 12:
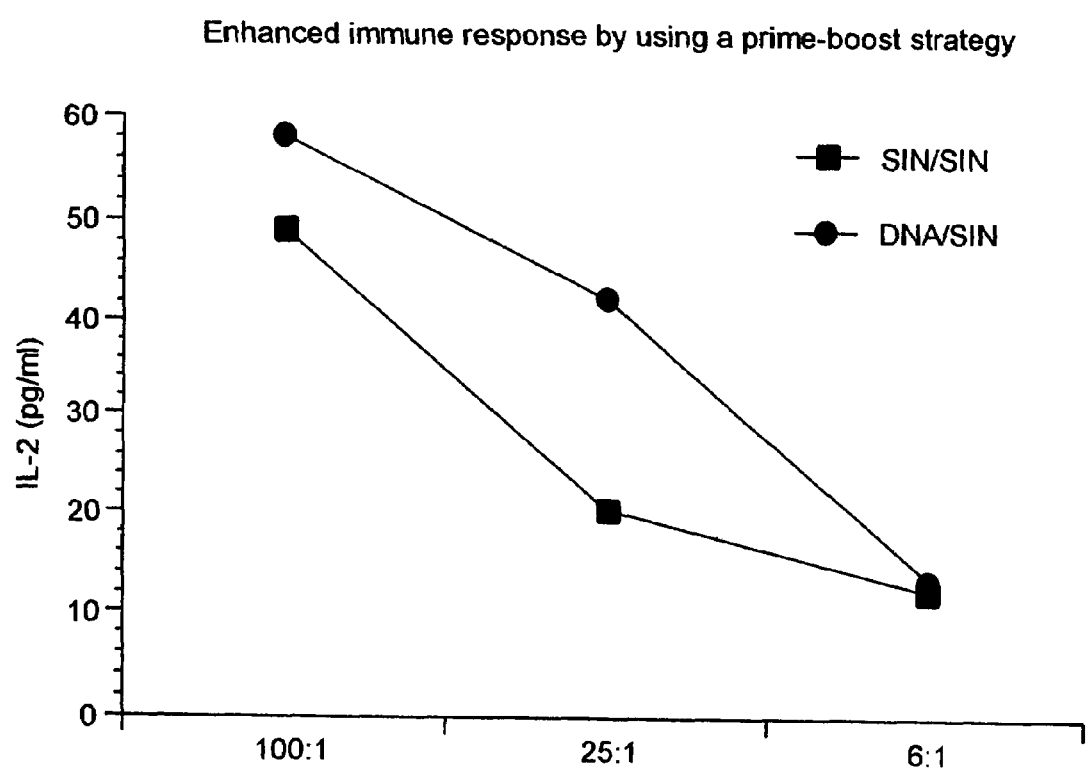
FIG. 12 is a graph that shows CTL enhancement by selected prime/boost vaccine strategies.

To illustrate the benefits of such prime-boost approaches, animal studies were performed using the SINBV-gag vector particles and pCMVKm2.GagMod.SF2 plasmid from above. These studies utilized a highly quantitative vaccinia challenge model to clearly elucidate CTL response differences in immunized animals. Mice were immunized intramuscularly in groups of three mice per sample, with DNA or alphavirus vector particles, in a 100 ul volume. Four weeks later, the mice were boosted with either plasmid DNA or vector particles (same or opposite vaccine compositions as initial priming immunization). Four weeks after boosting, the animals were then challenged intraperitoneally with $10^7$ PFU of recombinant vaccinia virus expressing HIV gag. Five days later, direct spleen cell CTL assays were performed against gag peptide-pulsed, $^{51}$Cr-labeled target cells. As shown in FIG. 12, a DNA prime—alphavirus vector particle boost regime resulted in greater immune induction than DNA alone or vector particles alone.

It should be appreciated, that the order of vaccine components delivered (e.g., alphavirus vector particles, DNA, ELVIS, recombinant protein), as well as the timing, dose and route of immunization, may be changed to include numerous possible combinations from the above. For example, the interval between prime and boost immunizations may range from no interval (simultaneous administration), to one or more days, preferably at least 14 days, and more preferably at least 28 days. In addition, the route of administration is not limited to intramuscular delivery; rather, other routes (for example, intradermal, intravenous, subcutaneous, intranasal, and oral) also may be utilized.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. An isolated Sindbis alphavirus which infects human dendritic cells, and which comprises an E2 glycoprotein comprising glycine in the position corresponding to residue 160, wherein residue 160 is numbered according to wild-type Sindbis alphavirus E2 glycoprotein encoded by a nucleic acid molecule of SEQ ID NO: 1 and wherein residue 160 in wild-type Sindbis alphavirus E2 glycoprotein is glutamic acid, with the proviso that said Sindbis alphavirus is not ATCC # VR-2526.

2. The isolated Sindbis alphavirus according to claim 1 wherein said alphavirus is ATCC No. VR-2643.

3. An isolated nucleic acid molecule which encodes the isolated Sindbis alphavirus according to claim 1.

4. A Sindbis alphavirus structural protein expression cassette, comprising a promoter operably linked to a nucleic acid sequence encoding at least one Sindbis alphavirus structural protein, wherein said nucleic acid sequence comprises a sequence encoding an E2 glycoprotein a glycine in the position corresponding to residue 160, wherein residue 160 is numbered according to wild-type Sindbis alphavirus E2 glycoprotein encoded by a nucleic acid molecule of SEQ ID NO: 1 and wherein residue 160 in wild-type Sindbis alphavirus E2 glycoprotein is glutamic acid.

5. An isolated alphavirus packaging cell, comprising a host cell and a Sindbis alphavirus structural protein expression cassette according to claim 4.

6. An isolated Sindbis alphavirus producer cell, comprising a packaging cell according to claim 5 and a vector selected from the group consisting of a Sindbis alphavirus RNA vector replicon, Sindbis alphavirus vector construct, and a eukaryotic layered vector initiation system.

7. A recombinant Sindbis alphavirus particle, comprising a particle produced from a producer cell line according to claim 6.

8. A recombinant Sindbis alphavirus particle, comprising a particle produced from a packaging cell line according to claim 5.

9. A recombinant Sindbis alphavirus particle which infects human dendritic cells, with the proviso that said recombinant Sindbis alphavirus particle is not derived from ATCC # VR-2526 wherein said particle comprises a Sindbis alphavirus E2 glycoprotein comprising glycine in the position corresponding to residue 160, wherein residue 160 is numbered according to wild-type Sindbis alphavirus E2 glycoprotein encoded by a nucleic acid molecule of SEQ ID NO: 1 and wherein residue 160 in wild-type Sindbis E2 glycoprotein is glutamic acid.

10. A method for introducing a heterologous nucleotide sequence into cells, comprising infecting said cells with a recombinant Sindbis alphavirus particle according to claim 9, such that said heterologous sequence is introduced into said cell.

11. The method according to claim 10 wherein said heterologous sequence is a sequence that encodes a protein.

12. The method according to claim 11 wherein said protein is an antigen from a pathogenic agent.

13. The method according to claim 12 wherein said antigen is from a virus, bacteria, parasite, or fungus.

14. The method according to claim 12 wherein said antigen is from a cancerous cell.

15. The method according to claim 11 wherein said protein is selected from the group consisting of IL-1, IL-2, IL-3, IL-4, IL-5, IL-6, IL-7, IL-8, IL-9, IL-10, IL-11, IL-12, IL-13, IL-14, IL-15, alpha-IFN, beta-IFN, gamma-IFN, G-CSF, and GM-CSF.

16. The method according to claim 10 wherein said heterologous sequence is a ribozyme or antisense.

17. The method according to claim 10 wherein said cell is infected ex vivo.

18. The method according to claim 10 wherein said cell is infected in vivo.

19. The method according to claim 10 wherein said cell is a population of cells comprising dendritic cells.

20. The method according to claim 19 wherein said dendritic cells are human dendritic cells.

21. The isolated nucleic acid molecule of claim 3 which comprises SEQ ID NO:2.

* * * * *

UNITED STATES PATENT AND TRADEMARK OFFICE
CERTIFICATE OF CORRECTION

PATENT NO. : 7,771,979 B2
APPLICATION NO. : 11/712044
DATED : August 10, 2010
INVENTOR(S) : Polo et al.

It is certified that error appears in the above-identified patent and that said Letters Patent is hereby corrected as shown below:

Title Page

The following cited references are added:

(56)                             References Cited

FOREIGN PATENT DOCUMENTS

| EP | 245078  | 1987-11-11 |
|----|---------|------------|
| WO | 9310814 | 1993-06-10 |
| WO | 9505853 | 1995-03-02 |
| WO | 9210578 | 1992-06-25 |
| WO | 8800472 | 1988-01-28 |
| WO | 9525788 | 1995-09-28 |
| WO | 9519990 | 1995-07-27 |
| WO | 9617072 | 1996-06-06 |
| WO | 9417813 | 1994-08-18 |
| WO | 9507994 | 1995-03-23 |
| WO | 9517525 | 1995-06-29 |
| WO | 9527044 | 1995-10-12 |
| WO | 9527069 | 1995-10-12 |
| WO | 9637616 | 1996-11-28 |
| WO | 9639830 | 1996-12-19 |
| WO | 9738087 | 1997-10-16 |
| WO | 9531565 | 1995-11-23 |
| WO | 9532733 | 1995-12-07 |
| WO | 9911808 | 1999-03-11 |
| WO | 9915641 | 1999-04-01 |
| WO | 9925859 | 1999-05-27 |

Signed and Sealed this
Third Day of May, 2011

David J. Kappos
*Director of the United States Patent and Trademark Office*

| | | |
|---|---|---|
| WO | 9417813 | 1994-08-18 |
| WO | 9716169 | 1997-05-09 |
| WO | 9724447 | 1997-07-10 |
| WO | 9730155 | 1997-08-21 |
| WO | 9744446 | 1997-11-27 |
| WO | 9813511 | 1998-04-02 |
| WO | 9815636 | 1998-04-16 |
| WO | 9826084 | 1998-06-18 |
| WO | 9836779 | 1998-08-27 |
| WO | 9853077 | 1998-05-20 |
| WO | 9909192 | 1999-02-25 |
| WO | 9918226 | 1999-04-15 |
| WO | 9925858 | 1999-05-27 |
| WO | 9930734 | 1999-06-24 |
| WO | 9426912 | 1994-11-24 |
| WO | 9206693 | 1992-04-30 |
| WO | 9102805 | 1991-03-07 |
| WO | 8910973 | 1989-11-16 |
| WO | 9224485 | 1995-09-14 |
| WO | 9731115 | 1997-08-28 |
| WO | 9748370 | 1997-12-24 |
| WO | 9834640 | 1998-08-13 |

(56) References Cited

OTHER PUBLICATIONS

Glasgow et al., Virology 1991, Vol. 185, pp. 741-748.
Glomb-Reinmund et al. J. Virol. 1998, Vol. 4281-4287.
Girard et al., "New Prospects for the Development of a Vaccine Against Human Immunodeficiency Virus Type 1. An Overview" CR Acad Sci Paris, Sciences de la vie 322:959-966, 1999.
Tunker et al., J. Virol. 1997 Vol. 71, pp. 6106-6212.
Gardner et al., J. Virol. Dec. 2000, Vol. 74, pp. 11849-11857.
Bungener et al., J. Leukocyte Biology Oct. 1998, Supp.[2], pp. K2-K2.
Berglund et al., "Semliki Forest Virus Expression System: Production of Conditionally Infectious Recombinant Particles" Bio/Technology 11:916-920, 1993.
Berglund et al., "Alphavirus as Vectors for Gene Delivery" Trends in Biotechnology 14:130-134, 1996.
Bredenbeek et al., "Animal RNA Virus Expression Systems" Seminars Virology 3:297-310, 1992.

Bredenbeek et al., "Sindbis Virus Expression Vectors: Packaging of RNA Replicons by Using Defective Helper RNAs," Journal Virology 67(11):6439-6446, 1993.

Brossart et al., "Virus-Mediated Delivery of Antigenic Epitopes into Dendritic Cells as a Means to Induce CTL," J. Immunology 7(158):327-3276, 1997.

Davis et al., "In Vitro Synthesis of Infectious Venezuelan Equine Encephalitis Virus RNA from a cDNA Clone: Analysis of a Viable Deletion Mutant," Virology 171:189-204, 1989.

Davis et al., "Protection Against Influenza in Mice by Vaccination with a Venezuelan Equine Encephalitis Virus Vector Expressing the HA Protein," J. Cell Biochem. Suppl. 19A 310, Abstract No. J2-308, 1995.

Dubensky et al., "Sindbis Virus DNA-Based Expression Vectors: Utility for in vitro and in vivo Gene Transfer," Journal Virology 70(1):508-519, 1996.

Dubuisson et al., "Sindbis Virus Attachment: Isolation and Characterization of Mutants with Impaired Binding to Vertebrate Cells," J. Virology 67(6):3363-3374, 1993.

Frolov et al., "Sindbis Virus Replicons and Sindbis Virus: Assembly of Chimeras and of Particles Deficient in Virus RNA," J. Virology 71(4):2819-2829, April, 1997.

Frolov et al., "Alphavirus-Based Expression Vectors: Strategies and Applications," Proc. Natl. Acad. Sci. USA 93:11371-11377, October, 1996.

Frolov et al., "Comparison of the effects of Sindbis Virus and Sindvis Virus Replicons on Host Cell Protein Synthesis and Cytopathogenicity in BHK Cells," J. Virology 68(3): 1721-1727, 1994.

Geigenmuller-Gnirke et al., "Complementation between Sindbis Viral RNAs Produces Infectious Particles with a Bipartite Genome," Proc. Natl. Acad. Sci. USA 88:3253-3257, 1991.

Hahn et al., "Infectious Sindbis Virus Transient Expression Vectors for Studying Antigen Processing and Presentation," Proc. Natl. Acad. Sci. USA 89:2679-2683, April, 1992.

Herweijer et al., "A Plasmid-Based Self-Amplifying Sindbis Virus Vector: Human Gene Therapy 6:1161-1167, 1995.

Huang et al., "RNA Viruses as Gene Expression vectors," Virus Genes 3(1):85-91, 1989.

Johanning et al., "A Sindbus Virus mRNA Polynucleotide Vector Achieves Prolonged and High Level Heterologous Gene Expression in vivo," Nucleic Acids Research 23(9):1495-1501, 1995.

Levis et al., "Promoter for Sindbis Virus RNA-Dependent Subgenomic RNA Transcription," J. Virology 64(4): 1726-1733, 1990.

Liljestrom and Garoff, "A New Generation of Animal Cell Expression Vectors Based on the Semliki Forest Virus Replicon," Bio/Technology 9:1356-1361, 1991.

Liljestrom, "Alphavirus Expression Systems," Current Opinion in Biotechnology 5:495-500, 1994.

London et al., "Infectious Enveloped RNA Virus antigenic Chimeras," Proc. Natl. Acad. Sci. USA 89:207-122, January, 1992.
Peters and Dalrymple, Chapter 26, entitled “Alphviruses” - “Virology” second edition, edited by B.N. Fields, D.M. Knipe et al., Raven Press, Ltd., New York, 1990.
Polo et al., “Stable Alphavirus Packaging Cell Lines for Sindbis Virus-and Semiliki Forest Virus-Derived Vectors,” Proc. Natl. Acad. Sci. USA 96:4598-4603, April, 1999.
Pushko et al., “Replicon-Helper Systems from Attenuated Venezuelan Equine Encephalitis Virus: Expression of Heterologous Genes in Vitro and Immunization Against Heterologous Pathogens in Vivo,” Virology 239:389-401, 1997.
Rice et al., “Production of Infectious RNA Transcripts from Sindbis Virus cDNA Clones: Mapping of Lethal Mutations, Rescue of a Temperature-Sensitive Marker, and in vitro Mutagenesis to Generate Defined Mutants,” J. Virology 61(12):3809-3819, 1987.
Rolls et al., “Novel Infectious Particles Generated by Expression of the Vesicular Stomatitis Glycoprotein from a self replicating RNA,” Cell. 79: 497-506, 1994.
Sarver and Stollar, “Sindbis Virus-Induced Cytopathic Effect in Clones of Aedes albopictus (Singh) Cells,” Virology 80:390-400, 1997.
Schlesinger, “Alphaviruses - Vectors for the Expression of Heterologous Genes,” Trends Biotechnology 11:18-22, 1993.
Smerdou and Liljestrom, “Two-Helper RNA System for Production of Recombinant Semliki Forest Virus Particles,” J. Virology 73(2): 1092-1098, February, 1999.
Strauss et al., “Complete Nucleotide Sequence of the Genomic RNA of Sindbis virus,” Virology 133:92-110, 1984.
Engelmayer et al., “Vaccinia Virus Inhibits the Maturation of Human Dendritic Cells: a Novel Mechanism of Immune Evasion,” J. Immunol. 163:6762-6768, 1999.
Xiong et al., “Sindbis Virus: an Efficient, Broad Host Range vector for Gene Expressing in Animal Cells,” Science 243(4895):1188-1191, March, 1989.
Zhou et al., “Self-Replicating Semliki Forest Virus RNA as Recombinant Vaccine,” Vaccine 12(16): 1510-1514, 1994.
Zhou et al., “Generation of Cytotoxic and Humoral Immune Responses by Nonreplicative Recombinant Semliki Forest virus,” Proc. Natl. Acad. Sci. USA 92:3009-3013, 1995.
Akbari et al., “DNA Vaccination: Transfection and Activation of Dendritic Cells as Key Events for Immunity,” J. Exp. Med. 189:169-178, 1999.
Banchereau et al., “Dendritic Cells and the Control of Immunity,” Nature 392:245-252, 1988.

CERTIFICATE OF CORRECTION (continued)
U.S. Pat. No. 7,771,979 B2

Bender et al., "Improved Methods for the Generation of Dendritic Cells from Nonproliferating Progenitors in Human Blood," J. Immunol. Methods 196:121-135, 1996.

Bhardwaj, "Interactions of Viruses with Dendritic Cells: a Double-Edged Sword," J. Exp. Med. 186:795-799, 1997.

Byrnes et al., "Binding of Sindbis Virus to Cell Surfact Heparan Sulfate," J. Virol. 72:7349-7356, 1998.

Cella et al., "Maturation, Activation, and Protection of Dendritic Cells Induced by Double-Stranded RNA," J. Exp. Med. 189:821-829, 1999.

Fugler-Vivier et al., "Measles virus Suppresses Cell-Mediated Immunity by Interfering with the Survival and Functions of Dendritic and T Cells," J. Exp. Med. 186:813-823, 1997.

Hariharan et al., "DNA Immunization Against Herpes Simplex Virus: Enhanced Efficacy Using a Sindbis virus-Based Vector," J. Virol. 72:950-968, 1998.

Klimstra et al., "Adaptation of Sindbis virus to BHK Cells Selects for Use of Heparan Sulfate as an Attachment receptor," J. Virol. 72:7357-7366, 1998.

MacDonald et al., "Role of Dendritic Cell Targeting in Venezuelan Equine Encephalitis Virus Pathogenesis," J. Virol. 74:914-922, 2000.

SEQUENCE LISTING

<160> NUMBER OF SEQ ID NOS: 36

<210> SEQ ID NO 1
<211> LENGTH: 11703
<212> TYPE: DNA
<213> ORGANISM: Sindbis virus

<400> SEQUENCE: 1

```
attgacggcg tagtacacac tattgaatca acagccgac  caattgcact  accatcacaa      60
tggagaagcc agtagtaaac gtagacgtag accccccagag tccgtttgtc gtgcaactgc     120
aaaaaagctt cccgcaattt gaggtagtag cacagcaggt cactccaaat gaccatgcta     180
atgccagagc attttcgcat ctggccagta aactaatcga gctggaggtt cctaccacag     240
cgacgatctt ggacataggc agcgcaccgg ctcgtagaat gttttccgag caccagtatc     300
attgtgtctg ccccatgcgt agtccagaag acccggaccg catgatgaaa tatgccagta     360
aactggcgga aaaagcgtgc aagattacaa acaagaactt gcatgagaag attaaggatc     420
tccggaccgt acttgatacg ccggatgctg aaacaccatc gctctgcttt cacaacgatg     480
ttacctgcaa catgcgtgcc gaatattccg tcatgcagga cgtgtatatc aacgctcccg     540
gaactatcta tcatcaggct atgaaaggcg tgcggacccct gtactggatt ggcttcgaca     600
ccacccagtt catgttctcg gctatggcag gttcgtaccc tgcgtacaac accaactggg     660
ccgacgagaa agtccttgaa gcgcgtaaca tcggactttg cagcacaaag ctgagtgaag     720
gtaggacagg aaaattgtcg ataatgagga agaaggagtt gaagcccggg tcgcgggttt     780
atttctccgt aggatcgaca ctttatccag aacacagagc cagcttgcag agctggcatc     840
ttccatcggt gttccacttg aatggaaagc agtcgtacac ttgccgctgt gatacagtgg     900
tgagttgcga aggctacgta gtgaagaaaa tcaccatcag tccgggatc  acgggagaaa      960 ccgtgggata cgcggttaca cacaatagcg agggcttctt gctatgcaaa gttactgaca     1020
cagtaaaagg agaacgggta tcgttccctg tgtgcacgta catcccggcc accatatgcg    1080
```

-continued

```
atcagatgac tggtataatg ccacggata tatcacctga cgatgcacaa aaacttctgg      1140
ttgggctcaa ccagcgaatt gtcattaacg gtaggactaa caggaacacc aacaccatgc      1200
aaaattacct tctgccgatc atagcacaag ggttcagcaa atgggctaag gagcgcaagg      1260
atgatcttga taacgagaaa atgctgggta ctagagaacg caagcttacg tatggctgct      1320
tgtgggcgtt tcgcactaag aaagtacatt cgttttatcg cccacctgga acgcagacca      1380
tcgtaaaagt cccagcctct tttagcgctt ttcccatgtc gtccgtatgg acgacctctt      1440
tgcccatgtc gctgaggcag aaattgaaac tggcattgca accaaagaag gaggaaaaac      1500
tgctgcaggt ctcggaggaa ttagtcatgg aggccaaggc tgcttttgag gatgctcagg      1560
aggaagccag agcggagaag ctccgagaag cacttccacc attagtggca gacaaaggca      1620
tcgaggcagc cgcagaagtt gtctgcgaag tggaggggct ccaggcggac atcggagcag      1680
cattagttga acccccgcgc ggtcacgtaa ggataatacc tcaagcaaat gaccgtatga      1740
tcggacagta tatcgttgtc tcgccaaact ctgtgctgaa gaatgccaaa ctcgcaccag      1800
cgcacccgct agcagatcag gttaagatca taacacactc cggaagatca ggaaggtacg      1860
cggtcgaacc atacgacgct aaagtactga tgccagcagg aggtgccgta ccatggccag      1920
aattcctagc actgagtgag agcgccacgt tagtgtacaa cgaaagagag tttgtgaacc      1980
gcaaactata ccacattgcc atgcatggcc ccgccaagaa tacagaagag gagcagtaca      2040
aggttacaaa ggcagagctt gcagaaacag agtacgtgtt tgacgtggac aagaagcgtt      2100
gcgttaagaa ggaagaagcc tcaggtctgg tcctctcggg agaactgacc aaccctccct      2160
atcatgagct agctctggag ggactgaaga cccgacctgc ggtcccgtac aaggtcgaaa      2220
caataggagt gataggcaca ccggggtcgg gcaagtcagc tattatcaag tcaactgtca      2280
cggcacgaga tcttgttacc agcggaaaga agaaaaattg tcgcgaaatt gaggccgacg      2340
tgctaagact gaggggtatg cagattacgt cgaagacagt agattcggtt atgctcaacg      2400
gatgccacaa agccgtagaa gtgctgtacg ttgacgaagc gttcgcgtgc cacgcaggag      2460
cactacttgc cttgattgct atcgtcaggc cccgcaagaa ggtagtacta tgcggagacc      2520
ccatgcaatg cggattcttc aacatgatgc aactaaaggt acatttcaat cacctgaaa      2580
aagacatatg caccaagaca ttctacaagt atatctcccg gcgttgcaca cagccagtta      2640
cagctattgt atcgacactg cattacgatg gaaagatgaa aaccacgaac ccgtgcaaga      2700
agaacattga aatcgatatt acaggggcca caaagccgaa gccaggggat atcatcctga      2760
catgtttccg cgggtgggtt aagcaattgc aaatcgacta tcccggacat gaagtaatga      2820
cagccgcggc ctcacaaggg ctaaccagaa aaggagtgta tgccgtccgg caaaaagtca      2880
atgaaaaccc actgtacgcg atcacatcag agcatgtgaa cgtgttgctc acccgcactg      2940
aggacaggct agtgtggaaa accttgcagg gcgacccatg gattaagcag ctcactaaca      3000
tacctaaagg aaactttcag gctactatag aggactggga agctgaacac aagggaataa      3060
ttgctgcaat aaacagcccc actccccgtg ccaatccgtt cagctgcaag accaacgttt      3120
gctgggcgaa agcattggaa ccgatactag ccacggccgg tatcgtactt accggttgcc      3180
agtggagcga actgttccca cagtttgcgg atgacaaacc acattcggcc atttacgcct      3240
tagacgtaat ttgcattaag ttttttcggca tggacttgac aagcggactg ttttctaaac      3300
agagcatccc actaacgtac catcccgccg attcagcgag gccggtagct cattgggaca      3360
acagcccagg aaccccgcaag tatgggtacg atcacgccat tgccgccgaa ctctcccgta      3420
```

```
gatttccggt gttccagcta gctgggaagg gcacacaact tgatttgcag acggggagaa   3480
ccagagttat ctctgcacag cataacctgg tcccggtgaa ccgcaatctt cctcacgcct   3540
tagtccccga gtacaaggag aagcaacccg gcccggtcga aaaattcttg aaccagttca   3600
aacaccactc agtacttgtg gtatcagagg aaaaaattga agctcccgt aagagaatcg    3660 aatggatcgc cccgattggc atagccggtg cagataagaa ctacaacctg gctttcgggt   3720
ttccgccgca ggcacggtac gacctggtgt tcatcaacat tggaactaaa tacagaaacc   3780
accactttca gcagtgcgaa gaccatgcgc cgaccttaaa aacccttttcg cgttcggccc   3840 tgaattgcct taacccagga ggcacccctcg tggtgaagtc ctatggctac gccgaccgca   3900
acagtgagga cgtagtcacc gctcttgcca gaaagtttgt cagggtgtct gcagcgagac   3960
cagattgtgt ctcaagcaat acagaaatgt acctgatttt ccgacaacta gacaacagcc   4020
gtacacggca attcaccccg caccatctga attgcgtgat tcgtccgtg tatgagggta    4080 caagagatgg agttggagcc gcgccgtcat accgcaccaa aagggagaat attgctgact   4140
gtcaagagga agcagttgtc aacgcagcca atccgctggg tagaccaggc gaaggagtct   4200
gccgtgccat ctataaacgt tggccgacca gttttaccga ttcagccacg gagacaggca   4260
ccgcaagaat gactgtgtgc ctaggaaaga aagtgatcca cgcggtcggc cctgatttcc   4320
ggaagcaccc agaagcagaa gccttgaaat tgctacaaaa cgcctaccat gcagtggcag   4380
acttagtaaa tgaacataac atcaagtctg tcgccattcc actgctatct acaggcattt   4440
acgcagccgg aaaagaccgc cttgaagtat cacttaactg cttgacaacc gcgctagaca   4500
gaactgacgc ggacgtaacc atctattgcc tggataagaa gtggaaggaa agaatcgacg   4560
cggcactcca acttaaggag tctgtaacag agctgaagga tgaagatatg gagatcgacg   4620
atgagttagt atggatccat ccagacagtt gcttgaaggg aagaaaggga ttcagtacta   4680
caaaaggaaa attgtattcg tacttcgaag gcaccaaatt ccatcaagca gcaaaagaca   4740
tggcggagat aaaggtcctg ttccctaatg accaggaaag taatgaacaa ctgtgtgcct   4800
acatattggg tgagaccatg gaagcaatcc gcgaaaagtg cccggtcgac cataacccgt   4860
cgtctagccc gcccaaaacg ttgccgtgcc tttgcatgta tgccatgacg ccagaaaggg   4920
tccacagact tagaagcaat aacgtcaaag aagttacagt atgctcctcc acccccttc    4980 ctaagcacaa aattaagaat gttcagaagg ttcagtgcac gaaagtagtc ctgtttaatc   5040
cgcacactcc cgcattcgtt cccgcccgta agtacataga agtgccagaa cagcctaccg   5100
ctcctcctgc acaggccgag gaggccccg aagttgtagc gacaccgtca ccatctacag    5160
ctgataacac ctcgcttgat gtcacagaca tctcactgga tatggatgac agtagcgaag   5220
gctcactttt ttcgagcttt agcggatcgg acaactctat tactagtatg gacagttggt   5280
cgtcaggacc tagttcacta gagatagtag accgaaggca ggtggtggtg gctgacgttc   5340
atgccgtcca agagcctgcc cctattccac cgccaaggct aaagaagatg gcccgcctgg   5400
cagcggcaag aaaagagccc actccaccgg caagcaatag ctctgagtcc ctccacctct   5460
cttttggtgg ggtatccatg tccctcggat caatttcga cggagagacg gccgccagg    5520 cagcggtaca accctgca acaggcccca cggatgtgcc tatgtctttc ggatcgtttt    5580
ccgacggaga gattgatgag ctgagccgca gagtaactga gtccgaaccc gtcctgtttg   5640
gatcatttga accgggcgaa gtgaactcaa ttatatcgtc ccgatcagcc gtatcttttc   5700
cactacgcaa gcagagacgt agacgcagga gcaggaggac tgaatactga ctaaccgggg   5760
taggtgggta catattttcg acggacacag gccctgggca cttgcaaaag aagtccgttc   5820
```

```
tgcagaacca gcttacagaa ccgaccttgg agcgcaatgt cctggaaaga attcatgccc    5880
cggtgctcga cacgtcgaaa gaggaacaac tcaaactcag gtaccagatg atgcccaccg    5940
aagccaacaa aagtaggtac cagtctcgta aagtagaaaa tcagaaagcc ataaccactg    6000
agcgactact gtcaggacta cgactgtata actctgccac agatcagcca gaatgctata    6060
agatcaccta tccgaaacca ttgtactcca gtagcgtacc ggcgaactac tccgatccac    6120
agttcgctgt agctgtctgt aacaactatc tgcatgagaa ctatccgaca gtagcatctt    6180
atcagattac tgacgagtac gatgcttact tggatatggt agacgggaca gtcgcctgcc    6240
tggatactgc aaccttctgc cccgctaagc ttagaagtta cccgaaaaaa catgagtata    6300
gagccccgaa tatccgcagt gcggttccat cagcgatgca gaacacgcta caaaatgtgc    6360
tcattgccgc aactaaaaga aattgcaacg tcacgcagat gcgtgaactg ccaacactgg    6420
actcagcgac attcaatgtc gaatgctttc gaaaatatgc atgtaatgac gagtattggg    6480
aggagttcgc tcggaagcca attaggatta ccactgagtt tgtcaccgca tatgtagcta    6540
gactgaaagg ccctaaggcc gccgcactat ttgcaaagac gtataatttg gtcccattgc    6600
aagaagtgcc tatggataga ttcgtcatgg acatgaaaag ggacgtgaaa gttacaccag    6660
gcacgaaaca cacagaagaa agaccgaaag tacaagtgat acaagccgca gaaccctgg    6720
cgactgctta cttatgcggg attcaccggg aattagtgcg taggcttacg gccgtcttgc    6780
ttccaaacat tcacacgctt tttgacatgt cggcggagga ttttgatgca atcatagcag    6840
aacacttcaa gcaaggcgac ccggtactgg agacggatat cgcatcattc gacaaaagcc    6900
aagacgacgc tatggcgtta accggtctga tgatcttgga ggacctgggt gtggatcaac    6960
cactactcga cttgatcgag tgcgcctttg gagaaatatc atccacccat ctacctacgg    7020
gtactcgttt taaattcggg gcgatgatga atccggaat gttcctcaca cttttttgtca    7080
acacagtttt gaatgtcgtt atcgccagca gagtactaga agagcggctt aaaacgtcca    7140
gatgtgcagc gttcattggc gacgacaaca tcatacatgg agtagtatct gacaaagaaa    7200
tggctgagag gtgcgccacc tggctcaaca tggaggttaa gatcatcgac gcagtcatcg    7260
gtgagagacc accttacttc tgcggcggat ttatcttgca agattcggtt acttccacag    7320
cgtgccgcgt ggcggacccc ctgaaaaggc tgtttaagtt gggtaaaccg ctcccagccg    7380
acgacgagca agacgaagac agaagacgcg ctctgctaga tgaaacaaag gcgtggttta    7440
gagtaggtat aacaggcact ttagcagtgg ccgtgacgac ccggtatgag gtagacaata    7500
ttacacctgt cctactggca ttgagaactt ttgcccagag caaaagagca ttccaagcca    7560
tcagggggaa aataaagcat ctctacggtg gtcctaaata gtcagcatag tacatttcat    7620
ctgactaata ctacaacacc accaccatga atagaggatt ctttaacatg ctcggccgcc    7680
gccccttccc ggcccccact gccatgtgga ggccgcggag aaggaggcag gcggccccga    7740
tgcctgcccg caacgggctg gcttctcaaa tccagcaact gaccacagcc gtcagtgccc    7800
tagtcattgg acaggcaact agacctcaac ccccacgtcc acgcccgcca ccgcgccaga    7860
agaagcaggc gcccaagcaa ccaccgaagc cgaagaaacc aaaaacgcag gagaagaaga    7920
agaagcaacc tgcaaaaccc aaacccggaa agagacagcg catggcactt aagttggagg    7980
ccgacagatc gttcgacgtc aagaacgagg acggagatgt catcgggcac gcactggcca    8040
tggaaggaaa ggtaatgaaa cctctgcacg tgaaggaac catcgaccac cctgtgctat    8100
caaagctcaa atttaccaag tcgtcagcat acgacatgga gttcgcacag ttgccagtca    8160
```

```
acatgagaag tgaggcattc acctacacca gtgaacaccc cgaaggattc tataactggc   8220
accacggagc ggtgcagtat agtggaggta gatttaccat ccctcgcgga gtaggaggca   8280
gaggagacag cggtcgtccg atcatggata actccggtcg ggttgtcgcg atagtcctcg   8340
gtggagctga tgaaggaaca cgaactgccc tttcggtcgt cacctggaat agtaaaggga   8400
agacaattaa gacgaccccg gaagggacag aagagtggtc cgcagcacca ctggtcacgg   8460
caatgtgttt gctcggaaat gtgagcttcc catgcgaccg cccgcccaca tgctataccc   8520
gcgaaccttc cagagccctc gacatccttg aagagaacgt gaaccatgag gcctacgata   8580
ccctgctcaa tgccatattg cggtgcggat cgtctggcag aagcaaaaga agcgtcactg   8640
acgactttac cctgaccagc ccctacttgg gcacatgctc gtactgccac catactgaac   8700
cgtgcttcag ccctgttaag atcgagcagg tctgggacga agcggacgat aacaccatac   8760
gcatacagac ttccgcccag tttggatacg accaaagcgg agcagcaagc gcaaacaagt   8820
accgctacat gtcgcttaag caggatcaca ccgttaaaga aggcaccatg gatgacatca   8880
agattagcac ctcaggaccg tgtagaaggc ttagctacaa aggatacttt ctcctcgcaa   8940
aatgccctcc aggggacagc gtaacggtta gcatagtgag tagcaactca gcaacgtcat   9000
gtacactggc ccgcaagata aaaccaaaat tcgtgggacg ggaaaaatat gatctacctc   9060
ccgttcacgg taaaaaaatt ccttgcacag tgtacgaccg tctgaaagaa caactgcag    9120
gctacatcac tatgcacagg ccgggaccgc acgcttatac atcctacctg gaagaatcat   9180
cagggaaagt ttacgcaaag ccgccatctg gaagaacat tacgtatgag tgcaagtgcg     9240
gcgactacaa gaccagaacc gtttcgaccc gcaccgaaat cactggttgc accgccatca   9300
agcagtgcgt cgcctataag agcgaccaaa cgaagtgggt cttcaactca ccggacttga   9360
tcagacatga cgaccacacg gcccaaggga aattgcattt gcctttcaag ttgatcccga   9420
gtacctgcat ggtccctgtt gcccacgcgc cgaatgtaat acatggcttt aaacacatca   9480
gcctccaatt agatacagac cacttgacat tgctcaccac caggagacta ggggcaaacc   9540
cggaaccaac cactgaatgg atcgtcggaa agacggtcag aaacttcacc gtcgaccgag   9600
atggcctgga atacatatgg ggaaatcatg agccagtgag ggtctatgcc caagagtcag   9660
caccaggaga ccctcacgga tggccacacg aaatagtaca gcattactac catcgccatc   9720
ctgtgtacac catcttagcc gtcgcatcag ctaccgtggc gatgatgatt ggcgtaactg   9780
ttgcagtgtt atgtgcctgt aaagcgcgcc gtgagtgcct gacgccatac gccctggccc   9840
caaacgccgt aatcccaact tcgctggcac tcttgtgctg cgttaggtcg gccaatgctg   9900
aaacgttcac cgagaccatg agttacttgt ggtcgaacag tcagccgttc ttctgggtcc   9960
agttgtgcat accttttggcc gctttcatcg ttctaatgcg ctgctgctcc tgctgcctgc   10020
cttttttagt ggttgccggc gcctacctgg cgaaggtaga cgcctacgaa catgcgacca   10080
ctgttccaaa tgtgccacag ataccgtata aggcacttgt tgaaagggca gggtatgccc   10140
cgctcaattt ggagatcact gtcatgtcct cggaggtttt gccttccacc aaccaagagt   10200
acattacctg caaattcacc actgtggtcc cctccccaaa aatcaaatgc tgcggctcct   10260
tggaatgtca gccggccgtt catgcagact atacctgcaa ggtcttcgga ggggtctacc   10320
cctttatgtg gggaggagcg caatgttttt gcgacagtga aacagccag atgagtgagg    10380
cgtacgtcga actgtcagca gattgcgcgt ctgaccacgc gcaggcgatt aaggtgcaca   10440
ctgccgcgat gaaagtagga ctgcgtatag tgtacgggaa cactaccagt ttcctagatg   10500
tgtacgtgaa cggagtcaca ccaggaacgt ctaaagactt gaaagtcata gctggaccaa   10560
```

-continued

```
tttcagcatc gtttacgcca ttcgatcata aggtcgttat ccatcgcggc ctggtgtaca    10620
actatgactt cccggaatat ggagcgatga aaccaggagc gtttggagac attcaagcta    10680
cctccttgac tagcaaggat ctcatcgcca gcacagacat taggctactc aagccttccg    10740
ccaagaacgt gcatgtcccg tacacgcagg ccgcatcagg atttgagatg tggaaaaaca    10800
actcaggccg cccactgcag gaaaccgcac ctttcgggtg taagattgca gtaaatccgc    10860
tccgagcggt ggactgttca tacgggaaca ttcccatttc tattgacatc ccgaacgctg    10920
cctttatcag gacatcagat gcaccactgg tctcaacagt caaatgtgaa gtcagtgagt    10980
gcacttattc agcagacttc ggcgggatgg ccaccctgca gtatgtatcc gaccgcgaag    11040
gtcaatgccc cgtacattcg cattcgagca cagcaactct ccaagagtcg acagtacatg    11100
tcctggagaa aggagcggtg acagtacact ttagcaccgc gagtccacag gcgaacttta    11160
tcgtatcgct gtgtgggaag aagacaacat gcaatgcaga atgtaaacca ccagctgacc    11220
atatcgtgag caccccgcac aaaaatgacc aagaatttca gccgccatc tcaaaaacat     11280 catggagttg gctgtttgcc cttttcggcg gcgcctcgtc gctattaatt ataggactta    11340 tgattttgc ttgcagcatg atgctgacta gcacacgaag atgaccgcta cgccccaatg     11400
atccgaccag caaaactcga tgtacttccg aggaactgat gtgcataatg catcaggctg    11460
gtacattaga tccccgctta ccgcgggcaa tatagcaaca ctaaaaactc gatgtacttc    11520
cgaggaagcg cagtgcataa tgctgcgcag tgttgccaca taaccactat attaaccatt    11580
tatctagcgg acgccaaaaa ctcaatgtat ttctgaggaa gcgtggtgca taatgccacg    11640
cagcgtctgc ataacttta ttatttcttt tattaatcaa caaaattttg tttttaacat    11700
ttc                                                                 11703
```

<210> SEQ ID NO 2
<211> LENGTH: 11703
<212> TYPE: DNA
<213> ORGANISM: Sindbis virus

<400> SEQUENCE: 2

```
attgacggcg tagtacacac tattgaatca acagccgac caattgcact accatcacaa      60
tggagaagcc agtagtaaac gtagacgtag accccccagag tccgtttgtc gtgcaactgc    120
aaaaaagctt cccgcaattt gaggtagtag cacagcaggt cactccaaat gaccatgcta    180
atgccagaga ttttcgcat ctggccagta aactaatcga gctggaggtt cctaccacag     240
cgacgatctt ggacataggc agcgcaccgg ctcgtagaat gttttccgag caccagtatc    300
attgtgtctg ccccatgcgt agtccagaag acccggaccg catgatgaaa tatgccagta    360
aactggcgga aaagcgtgc aagattacaa acaagaactt gcatgagaag attaaggatc    420 tccgaccgt acttgatacg ccggatgctg aaacaccatc gctctgcttt cacaacgatg    480
ttacctgcaa catgcgtgcc gaatattccg tcatgcagga cgtgtatatc aacgctcccg    540
gaactatcta tcatcaggct atgaaaggcg tgcggaccct gtactggatt ggcttcgaca    600
ccacccagtt catgttctcg gctatggcag gttcgtaccc tgcgtacaac accaactggg    660
ccgacgagaa agtccttgaa gcgcgtaaca tcggactttg cagcacaaag ctgagtgaag    720
gtaggacagg aaaattgtcg ataatgagga agaaggagtt gaagcccggg tcgcgggttt    780
atttctccgt aggatcgaca ctttatccag aacacagagc cagcttgcag agctggcatc    840
ttccatcggt gttccacttg aatggaaagc agtcgtacac ttgccgctgt gatacagtgg    900
```

```
tgagttgcga aggctacgta gtgaagaaaa tcaccatcag tcccgggatc acgggagaaa      960
ccgtgggata cgcggttaca cacaatagcg agggcttctt gctatgcaaa gttactgaca     1020
cagtaaaagg agaacgggta tcgttccctg tgtgcacgta catcccggcc accatatgcg     1080
atcagatgac tggtataatg gccacggata tatcacctga cgatgcacaa aaacttctgg    1140
ttgggctcaa ccagcgaatt gtcattaacg gtaggactaa caggaacacc aacaccatgc     1200
aaaattacct tctgccgatc atagcacaag ggttcagcaa atgggctaag gagcgcaagg     1260
atgatcttga taacgagaaa atgctgggta ctagagaacg caagcttacg tacggctgct     1320
tgtgggcgtt tcgcactaag aaagtacatt cgttttatcg cccacctgga acgcagacca     1380
tcgtaaaagt cccagcctct tttagcgctt ttcccatgtc gtccgtatgg acgacctctt     1440
tgcccatgtc gctgaggcag aaattgaaac tggcattgca accaaagaag gaggaaaaac     1500
tgctgcaggt ctcggaggaa ttagtcatgg aggccaaggc tgcttttgag gatgctcagg     1560
aggaagccag agcggagaag ctccgagaag cacttccacc attagtggca gacaaaggca     1620
tcgaggcagc cgcagaagtt gtctgcgaag tggagggggct ccaggcggac atcggagcag     1680
cattagttga aaccccgcgc ggtcacgtaa ggataatacc tcaagcaaat gaccgtatga     1740
tcggacagta tatcgttgtc tcgccaaact ctgtgctgaa gaatgccaaa ctcgcaccag     1800
cgcacccgct agcagatcag gttaagatca taacacactc cggaagatca ggaaggtacg     1860
cggtcgaacc atacgacgct aaagtactga tgccagcagg aggtgccgta ccatggccag     1920
aattcctagc actgagtgag agcgccacgt tagtgtacaa cgaaagagag tttgtgaacc     1980
gcaaactata ccacattgcc atgcatggcc ccgccaagaa tacagaagag gagcagtaca     2040
aggttacaaa ggcagagctt gcagaaacag agtacgtgtt tgacgtggac aagaagcgtt     2100
gcgttaagaa ggaagaagcc tcaggtctgg tcctctcggg agaactgacc aaccctccct     2160
atcatgagct agctctggag ggactgaaga cccgacctgc ggtcccgtac aaggtcgaaa     2220
caataggagt gataggcaca ccggggtcgg gcaagtcagc tattatcaag tcaactgtca     2280
cggcacgaga tcttgttacc agcggaaaga agaaaaattg tcgcgaaatt gaggccgacg     2340
tgctaagact gagggggtatg cagattacgt cgaagacagt agattcggtt atgctcaacg     2400
gatgccacaa agccgtagaa gtgctgtacg ttgacgaagc gttcgcgtgc cacgcaggag     2460
cactacttgc cttgattgct atcgtcaggc cccgcaagaa ggtagtacta tgcggagacc     2520
ccatgcaatg cggattcttc aacatgatgc aactaaaggt acatttcaat caccctgaaa     2580
aagacatatg caccaagaca ttctacaagt atatctcccg cgcgttgcaca cagccagtta     2640 cagctattgt atcgacactg cattacgatg gaaagatgaa aaccacgaac ccgtgcaaga     2700
agaacattga aatcgatatt acaggggcca caaagccgaa gccagggggat atcatcctga     2760 catgttttccg cgggtggggtt aagcaattgc aaatcgacta tcccggacat gaagtaatga     2820
cagccgcggc ctcacaaggg ctaaccagaa aaggagtgta tgccgtccgg caaaaagtca     2880
atgaaaaccc actgtacgcg atcacatcag agcatgtgaa cgtgttgctc acccgcactg     2940
aggacaggct agtgtggaaa accttgcagg gcgacccatg gattaagcag ctcactaaca     3000
tacctaaagg aaactttcag gctactatag aggactggga agctgaacac aagggaataa     3060
ttgctgcaat aaacagcccc actccccgtg ccaatccgtt cagctgcaag accaacgttt     3120
gctgggcgaa agcattggaa ccgatactag ccacggccgg tatcgtactt accggttgcc     3180
agtggagcga actgttccca cagtttgcgg atgacaaacc acattcggcc atttacgcct     3240
tagacgtaat ttgcattaag ttttttcggca tggacttgac aagcggactg ttttctaaac     3300
```

```
agagcatccc actaacgtac catcccgccg attcagcgag gccggtagct cattgggaca    3360
acagcccagg aacccgcaag tatgggtacg atcacgccat tgccgccgaa ctctcccgta    3420
gatttccggt gttccagcta gctgggaagg cacacaact tgatttgcag acggggagaa     3480
ccagagttat ctctgcacag cataacctgg tcccggtgaa ccgcaatctt cctcacgcct    3540
tagtccccga gtacaaggag aagcaacccg gccggtcga aaaattcttg aaccagttca     3600
aacaccactc agtacttgtg gtatcagagg aaaaaattga agctccccgt aagagaatcg    3660
aatggatcgc cccgattggc atagccggtg cagataagaa ctacaacctg ctttcgggt     3720 ttccgccgca ggcacggtac gacctggtgt tcatcaacat tggaactaaa tacagaaacc    3780
accactttca gcagtgcgaa gaccatgcgg cgaccttaaa aaccctttcg cgttcggccc    3840
tgaattgcct taacccagga ggcaccctcg tggtgaagtc ctatggctac gccgaccgca    3900
acagtgagga cgtagtcacc gctcttgcca gaaagtttgt cagggtgtct gcagcgagac    3960
cagattgtgt ctcaagcaat acagaaatgt acctgatttt ccgacaacta gacaacagcc    4020
gtacacggca attcacccg caccatctga attgcgtgat ttcgtccgtg tatgagggta     4080
caagagatgg agttggagcc gcgccgtcat accgcaccaa aagggagaat attgctgact    4140
gtcaagagga agcagttgtc aacgcagcca atccgctggg tagaccaggc gaaggagtct    4200
gccgtgccat ctataaacgt tggccgacca gttttaccga ttcagccacg agacaggca    4260 ccgcaagaat gactgtgtgc ctaggaaaga aagtgatcca cgcggtcggc cctgatttcc    4320
ggaagcaccc agaagcagaa gccttgaaat tgctacaaaa cgcctaccat gcagtggcag    4380
acttagtaaa tgaacataac atcaagtctg tcgccattcc actgctatct acaggcattt    4440
acgcagccgg aaaagaccgc cttgaagtat cacttaactg cttgacaacc gcgctagaca    4500
gaactgacgc ggacgtaacc atctattgcc tggataagaa gtggaaggaa agaatcgacg    4560
cggcactcca acttaaggag tctgtaacag agctgaagga tgaagatatg gagatcgacg    4620
atgagttagt atggatccat ccagacagtt gcttgaaggg aagaaaggga ttcagtacta    4680
caaaaggaaa attgtattcg tacttcgaag gcaccaaatt ccatcaagca gcaaaagaca    4740
tggcggagat aaaggtcctg ttccctaatg accaggaaag taatgaacaa ctgtgtgcct    4800
acatattggg tgagaccatg gaagcaatcc gcgaaaagtg cccggtcgac cataacccgt    4860
cgtctagccc gcccaaaacg ttgccgtgcc tttgcatgta tgccatgacg ccagaaaggg    4920
tccacagact tagaagcaat aacgtcaaag aagttacagt atgctcctcc acccccctc     4980 ctaagcacaa aattaagaat gttcagaagg ttcagtgcac gaaagtagtc ctgtttaatc    5040
cgcacactcc cgcattcgtt cccgcccgta agtacataga agtgccagaa cagcctaccg    5100
ctcctcctgc acaggccgag gaggcccccg aagttgtagc gacaccgtca ccatctacag    5160
ctgataacac ctcgcttgat gtcacagaca tctcactgga tatggatgac agtagcgaag    5220
gctcactttt ttcgagcttt agcggatcgg acaactctat tactagtatg gacagttggt    5280
cgtcaggacc tagttcacta gagatagtag accgaaggca ggtggtggtg gctgacgttc    5340
atgccgtcca agagcctgcc cctattccac cgccaaggct aaagaagatg gcccgcctgg    5400
cagcggctag aaaagagccc actccaccgg caagcaatag ctctgagtcc ctccacctct    5460
cttttggtgg ggtatccatg tccctcggat caattttcga cggagagacg gcccgccagg    5520
cagcggtaca accctggca acaggcccca cggatgtgcc tatgtctttc ggatcgtttt     5580
ccgacggaga gattgatgag ctgagccgca gagtaactga gtccgaaccc gtcctgtttg    5640
```

```
gatcatttga accgggcgaa gtgaactcaa ttatatcgtc ccgatcagcc gtatcttttc   5700
cactacgcaa gcagagacgt agacgcagga gcaggaggac tgaatactga ctaaccgggg   5760
taggtgggta catattttcg acggacacag gccctgggca cttgcaaaag aagtccgttc   5820
tgcagaacca gcttacagaa ccgaccttgg agcgcaatgt cctggaaaga attcatgccc   5880
cggtgctcga cacgtcgaaa gaggaacaac tcaaactcag gtaccagatg atgcccaccg   5940
aagccaacaa aagtaggtac cagtctcgta aagtagaaaa tcagaaagcc ataaccactg   6000
agcgactact gtcaggacta cgactgtata actctgccac agatcagcca gaatgctata   6060
agatcaccta tccgaaacca ttgtactcca gtagcgtacc ggcgaactac tccgatccac   6120
agttcgctgt agctgtctgt aacaactatc tgcatgagaa ctatccgaca gtagcatctt   6180
atcagattac tgacgagtac gatgcttact ggatatggt agacgggaca gtcgcctgcc    6240
tggatactgc aaccttctgc cccgctaagc ttagaagtta cccgaaaaaa catgagtata   6300
gagccccgaa tatccgcagt gcggttccat cagcgatgca gaacacgcta caaaatgtgc   6360
tcattgccgc aactaaaaga aattgcaacg tcacgcagat gcgtgaactg ccaacactgg   6420
actcagcgac attcaatgtc gaatgctttc gaaaatatgc atgtaatgac gagtattggg   6480
aggagttcgc tcggaagcca attaggatta ccactgagtt tgtcaccgca tatgtagcta   6540
gactgaaagg ccctaaggcc gccgcactat ttgcaaagac gtataatttg gtcccattgc   6600
aagaagtgcc tatggataga ttcgtcatgg acatgaaaag ggacgtgaaa gttacaccag   6660
gcacgaaaca cacagaagaa agaccgaaag tacaagtgat acaagccgca gaaccccctgg  6720 cgactgctta cttatgcggg attcaccggg aattagtgcg taggcttacg gccgtcttgc   6780
ttccaaacat tcacacgctt tttgacatgt cggcggagga ttttgatgca atcatagcag   6840
aacacttcaa gcaaggcgac ccggtactgg agacggatat cgcatcattc gacaaaagcc   6900
aagacgacgc tatggcgtta accggtctga tgatcttgga ggacctgggt gtggatcaac   6960
cactactcga cttgatcgag tgcgcctttg gagaaatatc atccacccat ctacctacgg   7020
gtactcgttt taaattcggg gcgatgatga atccggaat gttcctcaca cttttgtca    7080 acacagtttt gaatgtcgtt atcgccagca gagtactaga agagcggctt aaaacgtcca   7140
gatgtgcagc gttcattggc gacgacaaca tcatacatgg agtagtatct gacaaagaaa   7200
tggctgagag gtgcgccacc tggctcaaca tggaggttaa gatcatcgac gcagtcatcg   7260
gtgagagacc accttacttc tgcggcggat ttatcttgca agattcggtt acttccacag   7320
cgtgccgcgt ggcggacccc ctgaaaaggc tgtttaagtt gggtaaaccg ctcccagccg   7380
acgacgagca agacgaagac agaagacgcg ctctgctaga tgaaacaaag gcgtggttta   7440
gagtaggtat aacaggcact ttagcagtgg ccgtgacgac ccggtatgag gtagacaata   7500
ttacacctgt cctactggca ttgagaactt ttgcccagag caaaagagca ttccaagcca   7560
tcagagggga aataaagcat ctctacggtg gtcctaaata gtcagcatag tacatttcat   7620
ctgactaata ctacaacacc accaccatga atagaggatt ctttaacatg ctcggccgcc   7680
gccccttccc ggcccccact gccatgtgga ggccgcggaa aaggaggcag gcggccccga   7740
tgcctgcccg caacgggctg gcttctcaaa tccagcaact gaccacagcc gtcagtgccc   7800
tagtcattgg acaggcaact agacctcaac ccccacgtcc acgccgcca ccgcgccaga    7860 agaagcaggc gcccaagcaa ccaccgaagc cgaagaaacc aaaaacgcag gagaagaaga   7920
agaagcaacc tgcaaaaccc aaacccggaa agagacagcg catggcactt aagttggagg   7980
ccgacagatc gttcgacgtc aagaacgagg acggagatgt catcgggcac gcactggcca   8040
```

```
tggaaggaaa ggtaatgaaa cctctgcacg tgaaaggaac catcgaccac cctgtgctat    8100
caaagctcaa atttaccaag tcgtcagcat acgacatgga gttcgcacag ttgccagtca    8160
acatgagaag tgaggcattc acctacacca gtgaacaccc cgaaggattc tataactggc    8220
accacggagc ggtgcagtat agtggaggta gatttaccat ccctcgcgga gtaggaggca    8280
gaggagacag cggtcgtccg atcatggata actccggtcg ggttgtcgcg atagtcctcg    8340
gtggagctga tgaaggaaca cgaactgccc tttcggtcgt cacctggaat agtaaaggga    8400
agacaattaa gacgaccccg gaagggacag aagagtggtc cgcagcacca ctggtcacgg    8460
caatgtgttt gctcggaaat gtgagcttcc catgcgaccg cccgcccaca tgctataccc    8520
gcgaaccttc cagagccctc gacatccttg aagagaacgt gaaccatgag gcctacgata    8580
ccctgctcaa tgccatattg cggtgcggat cgtctggcag aagcaaaaga agcgtcactg    8640
acgactttac cctgaccagc ccctacttgg gcacatgctc gtactgccac catactgaac    8700
cgtgcttcag ccctgttaag atcgagcagg tctgggacga agcggacgat aacaccatac    8760
gcatacagac ttccgcccag tttggatacg accaaagcgg agcagcaagc gcaaacaagt    8820
accgctacat gtcgcttaag caggatcaca ccgttaaaga aggcaccatg gatgacatca    8880
agattagcac ctcaggaccg tgtagaaggc ttagctacaa aggatacttt ctcctcgcaa    8940
aatgccctcc aggggacagc gtaacggtta gcatagtgag tagcaactca gcaacgtcat    9000
gtacactggc ccgcaagata aaaccaaaat tcgtgggacg ggaaaaatat gatctacctc    9060
ccgttcacgg taaaaaaatt ccttgcacag tgtacgaccg tctgaaagga acaactgcag    9120
gctacatcac tatgcacagg ccgggaccgc acgcttatac atcctacctg aagaatcat    9180 cagggaaagt ttacgcaaag ccgccatctg gaagaacat tacgtatgag tgcaagtgcg    9240
gcgactacaa gaccagaacc gtttcgaccc gcaccgaaat cactggttgc accgccatca    9300
agcagtgcgt cgcctataag agcgaccaaa cgaagtgggg cttcaactca ccggacttga    9360
tcagacatga cgaccacacg gcccaaggga aattgcattt gccttttcaag ttgatcccga    9420 gtacctgcat ggtccctgtt gcccacgcgc cgaatgtaat acatggcttt aaacacatca    9480
gcctccaatt agatacagac cacttgacat tgctcaccac caggagacta ggggcaaacc    9540
cggaaccaac cactgaatgg atcgtcggaa agacggtcag aaacttcacc gtcgaccgag    9600
atggcctgga atacatatgg ggaaatcatg agccagtgag ggtctatgcc caagagtcag    9660
caccaggaga ccctcacgga tggccacacg aaatagtaca gcattactac catcgccatc    9720
ctgtgtacac catcttagcc gtcgcatcag ctaccgtggc gatgatgatt ggcgtaactg    9780
ttgcagtgtt atgtgcctgt aaagcgcgcc gtgagtgcct gacgccatac gccctggccc    9840
caaacgccgt aatcccaact tcgctggcac tcttgtgctg cgttaggtcg gccaatgctg    9900
aaacgttcac cgagaccatg agttacttgt ggtcgaacag tcagccgttc ttctgggtcc    9960
agttgtgcat acctttggcc gctttcatcg ttctaatgcg ctgctgctcc tgctgcctgc    10020
cttttttagt ggttgccggc gcctacctgg cgaaggtaga cgcctacgaa catgcgacca    10080
ctgttccaaa tgtgccacag ataccgtata aggcacttgt tgaaagggca gggtatgccc    10140
cgctcaattt ggagatcact gtcatgtcct cggaggtttt gccttccacc aaccaagagt    10200
acattaccct gcaaattcac cactgtggtcc cctccccaaa aatcaaatgc tgcggctcct    10260
tggaatgtca gccggccgtt catgcagact atacctgcaa ggtcttcgga ggggtctacc    10320
cctttatgtg gggaggagcg caatgttttt gcgacagtga gaacagccag atgagtgagg    10380
```

-continued

```
cgtacgtcga actgtcagca gattgcgcgt ctgaccacgc gcaggcgatt aaggtgcaca    10440
ctgccgcgat gaaagtagga ctgcgtatag tgtacgggaa cactaccagt ttcctagatg    10500
tgtacgtgaa cggagtcaca ccaggaacgt ctaaagactt gaaagtcata gctggaccaa    10560
tttcagcatc gtttacgcca ttcgatcata aggtcgttat ccatcgcggc ctggtgtaca    10620
actatgactt cccggaatat ggagcgatga aaccaggagc gtttggagac attcaagcta    10680
cctccttgac tagcaaggat ctcatcgcca gcacagacat taggctactc aagccttccg    10740
ccaagaacgt gcatgtcccg tacacgcagg ccgcatcagg atttgagatg tggaaaaaca    10800
actcaggccg cccactgcag gaaaccgcac ctttcgggtg taagattgca gtaaatccgc    10860
tccgagcggt ggactgttca tacgggaaca ttcccatttc tattgacatc ccgaacgctg    10920
cctttatcag gacatcagat gcaccactgg tctcaacagt caaatgtgaa gtcagtgagt    10980
gcacttattc agcagacttc ggcgggatgg ccaccctgca gtatgtatcc gaccgcgaag    11040
gtcaatgccc cgtacattcg cattcgagca cagcaactct ccaagagtcg acagtacatg    11100
tcctggagaa aggagcggtg acagtacact ttagcaccgc gagtccacag gcgaacttta    11160
tcgtatcgct gtgtgggaag aagacaacat gcaatgcaga atgtaaacca ccagctgacc    11220
atatcgtgag caccccgcac aaaaatgacc aagaatttca agccgccatc tcaaaaacat    11280
catggagttg gctgtttgcc cttttcggcg gcgcctcgtc gctattaatt ataggactta    11340 tgattttgc ttgcagcatg atgctgacta gcacacgaag atgaccgcta cgccccaatg    11400
atccgaccag caaaactcga tgtacttccg aggaactgat gtgcataatg catcaggctg    11460
gtacattaga tccccgctta ccgcgggcaa tatagcaaca ctaaaaactc gatgtacttc    11520
cgaggaagcg cagtgcataa tgctgcgcag tgttgccaca taaccactat attaaccatt    11580
tatctagcgg acgccaaaaa ctcaatgtat ttctgaggaa gcgtggtgca taatgccacg    11640
cagcgtctgc ataacttta ttatttcttt tattaatcaa caaaattttg tttttaacat    11700
ttc                                                                 11703
```

<210> SEQ ID NO 3
<211> LENGTH: 33
<212> TYPE: DNA
<213> ORGANISM: Artificial Sequence
<220> FEATURE:
<223> OTHER INFORMATION: PCR primer

<400> SEQUENCE: 3
ccacaagctt gatctaatgt accagcctga tgc                                 33

<210> SEQ ID NO 4
<211> LENGTH: 27
<212> TYPE: DNA
<213> ORGANISM: Artificial Sequence
<220> FEATURE:
<223> OTHER INFORMATION: PCR primer

<400> SEQUENCE: 4
ccacgaattc agccagatga gtgaggc                                        27

<210> SEQ ID NO 5
<211> LENGTH: 30
<212> TYPE: DNA
<213> ORGANISM: Artificial Sequence
<220> FEATURE:
<223> OTHER INFORMATION: PCR primer

<400> SEQUENCE: 5
ccacaagctt caattcgacg tacgcctcac                                    30

<210> SEQ ID NO 6
<211> LENGTH: 30
<212> TYPE: DNA
<213> ORGANISM: Artificial Sequence
<220> FEATURE:
<223> OTHER INFORMATION: PCR primer

<400> SEQUENCE: 6
ccacgaattc atatggggaa atcatgagcc                                    30

<210> SEQ ID NO 7
<211> LENGTH: 29
<212> TYPE: DNA
<213> ORGANISM: Artificial Sequence
<220> FEATURE:
<223> OTHER INFORMATION: PCR primer

<400> SEQUENCE: 7
ccacaagctt catagaccct cactggctc                                     29

<210> SEQ ID NO 8
<211> LENGTH: 30
<212> TYPE: DNA
<213> ORGANISM: Artificial Sequence
<220> FEATURE:
<223> OTHER INFORMATION: PCR primer

<400> SEQUENCE: 8
ccacgaattc aagattagca cctcaggacc                                    30

<210> SEQ ID NO 9
<211> LENGTH: 29
<212> TYPE: DNA
<213> ORGANISM: Artificial Sequence
<220> FEATURE:
<223> OTHER INFORMATION: PCR primer

<400> SEQUENCE: 9
ccacaagctt ctacacggtc ctgaggtgc                                     29

<210> SEQ ID NO 10
<211> LENGTH: 30
<212> TYPE: DNA
<213> ORGANISM: Artificial Sequence
<220> FEATURE:
<223> OTHER INFORMATION: PCR primer

<400> SEQUENCE: 10
ccacgaattc gtccgatcat ggataactcc                                    30

<210> SEQ ID NO 11
<211> LENGTH: 24
<212> TYPE: DNA
<213> ORGANISM: Artificial Sequence
<220> FEATURE:
<223> OTHER INFORMATION: PCR primer

<400> SEQUENCE: 11
ccacaagctt gcgccaccga ggac                                          24

<210> SEQ ID NO 12
<211> LENGTH: 27
<212> TYPE: DNA

```
<213> ORGANISM: Artificial Sequence
<220> FEATURE:
<223> OTHER INFORMATION: PCR primer

<400> SEQUENCE: 12
ccacgaattc actgccatgt ggaggcc                                        27

<210> SEQ ID NO 13
<211> LENGTH: 30
<212> TYPE: DNA
<213> ORGANISM: Artificial Sequence
<220> FEATURE:
<223> OTHER INFORMATION: PCR primer

<400> SEQUENCE: 13
ccacctcgag tttacccaac ttaaacagcc                                     30

<210> SEQ ID NO 14
<211> LENGTH: 31
<212> TYPE: DNA
<213> ORGANISM: Artificial Sequence
<220> FEATURE:
<223> OTHER INFORMATION: PCR primer

<400> SEQUENCE: 14
ccacgagctc gcgacattca atgtcgaatg c                                   31

<210> SEQ ID NO 15
<211> LENGTH: 31
<212> TYPE: DNA
<213> ORGANISM: Artificial Sequence
<220> FEATURE:
<223> OTHER INFORMATION: PCR primer

<400> SEQUENCE: 15
ccacctcgag gaactcctcc caatactcgt c                                   31

<210> SEQ ID NO 16
<211> LENGTH: 30
<212> TYPE: DNA
<213> ORGANISM: Artificial Sequence
<220> FEATURE:
<223> OTHER INFORMATION: PCR primer

<400> SEQUENCE: 16
ccacgagctc gaccttggag cgcaatgtcc                                     30

<210> SEQ ID NO 17
<211> LENGTH: 29
<212> TYPE: DNA
<213> ORGANISM: Artificial Sequence
<220> FEATURE:
<223> OTHER INFORMATION: PCR primer

<400> SEQUENCE: 17
ccacctcgag tttcgacgtg tcgagcacc                                      29

<210> SEQ ID NO 18
<211> LENGTH: 29
<212> TYPE: DNA
<213> ORGANISM: Artificial Sequence
<220> FEATURE:
<223> OTHER INFORMATION: PCR primer

<400> SEQUENCE: 18
ccacgagctc gaccatggaa gcaatccgc                                      29
```

-continued

<210> SEQ ID NO 19
<211> LENGTH: 29
<212> TYPE: DNA
<213> ORGANISM: Artificial Sequence
<220> FEATURE:
<223> OTHER INFORMATION: PCR primer

<400> SEQUENCE: 19
ccacctcgag acgacgggtt atggtcgac                                    29

<210> SEQ ID NO 20
<211> LENGTH: 28
<212> TYPE: DNA
<213> ORGANISM: Artificial Sequence
<220> FEATURE:
<223> OTHER INFORMATION: PCR primer

<400> SEQUENCE: 20
ccacgagctc cacggagaca ggcaccgc                                     28

<210> SEQ ID NO 21
<211> LENGTH: 32
<212> TYPE: DNA
<213> ORGANISM: Artificial Sequence
<220> FEATURE:
<223> OTHER INFORMATION: PCR primer

<400> SEQUENCE: 21
ccacctcgag gatcactttc tttcctaggc ac                                32

<210> SEQ ID NO 22
<211> LENGTH: 30
<212> TYPE: DNA
<213> ORGANISM: Artificial Sequence
<220> FEATURE:
<223> OTHER INFORMATION: PCR primer

<400> SEQUENCE: 22
ccacgagctc gaactctccc gtagatttcc                                   30

<210> SEQ ID NO 23
<211> LENGTH: 30
<212> TYPE: DNA
<213> ORGANISM: Artificial Sequence
<220> FEATURE:
<223> OTHER INFORMATION: PCR primer

<400> SEQUENCE: 23
ccacctcgag atcaagttgt gtgcccttcc                                   30

<210> SEQ ID NO 24
<211> LENGTH: 30
<212> TYPE: DNA
<213> ORGANISM: Artificial Sequence
<220> FEATURE:
<223> OTHER INFORMATION: PCR primer

<400> SEQUENCE: 24
ccacgagctc ccaggggata tcatcctgac                                   30

<210> SEQ ID NO 25
<211> LENGTH: 31
<212> TYPE: DNA
<213> ORGANISM: Artificial Sequence
<220> FEATURE:

<223> OTHER INFORMATION: PCR primer

<400> SEQUENCE: 25
ccacctcgag gctgtcatta cttcatgtcc g     31

<210> SEQ ID NO 26
<211> LENGTH: 34
<212> TYPE: DNA
<213> ORGANISM: Artificial Sequence
<220> FEATURE:
<223> OTHER INFORMATION: PCR primer

<400> SEQUENCE: 26
ccacgagctc gaaccgcaaa ctataccaca ttgc     34

<210> SEQ ID NO 27
<211> LENGTH: 30
<212> TYPE: DNA
<213> ORGANISM: Artificial Sequence
<220> FEATURE:
<223> OTHER INFORMATION: PCR primer

<400> SEQUENCE: 27
ccacctcgag cttgtactgc tcctcttctg     30

<210> SEQ ID NO 28
<211> LENGTH: 29
<212> TYPE: DNA
<213> ORGANISM: Artificial Sequence
<220> FEATURE:
<223> OTHER INFORMATION: PCR primer

<400> SEQUENCE: 28
ccacgagctc ggagaacggg tatcgttcc     29

<210> SEQ ID NO 29
<211> LENGTH: 27
<212> TYPE: DNA
<213> ORGANISM: Artificial Sequence
<220> FEATURE:
<223> OTHER INFORMATION: PCR primer

<400> SEQUENCE: 29
ccacctcgag ccgggatgta cgtgcac     27

<210> SEQ ID NO 30
<211> LENGTH: 30
<212> TYPE: DNA
<213> ORGANISM: Artificial Sequence
<220> FEATURE:
<223> OTHER INFORMATION: PCR primer

<400> SEQUENCE: 30
ccacgagctc attgacggcg tagtacacac     30

<210> SEQ ID NO 31
<211> LENGTH: 20
<212> TYPE: DNA
<213> ORGANISM: Artificial Sequence
<220> FEATURE:
<223> OTHER INFORMATION: PCR primer

<400> SEQUENCE: 31
gattcggtta cttccacagc     20

```
<210> SEQ ID NO 32
<211> LENGTH: 20
<212> TYPE: DNA
<213> ORGANISM: Artificial Sequence
<220> FEATURE:
<223> OTHER INFORMATION: PCR primer

<400> SEQUENCE: 32
actgacggct gtggtcagtt                                              20

<210> SEQ ID NO 33
<211> LENGTH: 20
<212> TYPE: DNA
<213> ORGANISM: Artificial Sequence
<220> FEATURE:
<223> OTHER INFORMATION: PCR primer

<400> SEQUENCE: 33
gatgtacttc cgaggaactg                                              20

<210> SEQ ID NO 34
<211> LENGTH: 34
<212> TYPE: DNA
<213> ORGANISM: Artificial Sequence
<220> FEATURE:
<223> OTHER INFORMATION: PCR primer

<400> SEQUENCE: 34
ccacaagctt gaaatgttaa aaacaaaatt ttgt                              34

<210> SEQ ID NO 35
<211> LENGTH: 26
<212> TYPE: DNA
<213> ORGANISM: Artificial Sequence
<220> FEATURE:
<223> OTHER INFORMATION: PCR primer

<400> SEQUENCE: 35
gcacgtgggc ccggcgcctc tagagc                                       26

<210> SEQ ID NO 36
<211> LENGTH: 26
<212> TYPE: DNA
<213> ORGANISM: Artificial Sequence
<220> FEATURE:
<223> OTHER INFORMATION: PCR primer

<400> SEQUENCE: 36
gctctagagg cgccgggccc acgtgc                                       26
```